US005510264A

United States Patent [19]

Van Alstyne et al.

[11] Patent Number: 5,510,264
[45] Date of Patent: Apr. 23, 1996

[54] ANTIBODIES WHICH BIND MENINGITIS RELATED HOMOLOGOUS ANTIGENIC SEQUENCES

[75] Inventors: Diane Van Alstyne; Lawrence R. Sharma, both of Vancouver, Canada

[73] Assignee: Insight Biotech Inc., St. Michael, Barbados

[21] Appl. No.: 127,499

[22] Filed: Sep. 28, 1993

[51] Int. Cl.$^6$ .......................... C12N 5/12; C07K 16/18; C07K 16/24; G01N 3/353

[52] U.S. Cl. .......................... 435/240.27; 530/387.9; 530/388.2; 530/388.3; 530/388.4; 530/388.23; 435/7.2

[58] Field of Search .......................... 530/388.3, 388.4, 530/387.9, 388.2, 388.23; 435/240.27, 7.2; 424/147.1, 150.1

[56] References Cited

PUBLICATIONS

Green et al. "The *e* (P4) Outer Membrane Protein of *Haemophilus influenzae:* Biologic Activity of Anti–*e* Serum and Cloning and Sequencing of the Structural Gene," *Infection and Immunology* 59:3191–3198 (1991).
Roos "Chapter 16", Sheld, et al. eds., *Infections of the CNS*:335 (1991).
Herrmann "Rubella Virus", *Diagnostic Procedures for Viral, Rickettsial and Chlamydial Infections:* 725 (1979).
Spalding "In Hot Pursuit of an HIV Vaccine", *Biotech* 10:24–29 (1992).
Griffiss et al. "Vaccines Against Encapsulated Bacteria: A Global Agenda", *Rev. Infec. Dis.* 9:176–188 (1987).
Yoshimura et al. "Human monocycle chemoattractant protein–1 (MCP–1)", *FEBS Letters* 244:487–493 (1989).
Terry et al. "Localization of the rubella E1 epitopes", *Arch. Virol.* 98:189–197 (1988).
Connolly et al. "Carotid Artery Thrombosis, Encephalitis, Myelitis and Optic Neuritis Associated with Rubella Virus Infections", *Brain* 98:583–594 (1975).
Pope and Van Alstyne "Evidence for Restricted Replication of rubella Virus in Rat Glial Cells in Culture", *Virology* 113:776–780 (1981).
Van Alstyne and Paty "The Effect of Dibutyryl Cyclic AMP on Restricted Replication of Rubella Virus in Rat Glial Cells in Culture", *Virology* 124:173–180 (1983).
Voller and Bidwell "A Single Method for Detecting Antibodies to Rubella", *Br. J. Exp. Path.* 56:338–339 (1975).
Parkman and Meyer "Attenuated Rubella Virus", *The New England Journal of Medicine* 275:569–580 (1966).
Stephens et al. "Equine Infectious Anemia Virus *gag and pol* Genes: Relatedness to the Visna and AIDS Virus", *Science* 231:589–594 (1986).
Ho et al. "Primary Human T–Lymphotropic Virus Type III Infection", *Annals of Internal Medicine* 103:880–883 (1985).
Muesing et al. "Nucleic acid structure and expression of the human AIDS/lymphadenopathy retrovirus", *Nature* 313:450–458 (1985).
Fraser et al. "Bacterial Meningitis in Bernilillo County, New Mexico: A Comparison with Three Other American Populations", *Am. J. of Epidemology* 100:29–34 (1974).
Yother and Briles "Structural Properties and Evolutionary Relationships of PspA, a Surface Protein of *Streptococcus pneumoniae* as Revealed by Sequence Analysis", *J. of Bacteriology* 174:601–609 (1992).
Tunkel et al. "Bacterial Meningitis: Recent Advances in Pathophysiology and Treatment", *Annals of Internal Medicine* 112:610–623 (1990).
Stern and Meyer "Common mechanism controlling phase and antigenic variation in pathogenic neisseriae", *Molecular Microbiology* 1:5–12 (1987).
Goebel et al. "Studies on the Pathogenicity of listeria monocytogenes", *Infection* 19:S195–197 (1991).
Michel and Cossart "Physical Map of the *monocytogenes* Chromosome", *Journal of Bacteriology* 174:7098–7103 (1992).
Kohler et al. "The Gene Coding for Protein p60 of *Listeria monocytogenes* and Its use as a Specific probe for *Listeria monocytogenes", Infection and Immunity* 58:1943–1950 (1990).
Cordy "Pathomorphiology and Pathogenesis of Bacteria Meningoventriculitis of Neonatal Ungulates", *Vet. Pathol.* 21:587–591 (1984).
Robinson et al. "Complete amino acid sequence of a human monocyte chemoattractant, a putative mediator of cellular immune reactions", *Proc. Natl. Acad. Sci. USA* 86:1850–1854 (1989).
Michiel et al. "Chemokines: The Missing Link", *Bio/technology* 11:739 (1993).
Rollins et al. "The Human Homolog of the *JE* Gene Encodes a Monocyte Secretary Protein", *Molecular and Cellular Biology* 9:4687–4695 (1989).
Van Damme et al. "Structural and Functional Indentification of Two Human, Tumor–derived Monocyte Chemotactic Proteins (MCP–2 and MCP–3) Belonging to the Chemokine Family", *J. Exp. Med.* 176:59–64 (1992).
Waldmann, T. A. Science, 252:1657–1662, Jun. 21, 1991.
Waxham, M. Neal et al., Virology, 143:153–165, 1985.

*Primary Examiner*—Margaret Parr
*Assistant Examiner*—Susan A. Loring
*Attorney, Agent, or Firm*—Foley & Lardner

[57] ABSTRACT

Monoclonal antibodies capable of binding to a Meningitis Related Homologous Antigenic Sequence (MRHAS) are provided. The MRHAS is found in meningitis-causing organisms and chemokines involved in cell chemotaxis. The monoclonal antibodies are useful for detection and diagnosis of meningitis.

24 Claims, 9 Drawing Sheets

FIG. 1

```
          10         20         30         40         50
  1 MASTTPITME DLQKALEAQS RALRAGLAAG ASQSRRPRPP RHARLQHLPE      50
          60         70         80         90        100
 51 MTPAVTPEGP APPRTGAWQR KDWSRAPPPP EERQESRSQT PAPKPSRAPP     100
         110        120        130        140        150
101 QQPQPPRMQT GRGGSAPRPE LGPPTNPFQA AVARGLRPPL HDPDTEAPTE     150
         160        170        180        190        200
151 ACVTSWLWSE GEGAVFYRVD LHFINLGTPP LDEDGRWDPA LMYNPCGPEP     200
         210        220        230        240        250
201 PAHVVRAYNQ PAGDVRGVWG KGERTYAEQD FRVGGTRWHR LLRMPVRGLD     250
         260        270        280        290        300
251 GDTAPLPPHT TERIETRSAR HPWRIRFGAP QAFLAGLLLA AVAVGTARAG     300
         310        320        330        340        350
301 LQPRADMAAP PMPPQPPRAH GQHYGHHHHQ LPFLGHDGHH GGTLRVGQHH     350
         360        370        380        390        400
351 RNASDVLPGH WLQGGWGCYN LSDWHQGTHV CHTKHMDFWC VEHDRPPPAT     400
         410        420        430        440        450
401 PTSLTTAANY IAAATPATAP PPCHAGLNDS CGGFLSGCGP MRLPTALTPG     450
         460        470        480        490        500
451 AVGDLRAVHH RPVPAYPVCC AMRWGLPPWE LVILTARPED GWTCRGVPAH     500
         510        520        530        540        550
501 PGTRCPELVS PMGRATCSPA SALWLATANA LSLDHAFAAF VLLVPWVLIF     550
         560        570        580        590        600
551 MVCRRACRRP APPPPSPQSS CRGTTPPAYG EEAFTYLCTA PGCATQTPVP     600
         610        620        630        640        650
601 VRLAGVGFES KIVDGGCFAP WDLEATGACI CEIPTDVSCE GLGAWVPTAP     650
         660        670        680        690        700
651 CARIWNGTQR ACTFWAVNAY SSGGYAQLAS YFNPGGSYYK QYHPTACEVE     700
         710        720        730        740        750
701 PAFGHSDAAC WGFPTDTVMS VFALASYVQH PHKTVRVKFH TETRTVWQLS     750
         760        770        780        790        800
751 VAGVSCWVTT EHPFCNTPHG QLEVQVPPDP GDLVEYIMNY TGNQQSRWGL     800
         810        820        830        840        850
801 GSPNCHGPDW ASPVCQRHSP DCSRLVGATP ERPRLRLVDA DDPLLRTAPG     850
         860        870        880        890        900
851 PGEVWVTPVI GSQARKCGLH IRAGPYGHAT VEMPEWIHAH TTSDPWHPPG     900
         910        920        930        940        950
901 PLGLKFKTVR PVALPRALAP PRNVRVTGCY QCGTPALVEG LAPGGGNCHL     950
         960        970        980        990       1000
951 TVHGEDVGAF PPGKFVTAAL LNTPPPYQVS CGGESDRASA GH........   1000
```

```
              10         20         30         40         50
              ..........  ..........  ..........  ..........  ..........
  1  MGARASVLSG GELDRWEKIR LRPGGKKKYK LKHIVWASRE LERFAVNPGL         50
              60         70         80         90        100
              ..........  ..........  ..........  ..........  ..........
 51  LETSEGCRQI LGQLQPSLQT GSEELRSLYN TVATLYCVHQ RIEIKDTKEA        100
             110        120        130        140        150
              ..........  ..........  ..........  ..........  ..........
101  LDKIEEEQNK SKKKAQQAAA DTGHSSQVSQ NYPIVQNIQG QMVHQAISPR        150
             160        170        180        190        200
              ..........  ..........  ..........  ..........  ..........
151  TLNAWVKVVE EKAFSPEVIP MFSALSEGAT PQDLNTMLNT VGGHQAAMQM        200
             210        220        230        240        250
              ..........  ..........  ..........  ..........  ..........
201  LKETINEEAA EWDRVHPVHA GPIAPGQMRE PRGSDIAGTT STLQEQIGWM        250
             260        270        280        290        300
              ..........  ..........  ..........  ..........  ..........
251  TNNPPIPVGE IYKRWIILGL NKIVRMYSPT SILDIRQGPK EPFRDYVDRF        300
             310        320        330        340        350
              ..........  ..........  ..........  ..........  ..........
301  YKTLRAEQAS QEVKNWMTET LLVQNANPDC KTILKALGPA ATLEEMMTAC        350
             360        370        380        390        400
              ..........  ..........  ..........  ..........  ..........
351  QGVGGPGHKA RVLAEAMSQV TNTATIMMQR GNFRNQRKMV KCFNCGKEGH        400
             410        420        430        440        450
              ..........  ..........  ..........  ..........  ..........
401  TARNCRAPRK KGCWKCGKEG HQMKDCTERQ ANFLGKICLP TREGQGIFFR        450
             460        470        480        490        500
              ..........  ..........  ..........  ..........  ..........
451  ADQSQQPHHF FRADQSQQPH QKRASGLG..  ..........  ..........         500
```

FIG. 4

```
        10         20         30         40         50
1   MRVKEKYQHL WRWGWKWGTW LLGILMICSA TEKLWVTVYY GVPVWKEATT    50

60         70         80         90        100
51  TLFCASDAKA YDTEVHNVWA THACVPTDPN PQEVVLVHVT ENFNMWKNDM   100

110        120        130        140        150
101 VEQMHEDIIS LWDQSLKPCV KLTPLCVSLK CTDLGNATNT NSSNTNSSSG   150

160        170        180        190        200
151 EMWMEKGEIK NCSFNISTSI RGKVQKEYAF FYKLDIIPID NDTTSYTLTS   200

210        220        230        240        250
201 CNTSVITQAC PKVSFEPIPI HYCAPAGFAI LKCNNKTFNG TGPCTNVSTV   250

260        270        280        290        300
251 QCTHGIRPVV STQLLLNGSL AEEEVVIRSA NFTDNAKTII VQLNQSVEIN   300

310        320        330        340        350
301 CTRPNNNTRK SIRIQRGPGR AFVTIGKIGN MRQAHCNISR AKWNATLKQI   350

360        370        380        390        400
351 ASKLREQFGN NKTIIFKQSS GGDPEIVTHS FNCGGEFFYC NSTQLFNSTW   400

410        420        430        440        450
401 FNSTWSTEGS NNTEGSDTIT LPCRIKQFIN MWQEVGKAMY APPISGQIRC   450

460        470        480        490        500
451 SSNITGLLLT RDGGNNNNGS EIFRPGGGDM RDNWRSELYK YKVVKIEPLG   500

510        520        530        540        550
501 VAPTKAKRRV VQREKRAVGI GALFLGFLGA AGSTMGARSM TLTVQARQLL   550

560        570        580        590        600
551 SGIVQQQNNL LRAIEAQQHL LQLTVWGIKQ LQARILAVER YLKDQQLLGI   600

610        620        630        640        650
601 WGCSGKLICT TAVPWNASWS NKSLEQIWNN MTWMEWDREI NNYTSLIHSL   650

660        670        680        690        700
651 IEESQNQQEK NEQELLELDK WASLWNWFNI THWLWYIKIF IMIVGGLVGL   700

710        720        730        740        750
701 RIVFAVLSIV NRVRQGYSPL SFQTHLPTPR GPDRPEGIEE EGGERDRDRS   750

760        770        780        790        800
751 IRLVNGSLAL IWDDLRSLCL FSYHRLRDLL LIVTRIVELL GRRGWEALKY   800

810        820        830        840        850
801 WWNLLQYWSQ ELKNSAVSLL NATAIAVAEG TDRVIEVVQG ACRAIRHIPR   850

860        870        880        890        900
851 RIRQGLERIL L.........                                    900
```

FIG. 5

```
            10         20         30         40         50
            ....|....|....|....|....|....|....|....|....|....|
  1  MKTTLKMTAL AALSAFVLAG CGSHQMKSEE HANMQLQQQA VLGLNWMQDS    50
            60         70         80         90        100
            ....|....|....|....|....|....|....|....|....|....|
 51  GEYKALAYQA YNAAKVAFDH AKVAKGKKKA VVADLDETML DNSPYAGWQV   100
           110        120        130        140        150
            ....|....|....|....|....|....|....|....|....|....|
101  QNNKPFDGKD WTRWVDARQS RAVPGAVEFN NYVNSHNGKV FYVTNRKDST   150
           160        170        180        190        200
            ....|....|....|....|....|....|....|....|....|....|
151  EKSGTIDDMK RLGFNGVEES AFYLKKDKSA KAARFAEIEK QGYEIVLYVG   200
           210        220        230        240        250
            ....|....|....|....|....|....|....|....|....|....|
201  DNLDDFGNTV YGKLNADRRA FVDQNQGKFG KTFIMLPNAN YGGWEGGLAE   250
           260        270        280        290        300
            ....|....|....|....|....|....|....|....|....|....|
251  GYFKKDTQGQ IKARLDAVQA WDGK......  ..........  ..........  300
```

FIG. 6

```
              10         20         30         40         50
      1 IQPPKNLLFS SLLFSSLLFS SAAQAASEDR RSPYYVQADL AYAAERITHD    50
              60         70         80         90        100
     51 YPQATGANNT STVSDYFRNI RAHSIHPRVS VGYDFGGWRI AADYASYRKN   100
             110        120        130        140        150
    101 NNNKYSVNTK ELENKHNNKK DLKTENQENG TFHAASSLGL SAIYDFKLKG   150
             160        170        180        190        200
    151 KFKPYIGARV AYGHVRHSID .......... .......... ..........   200
```

FIG. 9

```
              10         20         30         40         50
      1 MKVSAALLCL LLIAATFIPQ GLAQPDAINA PVTCCYNFTN RKISVQRLAS    50
              60         70         80         90        100
     51 YRRITSSKCP KEAVIFKTIV AKEICADPKQ KWVQDSMDHL DKQTQTPKT.   100
```

FIG. 10

```
              10         20         30         40         50
      1 KSTTCCYRFI NKKIPKQRLE SYRRTTSSHC PREAVIFKDK EICADPTQKW    50
              60         70         80         90        100
     51 VQDFMKHLDK KTQTPKL... .......... .......... ..........   100
```

FIG. 7

```
                                            -11        -1
                                        ..........
                                        ....KLMI*K              6
         10         20         30         40         50
     ..........  ..........  ..........  ..........  ..........
  7  FVTKM*YKTL  DKYLRRRLIL  NISIV*K*LS  EKR*I*MNKK  KMILTSLASV  56
         60         70         80         90        100
     ..........  ..........  ..........  ..........  ..........
 57  AILGAGFVAS  QPTVVRAEES  PVASQSKAEK  DYDAAKKDAK  NAKKAVEDAQ  106
        110        120        130        140        150
     ..........  ..........  ..........  ..........  ..........
107  KALDDAKAAQ  KKYDEDQKKT  EEKAALEKAA  SEEMDKAVAA  VQQAYLAYQQ  156
        160        170        180        190        200
     ..........  ..........  ..........  ..........  ..........
157  ATDKAAKDAA  DKMIDEAKKR  EEEAKTKFNT  VRAMVVPEPE  QLAETKKKSE  206
        210        220        230        240        250
     ..........  ..........  ..........  ..........  ..........
207  EAKQKAPELT  KKLEEAKAKL  EEAEKKATEA  KQKVDAEEVA  PQAKIAELEN  256
        260        270        280        290        300
     ..........  ..........  ..........  ..........  ..........
257  QVHRLEQELK  EIDESESEDY  AKEGFRAPLQ  SKLDAKKAKL  SKLEELSDKI  306
        310        320        330        340        350
     ..........  ..........  ..........  ..........  ..........
307  DELDAEIAKL  EDQLKAAEEN  NNVEDYFKEG  LEKTIAAKKA  ELEKTEADLK  356
        360        370        380        390        400
     ..........  ..........  ..........  ..........  ..........
357  KAVNEPEKPA  PAPETPAPEA  PAEQPKPAPA  PQPAPAPKPE  KPAEQPKPEK  406
        410        420        430        440        450
     ..........  ..........  ..........  ..........  ..........
407  TDDQQAEEDY  ARRSEEEYNR  LTQQQPPKAE  KPAPAPKTGW  KQENGMWYFY  456
        460        470        480        490        500
     ..........  ..........  ..........  ..........  ..........
457  NTDGSMATGW  LQNNGSWYYL  NSNGAMATGW  LQYNGSWYYL  NANGAMATGW  506
        510        520        530        540        550
     ..........  ..........  ..........  ..........  ..........
507  AKVNGSWYYL  NANGAMATGW  LQYNGSWYYL  NANGAMATGW  AKVNGSWYYL  556
        560        570        580        590        600
     ..........  ..........  ..........  ..........  ..........
557  NANGAMATGW  LQYNGSWYYL  NANGAMATGW  AKVNGSWYYL  NANGAMATGW  606
        610        620        630        640        650
     ..........  ..........  ..........  ..........  ..........
607  VKDGDTWYYL  EASGAMKASQ  WFKVSDKWYY  VNGLGALAVN  TTVDGYKVNA  656
        660        670        680        690        700
     ..........  ..........  ..........  ..........  ..........
657  NGEWV*AD*I  KAC*EHLTF*  F*NKDKVRLN  RFMFVFFRY.  ..........  706
```

FIG. 8

```
            10         20         30         40         50
  1 MNMKKATIAA TAGIAVTAFR APTIRSASTV VVEAGDTLWG IAQSKGTTVD    50

60         70         80         90        100
 51 AIKKANNLTT DKIVPGQKLQ VNNEVAAAEK TEKSVSATWL NVRSGAGVDN   100

110        120        130        140        150
101 SIITSIKGGT KVTVETTESN GWHKITYNDG KTGFVNGKYL TDKAVSTPVA   150

160        170        180        190        200
151 PTQEVKKETT TQQAAPAAET KTEVKQTTQA TTPAPKVAET KETPVVDQNA   200

210        220        230        240        250
201 TTHAVKSGDT IWALSVKYGV SVQDIMSWNN LSSSSIYVGQ KLAIKQTANT   250

260        270        280        290        300
251 ATPKAEVKTE APAAEKQAAP VVKENTNTNT ATTEKKETAT QQQTAPKAPT   300

310        320        330        340        350
301 EAAKPAPAPS TNTNANKTNT NTNTNTNTNN TNTNTPSKNT NTNSNTNTNT   350

360        370        380        390        400
351 NSNTNANQGS SNNNSNSSAS AIIAEAQKHL GKAYSWGGNG PTTFDCSGYT   400

410        420        430        440        450
401 KYVFAKAGIS LPRTSGAQYA STTRISESQA KPGDLVFFDY GSGISHVGIY   450

460        470        480        490        500
451 VGNGQMINAQ DNGVKYDNIH GSGWGKYLVG FGRV......  ..........  500
```

1  2/3  4/5/6  7/8  9/10

1  2  3  4/5  6/7

1  2  3/4

ANTIBODIES WHICH BIND MENINGITIS RELATED HOMOLOGOUS ANTIGENIC SEQUENCES

FIELD OF THE INVENTION

This invention relates to the application of immunological techniques that provide novel materials useful in the diagnosis, treatment and vaccination against meningitis caused by either bacterial or viral agents. These techniques include the production and application of novel monoclonal antibodies, peptides, and mixtures and combinations thereof that are useful for detecting meningitis infections. The techniques also include eliciting antibodies specific to meningitis causing agents. These immunological techniques may also be applied to the treatment of such disease.

BACKGROUND OF THE INVENTION

The term meningitis is a general one, referring to the inflammatory response to infection of the meninges and the cerebrospinal fluid (CSF). See Roos, "Chapter 16", in Scheld, et al. eds., 1991, *Infections of the Central Nervous System*:335–403 which is incorporated herein in its entirety by reference.

The fact that the inflammatory response occurs in the proximity of the brain and in the space limited by a rigid cranium, makes these infections serious and life threatening. Most patients exhibit nonspecific clinical signs and symptoms such as fever, irritability, altered mental status usually accompanied by vomiting and loss of appetite. In children one year of age and older, photophobia and headache are common complaints. Specific clinical signs indicative of meningitis are neck rigidity and pain on neck flexion. Brudzinski's sign (neck flexion producing knee and hip flexion) and Kernig's sign (difficulty and pain in raising extended leg) are other useful clinical signs.

In infants less than 6 months old, early diagnosis of meningitis is difficult because signs of meningitis are not prominent and neck rigidity is often absent. Such patients commonly exhibit fever, respiratory distress, other signs of sepsis, and convulsions. Bulging anterior fontanelle due to increased intracranial pressure may be the only specific sign.

Petechiae (or rash) is most commonly present in meningococcal infections. In severe meningococcal infections with bacteraemia, petechiae and shock may develop with alarming rapidity. Convulsions at some point in the illness occur in about 30% of the cases. This number is often higher in neonates and infants under one year of age. Other acute complications include septic shock, disseminated intravascular coagulation, syndrome of inappropriate antidiuretic hormone, increased intracranial pressure, and diabetes insipidus. Convulsions and coma appearing with 24 hours accompanied by high fever indicates serious infection (Stutman & Marks, 1987, *Clin. Ped.* 26:432–438).

A diverse array of both bacteria and viruses cause meningitis, the infectivity of which is dependent on a complex array of factors, including virulence of the organisms, the carrier state, and the host's humoral immune response.

Viruses generally cause milder forms of meningitis (eg. meningomyelitis and aseptic meningitis) with a short clinical course and reduced mortality. Agents most commonly associated are coxsackievirus A (types 2,4,7,9,10), B (types 1–6), polio virus, echoviruses (types 1–34, except 12,24,26, 29,32–34), enteroviruses (types 70, 71), human immunodeficiency virus-1 (HIV-1), and rubella virus (RV). See Melnick, "Chapter 33" and Cooper, "Chapter 42" in Fields, et al., eds., 1985, *Virology*: 739–794 and 1005–1032, respectively; and Rotbart, "Chapter 3", in Scheld et al., 1991, infra:19–33 which are all incorporated herein by reference.

Rubella is possibly the most common cause of viral meningitis. Moreover, the most common chemical sequelae of rubella infection of young children are meningitis, meningomyelitis and rubella associated panencephalitis. Rubella is a highly contagious disease, usually associated with childhood, and is characterized by a general rash and a mild fever. Sub-clinical infections are also common. Its clinical aspects have been confused with measles, which it closely resembles. Since its early discovery in Germany, Rubella is often referred to as German measles. The infection of a pregnant woman poses the greatest risk when infection of the fetus can lead to spontaneous abortion or an array of abnormalities called the Congenital Rubella Syndrome in the newborn. Damage most frequently involves cardiac abnormalities, deafness, cataracts, blindness and Central Nervous System (CNS) disorders including microencephaly.

The rubella virion is a spherical, enveloped virus, approximately 60 nm in diameter, and is a member of the Togaviridae. It's genome is a 10 Kb plus single-stranded RNA. The outer envelope is comprised of lipoproteins derived from the infected host cell, and it appears to have two viral encoded glycoproteins, E1 (58 Kd) and E2 (42–47 Kd), responsible for the hemagglutination activity of the virus. Its core protein is a non-glycosylated nucleocapsid protein with an approximate weight of 33 Kd. It appears that the core, E1, and E2 are all derived from the same parent protein—Structural Polyprotein. See Clark et al., 1987, *Nucl. Acids Res.* 15:3041–3057; Dominguez, et al., 1990, *Virology* 177:225–238, both which are incorporated herein by reference. Three strains of wild type RV (M33, Therien, Judith) and a vaccine strain (HPV77) of RV have been identified and sequenced (Zheng et al., 1988, *Arch. Virol.* 98:189–197 incorporated herein in its entirety by reference). Between these different wild types strains, there exists minor variations in the amino acid sequence of the Structural Polyprotein (Dominguez, infra; Clarke, infra).

The detection of RV in diagnosis has in the past proven difficult, largely because the virus grows to low titers in the tissue cultures and is highly liable, making it technically difficult to isolate and purify (Ho-Terry et al., 1986, *Arch. Virol.* 87: 219–228).

The detection of RV in the CNS presents additional technical problems. It has been known since 1941 that the RV can infect cells of the CNS (Gregg, 1941, *Trans. Ophthalmol. Soc. Aust.* 3:35– 46). However, it has proven difficult to reliably demonstrate the presence of the RV in infected brain tissue. Persistent infection of the CNS has been well documented in the congenital rubella syndrome (Desmond et al., 1967, *J. Pediat.*, 7:311–331), and in the neuropathology if progressive rubella panencephalitis of late onset occurs where the virus has been isolated from brain biopsy material (Townsend et al., 1975, *N. Engl. J. Med.* 292:990–993; Cremer et al., 1979, *J. Gen. Virol.* 29:143–153). Less commonly documented are the wide range of neuropathies known to follow exposure to the RV. These include encephalitis, meningomyelitis, and bilateral optic neuritis (Connolly et al., 1975, *Brain* 98:583–594). Moreover, the report of a diffuse myelitis following RV in cells of the nervous system requires further investigation (Holt et al., 1975, *Brit. Med. J.*, 7:1037–1038).

RV-directed polypeptide synthesis in normal rat glial cells in continuous tissue culture has been studied (Singh & Van Alstyne, 1978, *Brain Res.* 155:418–421). Unlike a productive rubella virus infection in permissive murine L (muscle) cells, infection of normal glial cells resulted in no detectable progeny virons in tissue culture supernatants and no detectable rubella 33 Kd core protein in infected cell lysates (Pope and Van Alstyne, 1981, *Virology* 124:173–180). Furthermore, exposure of infected gila to dibutyryl cyclic adenine monophosphate reversed the restriction, resulting in the appearance of the 33 Kd rubella nucleocapsid protein in infected cell lysates and the appearance of mature progeny virions in tissue culture supernatants (Van Alstyne and Paty, 1983, *Virology* 124:173–180).

Others have reported a lack of synthesis of the structural M protein in measles virus-infected brain cells obtained from subacute sclerosing panencephalitis autopsy material established in tissue culture (Hall and Choppin, 1979, *Virology* 99:443–447). Also, it is known that the incomplete synthesis of some Herpes specific structural proteins occurs during a nonpermissive infection of some cells of nervous system origin (Adler et al., 1978, *J. Gen. Virology* 39:9–20).

Taken together, these data indicate that even very different viruses may undergo restricted replication in brain cells. The synthesis of a limited number of viral gene products could account for incomplete virion assembly, the translation of polypeptides of variable molecular weights, alterations in the immune response to input virus, and difficulties in successful virus isolation from infected brain tissue.

Therefore, there remains a need for a diagnostic system which would detect RV protein antigens in CNS tissue in both the presence as well as the absence of an active, productive infection.

Early diagnostic tests were based on the hemagglutinating properties of its external glycoproteins. Commonly, the hemagglutination inhibition assays relied on the presence of antibodies to the RV hemagglutinin (HA) in the serum samples to inhibit the viral-mediated hemagglutination of chick red blood cells (Herrmann, "Rubella Virus", 1979, in *Diagnostic Procedures For Viral, Rickettsial And Chlamydial Infections*:725–766). The presence of high inhibition, indicated the indirect measurement of antibodies to the HA protein, and thereby, a recent rubella infection.

More recent tests employ enzyme-labelled antibodies in the enzyme-linked-immunosorbent assays (ELISA) (Voller & Bidwell, 1975, *Br. J. Exp. Pathol.* 56:338–339 incorporated herein by reference). These assays are also indirect tests to measure the amount of circulating antibody to RV as an indication of infection. Indirect ELISA tests for RV employ bound viral antigens on a plastic microwells and the presence of bound antibodies linked to enzymes such as horseradish peroxidase.

There are several problems with the use of the indirect RV ELISA kits. These relate to low antibody titers observed with RV infection, the need for elaborate "cut-off" value calculations to eliminate background binding, the limited use of the test in the detection of low levels of specific viral antigens present in chronic CNS infection, and the tedious and time consuming nature of the test performance.

A different use of monoclonal antibodies and their corresponding synthetic peptide epitopes may prove more useful in detecting RV infection in the CNS. There has been discussion that refers to the use of three non-competing monoclonal antibodies directed against the E1 glycoprotein, but this system has not been applied to CNS-specific diagnostics (Terry et al., 1988, *Arch. Virol.* 98, 189–197 incorporated herein by reference).

Therefore, there is clearly a need for a rapid and a sensitive diagnostic test for the detection of the RV in CNS infection.

Furthermore, a live, attenuated rubella vaccine has been developed (Parkman et al., 1966, *N. Engl. J. Med* 275: 569–574). This vaccine is immunogenic in at least 95% of the recipients, and does confer protection against reinfection, in spite of the fact that it induces antibody levels which are significantly lower than those generated by wild type virus infection. However, a serious drawback associated with the administration of the attenuated vaccine is the significant proportion of adult females that go on to develop rubella-associated arthritis. Furthermore, recently immunized individuals still harbour infectious virus and are therefore infectious, proving dangerous to pregnant women with whom they may be in contact.

Therefore, there is also a need for a non-infectious, innocuous vaccine. Such a vaccine could possibly be constructed from synthetic or recombinant peptides of RV proteins. Moreover, no epitope has yet been identified which would induce only neutralizing antibodies, necessary for conferring effective vaccine protection.

Another virus responsible for meningitis is the Human Immunodeficiency Virus-1 (HIV-1). HIV-1 is a human retrovirus which has been identified as the etiological agent of AIDS, an infectious and fatal disease transmitted through intimate sexual contact and exposure to contaminated blood or blood products. HIV-1 is related to the lentiviruses on the basis of its biological and in vitro characteristics, morphology and nucleotide sequences. It is also referred to as Human T-cell Lymphotrophic Virus type III, Lymphadenopathy Associated Virus, and AIDS Associated Retrovirus (Gallo, et al., 1984, *Science*, 224:500–503; Sarngadharan, et al., 1984, *Science*, 224:506–508; Barre-Sinoussi, et al., 1983, *Science*, 220:868–871; Levy, 1984, *Science*, 225:840–842; Gonda et al., 1985 *Science*, 227:177–179; Stephan, et al., 1986, *Science*, 231:589–594). Much interest has been focused on the effect of the long term, persistent infection of the immune system, by HIV-1. Recent information indicates that the virus moves from blood to the lymph nodes and thymus where it remains active, culminating in viremia, a precipitous drop in the CD4+ T-cell count, and one or more of the several symptoms known as AIDS.

However, primary HIV-1 infection itself results in an immediate set of defined clinical features. Commonly, an acute febrile illness resembling influenza or mononucleosis is noted. In addition, lymphocytic meningitis may accompany the febrile illness and the patient may then be presented with headache, stiff neck and photophobia, as well as rigors, arthralgias and myalgias, truncal maculopapular rash, urticaria, abdominal cramps and diarrhea (Ho, 1985, *Ann. Internal Medicine* 103:880–883).

While some patients remain asymptomatic for up to 3 months preceding their seroconversion, indicating that HIV-1 infection may be subclinical, primary infection should be included in the differential diagnosis of prolonged febrile illnesses in persons at risk for AIDS. The presence of a maculopapular or urticarial rash, or lymphocytic meningitis is compatible with this diagnosis. Hence, early recognition of the varied syndromes associated with this virus might permit effective treatment before immunologic abnormalities become established.

There is, therefore, the need for a rapid, direct diagnostic test for viral meningitis, prior to seroconversion, when the transient meningitis may represent the initiation of a more serious, long term HIV-1 related illness.

Currently, one of the most commonly used direct tests for HIV-1 infection employs the following approaches: (i) direct culturing of virus from infected blood or blood cells and subsequent in vitro propagation of the virus in lymphocyte cultures; (ii) measuring reverse transcriptase levels; (iii) immunocytochemical staining of viral proteins; (iv) electron microscopy; (v) hybridization of nucleic acid probes; and measuring HIV-1 antigens with enzyme immunoassays (Goudsmit et al., 1986, *Brit. Med. J.,* 2993:1459–1462; Caruso et al., 1987, *J. Virol. Methods,* 17:199–210).

The HIV-1 appears to have at least three core protein (p17, p24, and p15) that are derived from a core polyprotein called gag polyprotein. See Muesing, et al., 1985, *Nature* 313:450–458 incorporated herein by reference. The gag polyprotein in the LV isolate of HIV-1 is 478 amino acids long and the three mature core proteins appear to be derived as p17 from amino acid sequence numbers 1–132, p24 from amino acid sequence numbers 133–391, and p15 from amino acid sequence numbers 392–478 (Muesing, infra). Moreover, it appears that the HIV-1 (LAV-1a isolate) also has at least one capsid transmembrane glycoprotein derived from a 861 amino acid long Envelope Polyprotein (Wain-Hobson, et al., 1985, *Cell* 40:9–17 incorporated herein by reference).

The enzyme immunoassays have clearly shown the diagnostic importance of the presence of the p24 core protein. A correlation has been established between viremia, the decline of antibodies to p24, and the progression of symptoms from the asymptomatic seropositivity to fully expressed AIDS (Lange et al., 1986, *Brit. Med. J.,* 293:1459–1462; Paul et al., 1987, *J. Med. Virol.,* 22:357–363; Forster et al., 1987, *AIDS,* 1:235–240). A decline in the p24 level has also been observed to occur in patients treated with AZT (Chaisson et al., 1986, *New Eng. J. Med.,* 315:1610–1611).

Assays for the direct detection of p24 are currently on the market (Forster, infra). These assays use the same sandwich format in which serum samples are incubated with bound and enzyme-labelled anti-p24-antibodies to form an antibody/p24 -antigen-antibody sandwich. Antigen levels of approximately 50 picograms/ml can be detected, when the antigen concentration is read from a standard curve constructed with a set of p24 standards of known concentrations. The tests are tedious and time consuming to perform, require dilutions of patients' sera, and do not provide information regarding the comparisons of rising antigen and concomitant declining antibody levels necessary to evaluate laboratory findings.

Therefore, the need to rapidly and effective diagnostic test to screen large numbers of a symptomatic individuals for the presence of HIV-1 virus in individuals is clear.

There is also an urgent need for a vaccine to afford protection against transmission of AIDS by individuals who are not detected by current diagnostic tests.

However, there are significant difficulties inherent in designing a vaccine which will confer protection against HIV-1. The vaccine must differentiate between HIV-1 and the closely-related virus, HIV-2. The rapid rate of HIV-1 mutation requires that the antigen(s) be highly conserved. Moreover, the HIV-1 infection of a small subset of T cells requires the killing of an integral part of the immune cell network, with unknown consequences, to completely eradicate the virus. In addition, vaccinated antigens could enter lymph nodes and stimulate B cells to produce cytokines that in turn stimulate HIV-1 infection of T cells, and thereby having a reverse effect, causing a more rapid onset of AIDS.

Peptides from gp120, gp160, gp41, gp120 +gp41, p17 and p14 are currently being employed for vaccine production by several companies and universities (Spalding, 1992, *Biotech.* 10:24–29.) However, these peptides are being tested for their ability to solely induce B cells to produce neutralizing antibody.

Therefore, there is an urgent need for the selection of HIV-1 peptides which would serve as appropriate B cell stimulators, to produce protective, neutralizing antibody, as well as appropriate cytokine blockers to prevent HIV-1 infection of T-cells. To date, no known combination of such peptides has been shown to protect against AIDS infection.

Bacteria are the other major cause of meningitis. Approximately 70% of all cases of bacterial meningitis occur in children under the age of 5 years; three bacterial species cause 84% of all meningitis cases reported in the United States: *Haemophilus influenza* type B, and *Streptococcus pneumoniae* and *Neisseria meningitidis* (Roos, infra; Stutman, infra). Less prevalent bacterial species include *Pseudomonas aerugensosa,* Staphylococci, Mycobacteria and Listeria species.

All strains of *Haemophilus influenzae* (*H. influenza*) are divided into two groups: typeable strains which commonly have a capsule, and nontypeable strains which do not. Typing of the encapsulated strains is accomplished by serological techniques, using reference antisera. Types a to f have been identified in this way. Those strains which fail to react with any of the reference antisera are classified as nontypeable.

The most frequent cause of neonatal meningitis and other invasive infections in the United States is the encapsulated *H. influenzae* type b (Hib) (Fraser et al., 1974, *Am. J. Epidemiol,.* 100:29–34). While the major incidence of childhood meningitis occurs between the ages of one and five years, 60% of the meningitis cases due to Hib occur in children under the age of two years.

The nontypeable *H. influenzae* are known to cause meningitis, pneumonia, bacteraemia, postpartum sepsis, and acute febrile tracheobronchitis in adults (Murphy et al., 1985, *J. Infect. Diseases,* 152:1300–1307). About 20 to 40% of all cases of otitis media are caused by this *H. influenzae,* which is a frequent etiologic agent of otitis media in children and young adults. Since infection confers no long lasting immunity, repeated infections of the same organism is frequently observed. These chronic ototis media infections are treated by administration of antibiotics, and drainage of the inner ear, where such a procedure is deemed necessary. *H. influenzae* strains have also been implicated as a primary cause of sinusitis (Cherry & Dudley, 1981, in Feigin & Cherry eds., *Textbook of Pediatric Infectious Diseases:*103–105). Nontypeable *H. influenzae* are also known to cause neonatal sepsis.

A vaccine is currently available for protection against typeable *H. influenzae,* and employs the capsular polysaccharide antigen of Hib, polyribosyl ribitol phosphate (Smith et al., 1973, *Pediatrics,* 52:637–644; Anderson et al., 1972, *J. Clin. Inv.,* 51:31–88). However, Anti-PRP antibody is not effective in conferring protection against non-typeable *H. influenzae* infection. Thus, all available vaccines against *H. influenzae* are all directed against Hib, and all elicit anti-PRP antibody to confer protection. Since the non-typeable *H. influenzae* lack the PRP capsule, no vaccine is efficacious against this group.

However, there does appears that *H. Influenzae* exhibits an outer membrane lipoprotein referred to as p4 (Green, et al., 1992, EMBL Bank, incorporated herein by reference). The p4 protein appears to be derived from the Lipoprotein E Precursor, the precursor protein being 274 amino acids in length (SEQ ID NO: 17).

There is therefore a clear need for both a method of diagnosis for this disease as well as a vaccine which would protect against both typeable as well as nontypeable *H. influenzae*. It is possible that the p4 lipoprotein providing a source for such a vaccine.

*Streptococcus pneumoniae* is the leading cause of community-acquired bacterial pneumonia (pneumococcal diseases), with approximately 500,000 cases a year reported in the United States. Bacterial pneumonia is most prevalent among the very young, the elderly and immuno-compromised persons. In infants and children, pneumococci are the most common bacterial cause of pneumonia, otitis media and bacteraemia and a less common cause of meningitis (causing 20-25% of reported cases).

Pneumococci are carried in the respiratory tract of a significant number of healthy individuals. But, in spite of the high carriage rate, its presence does not necessarily imply infection. However, if one of the highly pathogenic pneumococcal types, such as *S. pneumoniae*, is isolated from rusty-colored sputum (also containing a large number of polymorphonuclear leucocytes), body fluids, blood cultures, or specimens collected via transtracheal or lung puncture from the lower respiratory tract, its detection is usually significant.

*S. pneumoniae* is a gram positive bacteria. Proteins located on the cell surface of many gram positive bacteria are frequently involved in virulence and host immunity and have, in the past, been used in typing these bacteria and in immunoprotection studies. There are a large number of *S. pneumoniae* strains, classified into serotypes based on their surface carbohydrate structures. There are also many cell surface proteins associated with *S. pneumoniae*. Surface proteins that exhibit antigenic variation (by antigenic shirt or drift) make the identification of a common but exclusive cell surface antigen difficult and may provide the organism with an additional mechanism for evading the host immune response.

Detection of this bacteria at an early stage is essential to facilitate treatment of the infection. Thus, it is important to be able to quickly identify whether *S. pneumoniae* is present in a patient and to be able to follow the effect of antibiotic treatment on the bacteria. As available immunoassays for *S. pneumoniae* antigen detection are deficient for lack of specificity and/or sensitivity, there remains the need for an improved method of such detection.

Monoclonal antibody (Mab) technology has recently provided researchers with tools to reproducibly and accurately analyze the cell surface components of *S. pneumoniae*. Hence *S. pneumoniae* proteins are of interest to epidemiologists as they may provide a method of detection as well as for vaccines against the bacteria.

One such cell surface protein is *Streptococcus pneumoniae* pneumonococcal surface protein A (pspA) (Yother, 1992, *J. Bacteriol.* 174:601–609 incorporated herein by reference). The complete sequence of this protein is known.

It is known that one such pneumonococcal vaccine has been developed which incorporates the capsular polysaccharide antigens of 23 prevalent serotypes of pneumococci. These serotypes are responsible for 87% of pneumococcal disease in the United States. This second generation vaccine replaced a 14-valent polysaccharide vaccine available since 1977. However, the U.S. Department of Health and Human Services has stated that a more immunogenic pneumococcal vaccine is needed, particularly for children younger than 2 years of age. This necessity exists because the 23-valent vaccine is poorly immunogenic in this age group. Consequently, the use of the vaccine is not recommended in children with recurrent upper respiratory diseases, such as otitis media and sinusitis. Furthermore, the 23-valent vaccine is only 44–61% efficacious when administered to persons over 65 years old, and revaccination is not advised. Thus, there remains a clear need for an improved pneumococcal vaccine.

*Neisseria meningitis* (*N. Meningitis*) is one of the leading causes of community-acquired bacterial meningitis, causing 10.3% of cases in the United States between 1978–1981 (Tunkel et al., 1990 *Annals of Internal Medicine*, 112: 610–623). Meningococcal meningitis is most prevalent among infants between 6–12 months and adolescents (Larter & Master, 1992, *Am. J. Med.—Infectious Disease Symposium:*120–123). In addition to meningococemia, other less commonly associated diseases such as conjunctivitis, sinusitis, endocarditis, and primary pneumonia can occur (Duerden, 1988, *J. Med. Microbiol.*, 26:161–187).

*N. meningitidis* bacterium are carried in the nasopharynx of 10–15% of healthy individuals. In spite of the high carriage rate, its presence does not necessarily imply infection. However, isolation of *N. meningitidis* from cerebral spinal fluid or blood culture is significant (Stutman, infra; Mendelson & Dascal, 1992, *Can. J. of Diag.*, 9:47–57; Martin, 1983, *Am. J. Med.:*120–123).

*N. meningitidis* is a gram negative bacteria. Proteins located on the cell surface of many gram negative bacteria have, in the past, been used in typing and immunoprotective studies. There are a large number of *N. meningitidis* strains and there are many cell surface proteins associated with *N. meningitidis*. This has made identification of a common but exclusive cell surface antigen difficult.

Detection of this bacteria at an early stage is essential to facilitate treatment of the infection (Stutman, infra). Thus, it is important to possess the ability to identify whether *N. meningitidis* is present in a patient and to follow the effect of antibiotic treatment on the bacteria. As available immunoassays for *N. meningitidis* antigen detection have shown lack of specificity and/or sensitivity, there remains the need for an improved method of such detection.

As Mab technology has recently provided researchers with tools to accurately analyze the cell surface components of this bacteria, *N. meningitidis* proteins are of interest to the epidemiologists as they may provide for a new method of detection as well as a vaccines against it.

One such cell surface protein is the Opacity-Related Protein POPM3 (Stern, 1987, *Mol. Microbiol.* 1:5–12 incorporated herein by reference). The complete sequence of this 170 amino acid protein is known.

Most meningococcal vaccines have been developed using capsular polysaccharides. One particularly quadravalent vaccine incorporates polyssacharide antigens of serogroups A, C, W and Y, meningococci. However, these serogroups are responsible for less than 49% of meningococcal disease in the United States. No capsular polysaccharide vaccine is available for serogroup B *N. meningitidis*, which is the most prevalent serogroup, since it is poorly immunogenic. Moreover, polyssacharide vaccines are poorly immunogenic in infants because they are T lymphocyte independent antigens which are inefficient at inducing an immunologic memory. Furthermore, no cross protection between serogroups occurs. Thus, there remains the need for an improved meningococcal vaccine.

It follow then, that there remains a need for at least two products relating to *N. meningitidis*. The first being a rapid, specific, and sensitive diagnostic test for all strains of *N.*

*meningitidis,* that does not give false positive results. What is optimally desired is a Mab that will recognize a cell surface antigen that is universally present in most, if not all, strains of *N. meningitidis,* and, at the same time does not recognize other non-meningitidis causing organisms or material which may be found in conjunction with *N. meningitidis*. Secondly, it is desirous that the Mab and said protein be used in research towards development of an improved vaccine.

In addition the three major causes of bacterial meningitis, there are other bacterial agents responsible for the disease. One such agent is *L. monocytogenes,* a motile, gram positive, rod-shaped microorganism belonging to the genus Listeria. This genus is widely distributed in nature-found in soil, water, vegetation and many animal species. See Bille & Doyle, 1990, "Listeria and Erysipelothrix" in Burbert, et al., *Manual of Clinical Microbiology* 5th ed.:231 which is incorporated herein by reference. Two Listeria species, *L. murrayi* and *L. grayi,* are rarely isolated and are presently considered nonpathogenic. However, five other species are genomically related and include three hemolytic species (*L. monocytogenes, L. seeligeri* and *L. ivanovii*) and two non-hemolytic species (*L. innocua,* and *L. welshimeri*). Of these, only *L. monocytogenes,* and sometimes *L. ivanovii* are human pathogens. *L. ivanovii* is mostly pathogenic for animals (Bille, infra).

*Listeria monocytogenes* is a facultative intracellular pathogen, capable of growth both in the external environment and inside mammalian cells. It is responsible for opportunistic infections in both humans and animals. The first cases of human listeriosis were reported in the 1930s and outbreaks have been traced to the consumption of contaminated food, most notably dairy and poultry products (Goebel et al., 1991, *Infection* 19:5195–5197). Individuals at risk are the newborn, the elderly, and the immunocompromised.

Clinical features of the diseases are meningitis and meningoencephalitis. Infection with *L. monocytogenes* has also been observed as septicemia (with resulting abortion) in pregnant women, and patients with malignancies and immunosuppression. Some people, usually predisposed by an underlying cardiac illness, have been treated for endocarditis resulting from listerial infection.

Although *L. monocytogenes* is considered an uncommon adult pathogen, it is the third most common cause of bacterial meningitis in neonates (McKay & Lu, 1991, *Infection & Immun.* 59:4286–4290). Highest mortality and neurological sequelae among survivors is seen when the central nervous system is involved. However, underlying conditions which cause lower cell-mediated immunity, such as transplants, malignancy and AIDS, can result in increased mortality, up to 60%.

There has been a gradual increase in the incidence of human listeriosis since the 1960s. Presumably, this is related to the increased numbers of individuals with malignancies undergoing radiation and chemotherapy, which allows for their prolonged survival but with immunosuppression as their consequence. Similarly, increases in renal transplantations has exposed increasing numbers of patients to possible infectious complications. Finally, with the rapid spread of AIDS and its suppression of immune function, it can be expected that the occurrence of human listeriosis may increase substantially in the future years.

The epithelial cells of the gastrointestinal tract may be the primary site of entry of *L. monocytogenes*. It was discovered in the 1960s that this bacterium can invade, survive and replicate within phagocytic cells, such as macrophages and monocytes (Michel & Cossart, 1992, *J. Bacteriol.* 174:7098–7103 incorporated herein by reference). Nonprofessional phagocytes, which are unable to take up extracelluarly growing bacteria, are also susceptible to invasion by this intracellular organism (Bubert et al., 1992, *J. Bacteriol.* 174:8166–8171 incorporated herein by reference). Apparently, *L. monocytogenes* is able to induce its own phagocytosis in these host cells. Specific virulence factors are required for this invasion and intracellular growth.

A major extracellular protein P60, named for its relative molecular weight of 60,000 daltons, is produced by all virulent *L. monocytogenes* strains. Protein P60 is derived from the Protein P60 Precursor also known as the invasion-associated protein (iap) as described by Koehler, et al., 1990, *Infect. Immun.* 58:1943–1950 incorporated herein by reference. Moreover, the precursor protein is 484 amino acids in length and the sequence is known (SEQ ID NO: 26).

Spontaneously occurring mutants of *L. monocytogenes* that show a decreased level of the protein P60, known as R mutants, are avirulent and unable to invade nonprofessional phagocytes. R mutants are still phagocytized by macrophages with the same efficiency as wild-type bacteria and are able to replicate in these cells. Addition of partially purified P60 protein from wild-type *L. monocytogenes* restores the invasiveness of these R mutants into nonprofessional phagocytic cells. This finding has led to the conclusion that P60 is involved in the mechanism of uptake of *L. monocytogenes* (SEQ ID NO: 26) by nonprofessional phagocytic cells.

The P60 protein of *L. monocytogenes* is 484 amino acids long, contains a putative N-terminal signal sequence of 27 amino acids and an extended repeat region of 19 threonine-asparagine units. The middle portion of the protein P60, consisting of about 240 amino acids, and located about 120 amino acids from both the N- and C- terminal ends, varies considerably from the deduced amino acid sequences of the related P60 proteins of *L. innocua, L ivanovii, L seeligeri, L welshimeri* and *L grayi.* From the predicted secondary structure and hydropathy studies on this protein, the hydrophillic middle portion consists of two alpha-helical regions flanking the repeat domain. Conversely, the hydrophobic N- and C- terminal ends are in predominantly B-pleated sheets. This would suggest that the middle region is exposed on the protein's surface (Kohler, infra).

The CSF findings in *Listeria meningitis* are quite variable and often result in a negative gram stain. This means that confirmed diagnosis is dependent on culture of either blood or CSF samples, which may take up to 48 hours. Given its high mortality and morbidity, and the increasing numbers of populations at risk, it is apparent that the need exists for rapid diagnosis and for a vaccine against *L. monocytogenes* infections.

It is a well known feature of bacterial and viral meningitis etiological agents that they possess the ability to infect the CNS. Until recently, it was not known how these agents could pass the Blood-Brain Barrier. The mechanism by which circulating bacteria enter the CSF compartment has only recently been understood. Circulating organisms could invade the CSF compartment by translocation through or between vascular endothelial cells and underlying tissues before entering the CSF. In fact, vascular lesions are a feature of meningitis caused by such organisms as *Salmonella choleraesuls* and *Pasteruella haeloytica.* See Wildock, 1977, *Vet. Pathol* 14:113–120; Sullivan, "The Nervous System: Inflammation", in Jubb et al., eds., 1985, *Pathology of Domestic Animals,* Volume 1:278–290 all of which are incorporated herein by reference.

However, while vascular endothelial damage may be integral to the pathogenic pathway for some bacteria, it is unlikely to be the mechanism of entry for most cases of meningitis, since vascular lesions are not a prominent early feature of meningitis caused by either N. meningitidis, S. pneumoniae, E coli, S. suls, H. parasuis, H. influenzae, or S. aureus (Williams, 1990, J. Infec. Dis., 162:474–481).

It has been shown that bacteria can be carried into the CSF in association with monocytes migrating into the CSF compartment to maintain populations of resident macrophages (Cordy, 1984, Vet. Pathol. 21:593–597). This method of entry for bacteria is also analogous to the mechanism employed by some viruses (HIV, Maaedi-Visna-caprine arthritis encephalitis virus) when invading the CNS. See Peluso, 1985, Virology 147:231–236; Narayan, 1985, Rev. Infec. Dis. 7:899–98; Roy, 1988, J. Leukoc. Clol. 43:91–97; Westervelt, 1991, Vaccines 91:71–76 which are all incorporated herein by reference.

It is also known art that cellular immune reactions consist of a complex series of coordinating events. In response to tissue injury, monocytes are recruited from bone marrow via the blood circulation (Robinson, 1989, PNAS 86:1850–1854 incorporated herein by reference). These activated blood monocytes then differentiate into macrophages in response to several immune mediators produced at the site of inflammation (Yoshimura, et al., 1989, FEBS Letter 244:487–493).

As macrophages normally function to protect the body from potentially toxic substances, either infectious or chemical in nature, they serve as scavengers, processing and presenting antigen to the B lymphocytes, which in turn produce antibodies. (Edington, 1993, Bio/Technology 11:676–681 incorporated herein by reference), Macrophages and also known to secrete mediators that mediate systemic host defence responses and local inflammation.

The first evidence of mediators being involved in cellular immune reactions was noted in 1970 (Ward, 1970, Cell Immunol., 1:162–174). It was reported that addition of antigen to specifically sensitized lymphocytes caused release of an "activity" which attracted macrophages (Robinson, infra). It is now well known that immune mediators possess a variety of functions for cytokines such as the interleukins and interferons.

This led the recent discovery of a family of small, secretory cytokine-like proteins called chemokines for their apparent chemotactic properties, whose complete proinflammatory functions have yet to be elucidated. However, the size and amino acid sequence of many of these chemokines is known as illustrated in Michiel, 1993, Bio/Technology 11:739, incorporated herein in its entirety by reference.

Like most secreted proteins, the chemokines are synthesized with a hydrophobic leader sequence which is cleaved to produce the mature, active chemokine. Comparison of their amino acid sequences has shown these proteins to have a highly conserved pattern of four cysteine residues in the mature peptides. Consequently, they have been classified into two groups based on their structural characteristics: the alpha chemokine group having an intervening amino acids between cys-1 and cys-2, (ie. a C—X—C motif); the beta chemokine group has no intervening amino acid, (ie. a C—C motif). (Michiel, 1993). Cys-1 crosslinks with Cys-3 and Cys-2 crosslinks with Cys-4, resulting in a similar tertiary structure for all the proteins classified into this family of chemokines.

It is further known that the chemokines appear to be functionally involved in cell chemotaxis. Their amino acids sequence diversity suggests that each chemokine has distinct cellular specificity, each having its own unique cellular targets.(Michiel, infra). This cellular specificity appears related to seven transmembrane-domain receptors in each chemokine, but the overlapping pattern of ligand binding and their regulation has yet to be determined (Rollins, et al., 1989, Molecular & Cellular Biol. 9:4687–4695 incorporated herein by reference).

Several peptides from the beta chemokine family have been found to possess the ability for "chemo-attracting" monocytes/macrophages. One such chemotactic protein was identified in 1978 in antigen-stimulated human lymphocytes. (Robinson, infra) and was named LDCF, for Lymphocyte-Derived Chemotactic Factor. This particular chemokine has since been isolated from a variety of different glioma cell lines; human peripheral blood mononuclear leukocytes, (Yoshimura, infra); resting human monocytes (Rollins, infra); human lung fibroblasts and a primary human fetal fibroblast cell line. This latter line being the only member of the Beta family of chemokines to be identified in fibroblasts.

As with all chemokines, various names have been used to identify this protein. The following terms are therefore interchangeable for those skilled in the art: GDCF-2: for Glioma-Derived Monocyte Chemotactic Factor; hJE: for human JE gene product; MCAF: for Monocyte Chemotactic Factor; and MCP: for Monocyte Chemoattractant Protein-1. As the amino acid sequences for these chemokines was found to be identical, the term MCP has been adopted for describing this particular chemokine. It is thus referred to in the art as other chemokines that share significant sequence homology with MCP-1, and have been named MCP-2 and MCP-3, according to the order of their discovery.

The amino acid sequence of MCP-1 shows the mature protein to be 99 amino acids long starting at what corresponds to nucleotide 70 of the gene. The functional portion of the protein is known to be the active portion with the first 23 amino acids serving as a signal sequence. MCP-1 is a secretory N-glycosylated glycoprotein of a variety of molecular weights but predominantly occurring at 13,000; 15,000; and 15,500 Daltons with post-translational modification probably accounting for the various forms. The two former isoforms have been named alpha and beta respectively but the structural differences between the two are still unknown. Yet, it is known that their amino acids sequences are identical, apparently derived from a single gene product.

Many mitogenic and activating stimuli appear to cause secretion of MCP-1 by a wide variety of cells. These findings suggest that the cellular regulation of MCP-1 expression is complex, and involves circulating cytokine levels in addition to other factors. Viral and bacterial infections in turn, can affect these levels and are thus involved in the function of MCP-1.

The size and amino acid sequence of MCP-3 is also known as illustrated by Van Damme, et al., 1992, J. Exp. Med. 176:59–65, incorporated herein by reference. It has also been determined that MCP-3 is a chemotactic factor that can attract monocytes and that it can bind heparin.

Amino acids sequences of all proteins described in detail in the present invention are given using the following single letter code: A= ala, C= cys, D= asp, E= glu, F= phe, G= gly, H= his, I=ile, K=lys, L=leu, M=met, N=asn, P=pro, Q=gln, R=arg, S=ser, T=thr, V=val, W=trp, Y=tyr.

Accordingly, there remains a significant and urgent need to determine the mechanism used by meningitis etiological agents, as diverse as bacteria and viruses, to attract and infect monocytes and/or gaining access to the CNS. There also remains a significant and urgent need to develop a therapeutic capable of blocking such infection of the CNS by bacterial and viral meningitis etiologic agents utilizing such a mechanism. Specifically, there remains a need in the art for a monoclonal antibody specific for both bacterial and viral infectious agents of meningitis, where said monoclonal antibodies would recognize both bacterial and viral infectious agents of meningitis and have substantial diagnostic utility. Additionally, there is also a need for a known proteinaceous region containing the epitope(s) recognized by said monoclonal antibody where said epitope or peptide could be chemically synthesized, thereby avoiding the difficulties inherent in purification and administration of larger fragments of the antigenic molecules. An additional need for this said peptide is evident for use in diagnostic test kits to indicate meningitis infection as well as would also be useful in the development of a general meningitis vaccine.

BRIEF DESCRIPTION OF THE DRAWINGS

FIG. 1 depicts the amino acid sequence (SEQ ID NO: 1) of the Structural Polyprotein protein of the M22 strain of Rubella virus with sequences of interest underlined.

Figure 2:
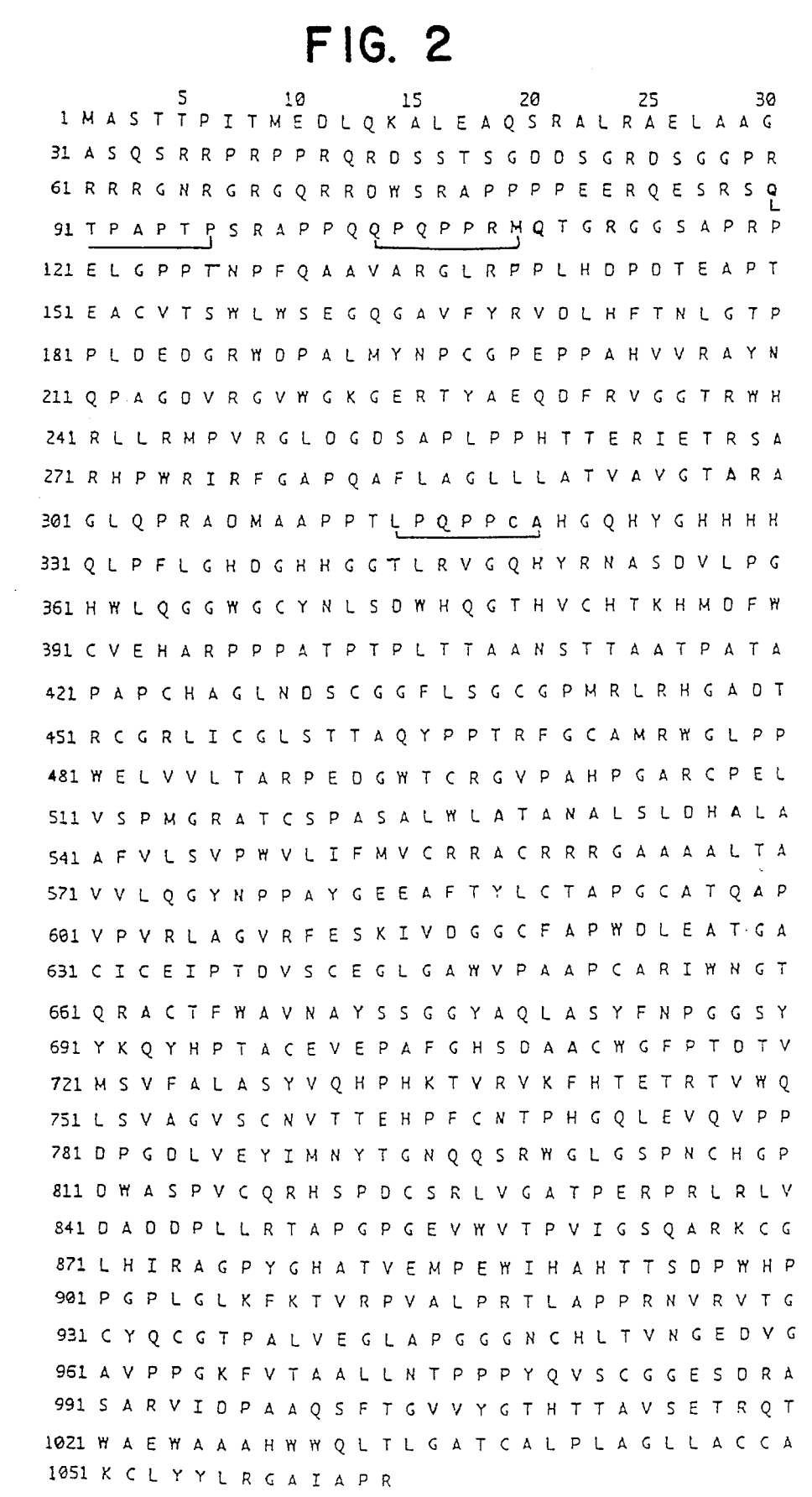

FIG. 2 depicts the amino acid sequence (SEQ ID NO: 8) of the Structural Polyprotein of the Therien strain of Rubella virus with sequences of interest underlined.

FIG. 3 depicts the amino acid sequence (SEQ ID NO: 11) of the Gag Polyprotein of the LV isolate of HIV-1 with sequences of interest underlined.

FIG. 4 depicts the amino acid sequence (SEQ ID NO: 14) of the Envelope Polyprotein Precursor protein of the LV-1a isolate of HIV-1 with sequences of interest underlined.

FIG. 5 depicts the amino acid sequence (SEQ ID NO: 17) of the Lipoprotein E Precursor of Haemophilus influenzae with sequences of interest underlined.

FIG. 6 depicts the amino acid sequence (SEQ ID NO: 20) of the Opacity-Related Protein of Neisseria meningitidis with sequences of interest underlined.

FIG. 7 depicts the amino acid sequence (SEQ ID NO: 23) of the Pneumococcal Surface Protein A of *Streptococcus pneumoniae* with sequences of interest underlined.

FIG. 8 depicts the amino acid sequence (SEQ ID NO: 26) of Protein P60 Precursor of *Listeria monocytogenes* with sequences of interest underlined.

FIG. 9 depicts the amino acid sequence (SEQ ID NO: 35) of the chemokine hMCP-1 with sequences of interest underlined.

FIG. 10 depicts the amino acid sequence (SEQ ID NO: 38) of the chemokine HMCP-3 with sequences of interest underlined.

Lane 1—Molecular weight markers of 97, 66, 45, 31, 21, and 14 kD. Lane 2—*H. Influenzae b*—proteins of approximate weights of 50, 45, 40, and 25 kD. Lane 3—*L. monocytogenes*—proteins of approximate weights of 60 kD (major) and 66 kD (minor), Lane 4/5—*S. pneumoniae*—proteins of approximate weights of 60 kD and 66 kD, Lane 6/7—*N. meningitidis*—a protein of approximate weights of 18 kD, identified by reaction with Mab RV1.

Figure 13:
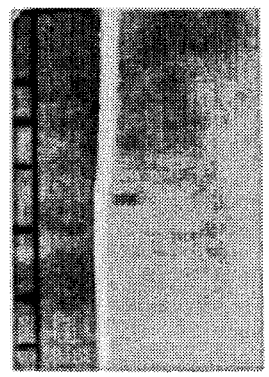

FIG. 13, Immunoblots of HIV1 antigens reacted with RV Mab RV1. HTLV-IIIB viral lysate, lot #54–040, purchased from Applied Biotechnologies, Inc., Md., USA. Lane 1—Molecular weight markers of 97, 66, 45, 31, 21, and 14 kD. Lane 2—Control RV antigens, 31 and 45 kD, reacting with RV1 Mab. Lane 3/4—HIV1 antigen of approximate weights of proteins at 24 kD and 61kD, identified by reaction with Mab RV1.

BRIEF DESCRIPTION OF THE INVENTION

The present invention provides novel peptides corresponding to homologous antigenic amino acid sequences on regions of bacterial and viral agents known to cause meningitis and on chemokines known to attract monocytes, in addition to monoclonal antibodies reactive with such antigenic regions and peptides. It also provides analogues of those peptides and mixtures and combinations of those peptides and analogues. These novel materials find use in, for example, a wide variety of diagnostic and preventive methods, means and compositions with respect to the overall process of pathogenesis which uses chemokine function to promote disease including meningitis, and atherosclerosis.

DETAILED DESCRIPTION OF THE INVENTION

The present invention provides novel compositions and methods for detecting, preventing and therapeutically treating disease wherein the pathogen or pathogenic mechanism includes a monoclonal antibody defined antigenic sequence. More specifically, using a monoclonal antibody defined by two rubella virus antigenic sites, a family of homologous cross-reacting antigenic sequences were identified in proteins associated with meningitis etiologic agents. These cross reacting antigenic sequences were in turn found to be significantly homologous to the C-terminal sequence of the monocyte attracting chemokines hMCP-1 and hMCP-3. Hence, this invention involves the use of peptides that mimick these homologous cross-reacting antigenic sequences and monoclonal antibodies reactive with such amino acid sequences to diagnose, treat and vaccinate against diseases wherein the pathogenic mechanism involves one or more members of these homologous cross-reacting sequences. An example of such a disease is meningitis.

A monoclonal antibody was used to identify two cross-reacting septapeptide antigens (QPQPPRM and PPQPPRA, SEQ ID NOS 3 and 7, respectively) contained in the Structural Polyprotein (Core and E2 outer membrane proteins portion described in greater detail below) of Rubella virus. The monoclonal antibody, RV1-Mab, was also found to cross-react with the p24 core protein and the p61 outer membrane protein of Human Immunodeficiency Virus-1 (HIV-1), known to cause meningitis during the initial stages of infection. Furthermore, the RV1-Mab was also found to cross react with proteins found in *Hemophilus influenzae*, *Neisseria meningitidis*, *Streptococcus pneumoniae* and *Listeria monocytogenes*, which together account for more than 85% of all bacterial meningitis in the United States. In this way, a family of homologous cross-reacting septapeptide antigens were discovered in viruses and bacteria known to cause meningitis. Because the RV1-Mab binds to amino acid sequences in diverse bacteria and viruses that are related only in the fact that they cause meningitis, these closely related homologous sequences have been designated Meningitis Related Homologous Antigenic Sequence (MRHAS).

A member of the MRHAS family can be defined as an amino acid sequence that is homologous to antigenic sites on the Structural Polypeptide (within the core and E2 membrane protein portion) of Rubella virus that are recognized by a Mab from the hybridoma RV-1. More specifically, any amino acid sequence, that is homologous to the regions extending from approximately amino acid residue 102 to 108 of the Structural Polyprotein (core protein region) and from about 313 to 319 of the Structural Polyprotein (E2 membrane protein) of the M33 strain of Rubella virus is by definition a member of the MRHAS family of sequences. The complete sequence of this Structural Polyprotein is found in FIG. 1 (SEQ ID NO: 1). Representative members that are cross-reactive with the RV1-Mab and appear in bacteria and viruses known to cause meningitis are presented in Table 1. The sequences of the proteins listed in Table 1 are found in FIGS. 1–8 and in SEQ ID NOS 3, 5, 7, 10, 13, 16, 19, 22, 25, 28, 30, 32, and 34.

Core protein portion or the E2 membrane-associated protein portion (from either the M33 or Therien strains), this reference denotes the portion of the Structural Polyprotein from which the final mature protein will be derived. A similar nomenclature with respect to precursor versus mature protein was also used in connection with the Gag Polyprotein of HIV-1, the Envelope Polyprotein Precursor of HIV-1, the Lipoprotein E Precursor, and the Protein P60 Precursor. For example the Protein P60 Precursor has, at a minimum, a 27 amino acid leader sequence that is removed during processing to mature protein.

Members of the MRHAS family were also found to appear in two variants of the chemokine, human Monocyte Chemoattractant Factor (hMCF). These two are hMCP-1 and hMCP-3, as indicated in Table 2. The sequences of the factors listed in Table 2 are found in FIGS. 9 and 10 (SEQ ID NOS and 38, respectively) and in SEQ ID NOS 37 and 40.

TABLE 2

| NAME | FACTOR | POSITION | SEQUENCE |
|---|---|---|---|
| MRHASMCP-1 | hMCP-1 | 70–76 | QTQTPKT SEQ ID NO 37 |
| MRHASMCP-3 | hMCP-3 | 61–67 | KTQTPKL |

TABLE 1

| NAME | VIRUS/ BACTERIUM | PROTEIN | SEQUENCE |
|---|---|---|---|
| MRHASRV-1 | Rubella virus | Structural Polyprotein (Core) | QPQPPRM SEQ ID NO 3 |
| MRHASRV-2 | Rubella virus | Structural Polyprotein (Core) | QTPAPKP SEQ ID NO 5 |
| MRHASRV-3 | Rubella virus | Structural Polyprotein (E2) | PPQPPRA SEQ ID NO 7 |
| MRHASRV-4 | Rubella virus | Structural Polyprotein (E2) | LPQPPCA SEQ ID NO 10 |
| MRHASHIV-1 | HIV1 | Gag Polyprotein | QAISPRT SEQ ID NO 13 |
| MRHASHIV-2 | HIV1 | Envelope Polyprotein Precursor | QNQQEKN SEQ ID NO 16 |
| MRHASHI-1 | Hemophilus influenzas | Lipoprotein E Precursor | QVQNNKP SEQ ID NO 19 |
| MRHASNM-1 | Nisseria meningitidis | Opacity- Related Protein POPM3 | IQPPKN SEQ ID NO 22 |
| MRHASSP-1 | Streptococcus pneumonias | Pneumococcal Surface Protein A | QQQPPKA SEQ ID NO 25 |
| MRHASLM-1 | Listeria monocytogenes | Protein P60 Precursor | PTQEVKK SEQ ID NO 28 |
| MRHASLM-2 | Listeria monocytogenes | Protein P60 Precursor | TTPAPKV SEQ ID NO 30 |
| MRHASLM-3 | Listeria monocytogenes | Protein P60 Precursor | NTATPKA SEQ ID NO 32 |
| MRHASLM-4 | Listeria monocytogenes | Protein P60 Precursor | QQTAPKA SEQ ID NO 34 |

It is noted that within the Structural Polyprotein of Rubella virus, there are three proteins that can be ultimately derived. Therefore, when a reference is made to either the TABLE 2-continued

| NAME | FACTOR | POSITION | SEQUENCE |
|------|--------|----------|----------|
|      |        |          | SEQ ID NO 40 |

It is surprising that bacteria and viruses as diverse as *Hemophilus influenzae, Neisseria meningitidis, Streptococcus pneumoniae, Listeria monocytogenes*, RV, and HIV-1 share a common feature, namely the placement of MRHAS, a highly conserved sequence, on the outer membrane. However, some of these etiological agents of meningitis do share specific features. For example, Williams and Blakemore have shown that bacteria can be carried into the CNS in association with monocytes migrating into the CSF compartment to maintain populations of resident macrophages (Cordy, 1984, *Vet. Pathol.* 21:593–597). This method of entry for bacteria would be analogous to that by which some viruses (HIV, Maaedi-Visna-caprine arthritis encephalitis virus) invade the CNS (Peluso, et al., 1985, *Virology* 147:231–236; Narayan and Cork, 1985, *Rev. Infec. Dis.* 7:899; Roy and Wainberg, 1988, *J. Leukoc. Clol.* 43:91–97; Westervelt et al., 1991, *Vaccines* 91:71–76). Moreover, available information for HIV-1 indicates that significant alterations in proteins carrying the MRHAS alters virulence, or invasiveness of the organisms.

Since the MRHAS that appear on bacterial and viral organisms are significantly homologous to sequences found in monocyte attracting chemokines, it is apparent that these agents have incorporated these sequences into their proteins to attract monocytes to aid in infection.

The unexpected discovery of monoclonal antibody cross-reactivity over various viral and bacterial species known to cause meningitis provides novel means for therapeutic and prophylactic treatments of meningitis. Moreover, the utility of this invention is extended by the significant homology of these antigenic sites with amino acid sequences in monocyte attracting chemokines. These novel means may be applied to diseases as diverse as meningitis and atherosclerosis, wherein the pathogen or pathogenic mechanism includes one or more of these MRHAS.

More specifically, a hybridoma is used to produce cross-reacting monoclonal antibodies that bind MRHAS in vivo and in vitro. These antibodies are useful as a diagnostic tool to detect the presence of MRHAS. One such diagnostic use is to detect the presence of bacterial and viral agents of meningitis in biological samples. Such Mabs are also useful for treating a patient to prevent and/or treat infection due to a meningitis etiologic virus and/or bacteria. A bacterial and/or viral meningitis infection can also be detected using peptides mimicking MRHAS in a diagnostic test. In vivo, peptides mimicking MRHAS can also be used as a novel vaccine for meningitis, in addition to use as blocking agents (therapeutics) to prevent the accumulation of monocytes involved in CNS infection and diseases such as atherosclerosis.

In one aspect, the novel peptides, typically less than about 30 amino acids, contain seven or more contiguous amino acids forming epitopes substantially similar to epitopes located on viruses and/or bacteria known to cause meningitis and/or on chemokines known to attract monocytes. Of particular interest are the regions extending from about amino acid residue: 102 to 108 (SEQ ID NO: 3) (core protein portion), 89 to 95 (SEQ ID NO: 5) (core protein portion), and 313 to 319 (SEQ ID NO: 7) (E2 membrane portion) of the Structural Polyprotein of the M33 strain of Rubella virus; from about 314 to 320 (SEQ ID NO: 10) (E2 membrane portion) of the Structural Polyprotein of the Therien strain of Rubella virus; from about 145 to 151 (SEQ ID NO: 13) of the Gag Polyprotein of the LV isolate of HIV-1; from about 655 to 661 (SEQ ID NO: 16) of the Envelope Polyprotein Precursor of the LAV-1a isolate of HIV-1; from about 99 to 105 (SEQ ID NO: 19) of the Lipoprotein E Precursor of *Haemophilus influenzae;* from about 1 to 5 (SEQ ID NO: 22) of the Opacity-Related Protein POPM3 of *Neisseria meningitidis;* from about 423 to 429 (SEQ ID NO: 25) of the Pneumococcal Surface Protein A of *Streptococcus pneumoniae;* from about 151 to 157 (SEQ ID NO: 28), 181 to 187 (SEQ ID NO: 30), 249 to 255 (SEQ ID NO: 32), and 292 to 298 (SEQ ID NO: 34) of the Protein P60 Precursor of *Listeria monocytogenes;* from about 93 to 99 (SEQ ID NO: 37) of the chemokine hMCP-1; and from about 61 to 67 (SEQ ID NO: 40) of the chemokine hMCP-3.

Those skilled in the art will appreciate that additional analogous regions ("homologs") from other infectious agents (viruses, bacteria, etc.) or chemokines may be identified based upon their sequence homology with members of the MRHAS family. In practice, such homologs may be identified by reference to the MRHAS occurring in hMCP-1, QTQTPKT (SEQ ID NO: 37).

This method can be applied to other infectious agents (viruses, bacteria, etc.) or chemokines that are yet to be discovered. For example, as new viruses or bacteria are identified that use monocytes to infect various regions of the body such as the CNS, their protein amino acid sequences may be aligned with that of the MRHAS in hMCP-1 to obtain maximum homology. The methods by which the sequences are aligned are known to those skilled in the art. The amino acid sequence of an infectious agent not listed herein, which corresponds to members of the MRHAS family specifically disclosed herein can be synthesized and used in accordance with the invention.

It is not necessary to the present invention that the epitopes contained within such sequences be cross-reactive with antibodies to all infectious agents of meningitis, or all chemokines that attract monocytes. Peptides encompassing immunological eiptopes which distinguish between types of monocytes or between efficacity for a particular type of monocyte will find utility in identifying different pathogenic mechanisms of infection and disease. For example, such utility will include infectious agents that use different modes of infectivity to enter the CNS. These peptides may also be useful in combination with other peptides representing other members of the MRHAS family in therapeutic composition.

In accordance with another aspect of the present invention, a novel cell line capable of producing monoclonal antibodies and compositions comprising such antibodies is provided, which antibodies are capable of selectively recognizing members of the MRHAS family. These monoclonal antibodies may be used in a wide variety of ways including diagnosis and therapy, as well as to identify other cross-reactive antibodies. Peptides or polypeptides containing the epitope(s) with which they react may find separate uses as immunogens for vaccines, or as therapeutic agents.

Generation of Monoclonal Antibodies

Monoclonal antibodies were prepared by immortalizing the expression of nucleic acid sequences that encode for antibodies or binding fragments thereof specific for members of the MRHAS family. See Godding, 1980, "Antibody Production by Hybridomas", *J. Immunol. Meth.*, 39:285–308 which is incorporated herein by reference. In brief, spleen cells from an immunized vertebrate that illustrate the desired antibody response are immortalized. Immunization protocols are well established and though such protocols can be varied considerably, they still remain effective. Also see, Goding, 1986, *Monoclonal Antibodies: Principles and Practice,* Academic Press, 2nd edition, which is herein incorporated by reference. Cell lines that produce the antibodies are most commonly made by cell fusion between suitably drug-marked human or mouse myeloma or human lymphoblastoid cells with human B-lymphocytes to yield the hybrid cell lines. Other methods include Ebstein-Barr Virus transformation of lymphocytes, transformation with bare DNA (such as oncogenes or retroviruses), or any other method which provides for stable maintenance of the cell line and the production of monoclonal antibodies. The general methodology followed for obtaining monoclonal antibodies is described in Kohler & Milstein, 1975, *Nature.* 256:495–496, which is incorporated herein by reference. The transformation or fusion can be carried out in conventional ways, the fusion technique being described in a number of patents: U.S. Pat. Nos. 4,172,124; 4,350,683: 4,363,799; 4,381,292; and 4,423,147, whose techniques and technologies are herein incorporated by reference. The procedure is also described by Kennett et al., *Monoclonal Antibodies* (1980) and references therein, as well as Goding, infra, all of which are incorporated herein by reference. Human monoclonal antibodies are acquired by fusion of the spleen cells with the appropriate human fusion partner, such as WI-L2 and as described in European Application No. 82,301103.6, the relevant portions of such a procedure incorporated herein by reference. A detailed technique for producing mouse X mouse monoclonal antibodies is taught by Oi & Herzenberg, in Mishell & Shiigi, 1980, *Selected Methods in Cellular Immunology:*351–372, which also is incorporated herein by reference. The resulting hybridomas are screened to isolate individual clones, where each clone secretes a single monoclonal antibody to a given MRHAS.

The antibodies generated herein can be used without modification or may be modified in a number of ways. For example, such modification can be by way of labeling (meaning joining), either covalently or non-covalently, a moiety which directly or indirectly provides for some means of detection. A variety of such labels are known and include: substrates, enzymes, co-factors, inhibitors, chemiluminescers, fluorescers, radionuclides, magnetic particles, and the like.

Moreover, fragments of such monoclonal antibodies can exist that continue to possess noteable specificity for a given MRHAS. As such, all antibody binding fragments or reference to such 'fragment(s) thereof' refers to a lesser portion of a complete antibody that retains some, if not all, of its binding specificity and capacity for a given MRHAS.

Therefore, one preferred embodiment of this invention involves a composition comprising a monoclonal antibody or binding fragment thereof which binds to one or more members of a group of homologous antigenic amino acid sequences comprising MRHAS.

A further embodiment of this invention involves a cell line that produces a monoclonal antibody or binding fragment thereof which binds to members of a family comprising MRHAS.

As yet another embodiment of this invention involves a cell line that produces a monoclonal antibody or binding fragment thereof which binds to an epitope shared by bacterial and viral meningitis etiologic agents, wherein said cell line is RV-1 which was deposited at the American Type Tissue Collection (ATCC) 12301 Parklawn Drive, Rockville Md. 20852 on May 26, 1993 and accorded accession number HB 11362.

Another embodiment of this invention is a monoclonal antibody produced by the cell line RV-1 (ATCC HB 11362).

It is also a preferred embodiment of this invention that there be a monoclonal antibody capable of reacting with a MRHAS, wherein the monoclonal antibody specifically blocks the binding of an antibody produced by a cell line that produces a monoclonal antibody or binding fragment thereof which binds to members of a family comprising MRHAS, and where such cell line can be RV-1 (ATCC HB 11362).

Another embodiment involves a monoclonal antibody capable of reacting with an antigenic determinant, or homologs thereof, wherein the monoclonal antibody specifically blocks the binding of an antibody produced by a cell line that produces a monoclonal antibody or binding fragment thereof which binds to members of a family comprising MRHAS, and where said cell line can be RV-1 (ATCC HB 11362) and wherein said antigenic determinant is selected from the amino acid sequences presented in Table 3 and in SEQ ID NOS 2, 4, 6, 9, 12, 15, 18, 21, 24, 27, 29, 31, 33, 36 and 39.

TABLE 3

| VIRUS/ BACTERIUM/ CHEMOKINE | PROTEIN | AMINO ACID REGION | AMINO ACID SEQUENCE |
|---|---|---|---|
| Rubella virus | Structural Polyprotein | 95–115 | PSRAPPQQPQPPRMQTGRGGS |
| Rubella virus | Structural Polyprotein | 82–102 | ERQESRSQTPAPKPSRAPPQQ |
| Rubella virus | Structural Polyprotein | 306–326 | DMAAPPMPPQPPRAHGQHYGH |
| Rubella virus | Structural Polyprotein | 306–326 | DMAAPPTLPQPPCAHGQHYGH |
| HIV-1 | Gag Polyprotein | 138–158 | IQGQMVHQAISPRTLNAWVKV |
| HIV-1 | Envelope Polyprotein Precursor | 648–668 | HSLIEESQNQQEKNEQELLEL |
| Haemophilus influenzas | Lipoprotein E Precursor | 92–111 | NSPYAGWQVQNNKPFDGKDWT |

TABLE 3-continued

| VIRUS/ BACTERIUM/ CHEMOKINE | PROTEIN | AMINO ACID REGION | AMINO ACID SEQUENCE |
|---|---|---|---|
| Neisseria meningitidis | Opacity-Related Protein POPM3 | 1–13 | IQPPKNLLFSSLL |
| Streptococcus pneumonias | Pneumococcal Surface Protein A | 416–436 | EEYNRLTQQQPPKAEKPAPAP |
| Listeria monocytogenes | Protein P60 Precursor | 144–164 | AVSTPVAPTQEVKKETTTQQA |
| Listeria monocytogenes | Protein P60 Precursor | 174–194 | VKQTTQATTPAPKVAETIKETP |
| Listeria monocytogenes | Protein P60 Precursor | 242–262 | LAIKQTANTATPKAEVKTEAP |
| Listeria monocytogenes | Protein P60 Precursor | 285–305 | KKETATQQQTAPKAPTEAAKP |
| Chemokine hmCp-1 | | 86–99 | SMDHLDKQTQTPKT |
| Chemokine hMCP-3 | | 54–67 | FMKHLDKKTQTPKL |

Yet another embodiment of this invention is a monoclonal antibody capable of reacting with an antigenic determinant of the proteins presented in Table 4 and in SEQ ID NOS 3, 5, 7, 10, 13, 16, 19, 22, 25, 28, 30, 32, 34, 37 and 40, wherein the antigenic determinant is selected from the amino acid sequences presented in Table 4.

TABLE 4

| VIRUS/ BACTERIUM/ CHEMOKINE | PROTEIN | AMINO ACID REGION | AMINO ACID SEQUENCE |
|---|---|---|---|
| Rubella virus | Structural Polyprotein | 102–108 | QPQPPRM |
| Rubella virus | Structural Polyprotein | 89–95 | QTPAPKP |
| Rubella virus | Structural Polyprotein | 313–319 | PPQPPRA |
| Rubella virus | Structural Polyprotein | 313–319 | LPQPPCA |
| HIV-1 | Gag Polyprotein | 145–151 | QAISPRT |
| HIV-1 | Envelope Polyprotein Precursor | 655–661 | QNQQEKN |
| Haemophilus influenzas | Lipoprotein E Precursor | 99–105 | QVQNNKP |
| Neisseria meningitidis | Opacity-Related Protein POPM3 | 1–5 | IQPPKN |
| Streptococcus pneumonias | Pneumococcal Surface Protein A | 423–429 | QQQPPKA |
| Listeria monocytogenes | Protein P60 Precursor | 151–157 | PTQEVKK |
| Listeria monocytogenes | Protein P60 Precursor | 181–187 | TTPAPKV |
| Listeria monocytogenes | Protein P60 Precursor | 249–255 | NTATPKA |
| Listeria monocytogenes | Protein P60 Precursor | 292–298 | QQTAPKA |
| Chemokine hMCP-1 | | 93–99 | QTQTPKT |
| Chemokine hMCP-3 | | 61–67 | KTQTPKL |

Pharmaceutical Formulations and Use

The monoclonal antibodies of this invention that bind MRHAS can also be incorporated as components of pharmaceutical compositions. The composition should contain a therapeutic or prophylactic amount of at least one of the monoclonal antibodies of the present invention with a carrier that is pharmaceutically effective. Such a pharmaceutical carrier should be any compatible, non-toxic substance that is suitable to deliver the monoclonal antibodies to the patient. Such carriers can be sterile water, alcohols, fats, waxes, and inert solids. The pharmaceutical composition may also be incorporate pharmaceutically acceptable adjuvants (eg. buffering agents or dispersing agents). Hence, the monoclonal antibodies of the present invention can be employed as separately administered compositions given in conjunction with other anti-bacterial or anti-viral agents.

The monoclonal antibodies, peptides, and pharmaceutical compositions thereof, oil the present invention are particularly useful for oral or parenteral administration. It is preferred that the pharmaceutical compositions be administered parenterally: i.e., subcutaneously, intramuscularly, or intravenously. Therefore, this invention is providing compositions for parenteral administration that comprises a solution of the monoclonal antibody, peptide, or a cocktail thereof dissolved in an suitable carrier (which is preferably an aqueous carrier). Examples of the aqueous carriers that can be used are water, buffered water, 0.4% saline, 0.3% glycine, or the like. These solutions are to be sterile and generally free of particulate matter. Moreover, these compositions may be sterilized by conventional and well known sterilization techniques. The compositions may also contain pharmaceutically acceptable auxiliary substances. These substances are required to approximate physiological conditions such as pH adjusting and buffering agents, toxicity adjusting agents, and the like. Examples of these auxiliary substances are sodium acetate, sodium chloride, potassium chloride, calcium chloride, sodium lactate, etc. The concentration of antibody and/or peptide in these formulations can widely vary depending on its ultimate use, activity, and mode of administration of the composition. The concentration of antibody and/or peptide in these formulations will be selected primarily based on such factors as fluid volumes, viscosities, etc. It is preferable that such factors be chosen for the particular mode of administration selected. The actual methods used for preparing parenterally administrable compositions will be known or is apparent to those skilled in the art and are described in *Remington's Pharmaceutical Science*, 15th Ed. (Easton: Mack Publishing Company, 1980), which is herein incorporated by reference.

The monoclonal antibodies and peptides of this invention can be lyophilized for storage and can be reconstituted in a suitable carrier prior to their use. Such techniques have been shown to be effective with conventional immunoglobulins and lyophilization and reconstitution techniques that are known in the art can be applied. It will also be appreciated by those skilled in the art however, that lyophilization and reconstitution can lead to varying degrees of antibody activity loss (e.g., with conventional immunoglobulins, IgM antibodies tend to have greater activity loss than IgG antibodies). As such, the use levels may have to be adjusted to compensate for any possible loss of activity.

The compositions containing the present monoclonal antibodies, or cocktails thereof can be dispensed for the prophylactic and/or therapeutic treatment of such diseases as meningitis or other maladies that may involve monocytes, monocyte-attracting chemokines or MRHAS (such as arteriosciserosis). In such therapeutic application, compositions are administered to patients who have contracted or begun to develop a disease involving MRHAS, chemokines, or chemokine recognizing monocytes in the pathogenic mechanism. The administration of such composition is in an amount sufficient to bind the chemical signal, i.e. to the MRHAS or chemokine. For example, a composition comprising the present monoclonal antibody is administered in a therapeutic application to a patient—already infected with a meningitis etiologic agent(s)—in an amount sufficient to cure, arrest, or at least partially arrest the infection and its complications.

In prophylactic applications, compositions containing the present antibodies or a cocktail thereof are administered to a patient not already infected by a disease-causing agent bearing an antigen that contains a MRHAS (ie. a meningitis-causing agent), but perhaps such patient has recently been exposed to or thought to have been exposed to, or was at risk of being exposed to such agent, to enhance the patient's resistance to such potential infection or to vaccinate against such agent.

The compositions containing the present peptides or cocktails thereof can be administered not only for the prophylactic and/or therapeutic treatment of meningitis, but also possibly for arteriosclserosis, or such related disease involving monocytes, monocyte-attracting chemokines or MRHAS. In therapeutic application, compositions are administered to a patient who has contracted or begun to develop a disease involving MRHAS, or homologs thereof, or chemokine recognizing monocytes in the pathogenic mechanism, in an amount sufficient to block the MRHAS signal recognition by monocytes. For example, a composition containing such a peptide may be administered in a therapeutic application to a patient already infected with a meningitis etiologic agent(s), in an amount sufficient to block MRHAS recognition sites on monocytes by interfering with the ability of said agents to attract and infect monocytes (and thus interfere with the infectivity of the CNS by said agent(s).

In prophylactic applications, compositions containing one or more peptides mimicking members of the MRHAS family or a cocktail thereof are also useful as the active component of vaccines capable of inducing protective immunity against both bacterial and viral meningitis causing agents. The possible routes of administration, the antigen doses, and the number and frequency of injections will vary from individual to individual and may parallel those currently being used in providing immunity to other viral infections. For example, the vaccines of the present invention are pharmaceutically acceptable compositions that contain at least one peptide of this invention, its analogues or mixtures or combinations thereof, in an amount that is effective in a mammal (including humans) treated with that composition to raise antibodies sufficient to protect such mammal from viral or bacterial meningitis for a period of time.

The vaccines of the present invention are prepared in accordance with known methods and are conveniently and conventionally combined with physiologically acceptable carrier materials, such as pharmaceutical grade saline, tetanus toxoid, and keyhole limpet hemocyanin. The vaccine compositions of the present invention may also include adjuvants or other enhancers of immune response, such as liposomes, alum preparations, or immunomodulators. Furthermore, these vaccine compositions may comprise other antigens to provide immunity against other viruses and bacteria. The amount of these other antigens is again dependent on the mammal to be treated, the type of disease, and the actual course of the disease. A single or multiple administration of the compositions can be done with dose levels and pattern being selected by the administering physician. However, the antigen should be present in an amount effective to raise antibodies sufficient to protect the treated mammal from that pathogen or virus for a period of time.

Furthermore, the monoclonal antibodies of the present invention may find use as a target-specific-carrier molecule. Such use would involve binding an antibody to either a toxin to form an immunotoxin, or radioactive material or drug to form a radiopharmaceutical or pharmaceutical. Methods for producing immunotoxins, radiopharmaceuticals, or such pharmaceuticals are well known as set out in 1984, *Cancer Treatment Reports* 68:317 which is incorporated herein by reference.

It is also possible that heteroaggregates of the monoclonal antibodies from the present invention and human T-cell activators (such as monoclonal antibodies to the CD3 antigen or to the Fc gamma receptor on T-cells) may enable human T-cells or Fc-gamma bearing cells (such as K cells or neutrophils) to kill meningitis-etiologic agent infected cells via antibody dependent cell-mediated cytolysis. By way of example, such heteroaggregates may be assembled by covalently cross-linking the anti-MRHAS antibodies to the anti-CD3 antibodies using the heterobifunctional reagent N-succinimidyl-3-(2-pyridyldithiol)-propionate, as described by Karpowsky et al., 1984, *J. Exp. Med.* 160:168, which is herein incorporated by reference.

It is therefore, a preferred embodiment of this invention that there be a monoclonal antibody composition specifically reactive with an epitope selected from one the bacterial or viral sequences listed in Table 3 (SEQ ID NOS 2, 4, 6, 9, 12, 15, 18, 21, 24, 27, 29, 31, 33, 36 and 39), wherein the sequence or homolog of said sequence is within the region listed in Table 3, and wherein said monoclonal antibody is capable of blocking the infectivity of the virus or bacteria.

A further embodiment of this invention involves a monoclonal antibody composition specifically reactive with an epitope of a chemokine selected from one of the chemokine sequences listed in Table 4 (SEQ ID NOS 3, 5, 7, 10, 13, 16, 19, 22, 25, 28, 30, 32, 34, 37 and 40), wherein the sequence or homolog of said sequence is within the region listed in Table 3 (SEQ ID NOS 2, 4, 6, 9, 12, 15, 18, 21, 24, 27, 29, 31, 33, 36 and 39), and wherein said monoclonal antibody is capable of binding said chemokine in vivo to significantly reduce CNS infectivity of meningitis etiologic agents.

Yet another embodiment of this invention is a vaccine formulation comprising an immunogenic peptide comprising one or more members of the MRHAS family or an immunogenic portion thereof.

Another embodiment of this invention is a method for protecting against CNS infection of bacterial and/or viral meningitis etiologic agents by blocking a recognition site on monocytes that recognizes MRHASs.

A further embodiment of this invention is a method of treating a patient to prevent an infection due to a meningitis etiologic virus and/or bacteria, said method comprising administering a prophylactically effective amount of a composition useful in the prophylactic or therapeutic treatment of viral and/or bacterial meningitis, said composition comprising a monoclonal antibody or binding fragment thereof which binds to MRHAS shared by viral and/or bacterial meningitis etiologic agents.

Yet another embodiment of this invention is a method of treating a patient infected with a meningitis etiologic virus and/or bacteria, said method comprising administering a therapeutically effective amount of a composition useful in the prophylactic or therapeutic treatment of viral and/or bacterial meningitis, said composition comprising a monoclonal antibody or binding fragment thereof which binds to MRHAS shared by viral and/or bacterial meningitis etiologic agents.

Another embodiment of this invention entails an article of manufacture adapted for use in an immunoassay for antibodies to bacterial and/or viral meningitis etiologic agents comprising a solid support having bound thereto a peptide comprising one or more members of a group of peptides based on MRHASs, wherein said peptide having the formula a—X—b, wherein X is a sequence of at least 7 amino acids taken as a block selected from the group comprised in Table 5 below, with said block maintaining the sequence in the N terminus to C terminus direction of the native amino acid sequence and analogue thereof, said analogues resulting from conservative substitutions in or modifications to the native amino acid sequence block;

a is selected from the group consisting of:
  (i) an amino terminus;
  (ii) one to eight amino acids taken as a block from and maintaining the sequence and N terminus to C terminus direction of that portion of the native amino acid sequence of the protein immediately N-terminal to said X or conservative substitutions in or modifications thereto; and
  (iii) a substituent effective to facilitate coupling of the peptide to another moiety; and b is selected from the group consisting of:
  (i) a carboxy terminus;
  (ii) one to eight amino acids taken as a block from and maintaining the sequence and N terminus to C terminus direction of that portion of the native amino acid sequence of the protein immediately C-terminal to said X or conservative substitutions in or modifications thereto; and
  (iii) a substituent effective to facilitate coupling of the peptide to another moiety.

A further embodiment of the present invention is a composition useful in the prophylactic or therapeutic treatment of viral and/or bacterial meningitis, said composition comprising peptides selected from the MRHAS family and/or the peptides described in the preceding paragraph.

Diagnostic Uses of Monoclonal Antibodies

The monoclonal antibodies and peptides of the present invention are also useful for diagnostic purposes and can be either labelled or unlabelled. Diagnostic assays typically entail the detection of a complex formation through the binding of the monoclonal antibody to a MRHAS. When unlabelled, the antibodies can find use, for example, in agglutination assays. Moreover, unlabelled antibodies can be used in combination with other labelled antibodies (second antibodies) that are reactive with the monoclonal antibody of the present invention. An example of this is antibodies specific for immunoblobulin. Alternatively, the monoclonal antibodies can be directly labelled. A wide variety of labels may be employed, such as enzymes, enzyme substrates, enzyme cofactors, enzyme inhibitors, radionuclides, fluorescers, ligands (particularly haptens), etc. In addition, numerous types of immunoassays are available and, by way of example, some assays include those described in U.S. Pat. Nos. 3,817,827; 3,850,752; 3,901, 654; 3,935,074; 3,984,533; 3,996,345; 4,034,074; and 4,098,876, all of which (with references) are incorporated herein by reference.

It is common for the monoclonal antibodies and peptides of the present invention to be employed in enzyme immunoassays, where for example, the subject antibodies (or second antibodies from a different species) are conjugated to an enzyme. When a biological sample containing MRHAS antigens, such as human blood serum, saliva, cerebrospinal fluid or bacterial and/or viral infected cell culture suspension, is combined with the subject antibodies, binding occurs between the antibodies and those molecules exhibiting the desired epitope. It should be noted that the biological sample may require concentration in order to detect organisms of low titer. Such proteins, bacterial or viral particles may then be separated from any unbound reagents and a second antibody (labeled with an enzyme) added. The presence of the antibody-enzyme conjugate specifically bound to the antigen can then be determined. Other conventional techniques well known to those skilled in the art may also be used.

Kits can also be equipped with the subject monoclonal antibodies of the present invention, for detection of meningitis etiologic agents or for the presence of MRHASs. Hence, the subject monoclonal antibody compositions of the present invention may be provided, usually in a lyophilized form, either alone or in conjunction with additional antibodies specific for other epitopes of meningitis etiologic agents. The antibodies, which may be conjugated to a label, or unconjugated, are included in such kits along with buffers such as Tris, phosphate, carbonate, and the like, along with the requesite stabilizers, biocides, inert proteins (eg. bovine serum albumin) that are standard to those skilled in the art.

It is therefore, a preferred embodiment of this invention that there be a monoclonal antibody composition specifically reactive with an epitope selected from one the bacterial or viral sequences listed in Table 3 (SEQ ID NOS 2, 4, 6, 9, 12, 15, 18, 21, 24, 27, 29, 31, 33, 36 and 39), wherein the sequence or homolog of said sequence is within the region listed in Table 3, and wherein said monoclonal antibody is capable of detecting the infectivity of the virus or bacteria. As a note, that use of the said antibodies with biological samples containing low titer meningitis etiologic agents may require concentrating said samples before the diagnostic procedure is performed.

A further embodiment involves a monoclonal antibody composition specifically reactive with an epitope selected from one of the chemokine sequences listed in Table 3 (SEQ ID NOS 2, 4, 6, 9, 12, 15, 18, 21, 24, 27, 29, 31, 33, 36 and 39), wherein the sequence or homolog of said sequence is within the region listed in Table 3, and wherein said monoclonal antibody is capable of detecting said chemokine in vivo to indicate CNS infectivity of meningitis causing agents.

Yet another embodiment of this invention entails a method of diagnosing the presence of bacterial and/or viral meningitis etiologic agents in a biological sample, said method comprising the steps of forming an antibody/antigen complex wherein the antibody portion of said complex comprises a monoclonal antibody capable of binding to both bacterial and viral meningitis etiologic agents, and detecting the presence of the antibody/antigen complex formed.

A further embodiment of this invention involves an immunoassay to detect the presence of antibodies to bacterial and/or viral meningitis etiologic agents in a biological sample comprising contacting said sample with one or more immunogenic peptide(s), where said peptide is selected from one or more members of the MRHAS family, the improvement comprising the method of screening for bacterial and/or viral meningitis etiologic agents in one test.

A further embodiment of this invention involves an immunoassay to detect the presence of antibodies to bacterial and/or viral meningitis etiologic agents in a biological sample comprising contacting said sample with one or more immunogenic peptide(s), where said peptide is selected from one or more members of the MRHAS family comprising a peptide having the formula a—X—b wherein:
X is a sequence of at least 7 amino acids taken as a block selected from the group comprised in Table 5:

TABLE 5

(i) the amino acid sequence of the Structural Polyprotein of a strain of Rubella virus that corresponds to $AA_{102}$–$AA_{108}$ (SEQ ID NO: 3) of said protein of the M33 strain of Rubella virus as set forth in FIG. 1 (SEQ ID NO: 1);

(ii) the amino acid sequence of the Structural Polyprotein of a strain of Rubella virus that corresponds to $AA_{89}$–$AA_{95}$ (SEQ ID NO: 5) of said protein of the M33 strain of Rubella virus as set forth in FIG. 1 (SEQ ID NO: 1);

(iii) the amino acid sequence of the Structural Polyprotein of a strain of Rubella virus that corresponds to $AA_{313}$–$AA_{319}$ (SEQ ID NO: 7) of said protein of the M33 strain of Rubella virus as set forth in FIG. 1 (SEQ ID NO: 1);

(iv) the amino acid sequence of the Structural Polyprotein of a strain of Rubella virus that corresponds to $AA_{103}$–$AA_{109}$ (SEQ ID NO: 10) of said protein of the Therien strain of Rubella virus as set forth in FIG. 2 (SEQ ID NO: 8);

(v) the amino acid sequence of the Structural Polyprotein of a strain of Rubella virus that corresponds to $AA_{90}$–$AA_{96}$ of said protein of the Therien strain of Rubella virus as set forth in FIG. 2 (SEQ ID NO: 8);

(vi) the amino acid sequence of the Structural Polyprotein of a strain of Rubella virus that corresponds to $AA_{314}$–$AA_{320}$ of said protein of the Therien strain of Rubella virus as set forth in FIG. 2 (SEQ ID NO: 8);

(vii) the amino acid sequence of the Gag Polyprotein of an isolate of the HIV-1 that corresponds to $AA_{145}$–$AA_{151}$ (SEQ ID NO: 10) of the Gag Polyprotein of the LV isolate of HIV-1 as set forth in FIG. 3 (SEQ ID NO: 11);

(viii) the amino acid sequence of the Envelope Polyprotein Precursor of an isolate of the HIV-1 that corresponds to $AA_{655}$ to $AA_{661}$ (SEQ ID NO: 16) of the Envelope Polyprotein Precursor of the LAV-1a isolate of HIV-1 as set forth in FIG. 4 (SEQ ID NO: 14);

(ix) the amino acid sequence that corresponds to $AA_{99}$–$AA_{105}$ (SEQ ID NO: 19) of the Lipoprotein E Precursor of Haemophilus influenzae as set forth in FIG. 5 (SEQ ID NO: 17);

(x) the amino acid sequence that corresponds to $AA_1$ to $AA_5$ (SEQ ID NO: 22) of the Opacity-Related Protein POPM3 of *Neisseria meningitidis* as set forth in FIG. 6 (SEQ ID NO: 20);

(xi) the amino acid sequence that corresponds to $AA_{423}$ to $AA_{429}$ (SEQ ID NO: 25) of the Pneumococcal Surface Protein A of *Streptococcus pneumoniae* as set forth in FIG. 7 (SEQ ID NO: 23);

(xii) the amino acid sequence that corresponds to $AA_{151}$–$AA_{157}$ (SEQ ID NO: 28) of the Protein P60 Precursor of Listeria monocytogenes as set forth in FIG. 8 (SEQ ID NO: 26);

(xiii) the amino acid sequence that corresponds to $AA_{181}$–$AA_{187}$ (SEQ ID NO: 30) of the Protein P60 Precursor of Listeria monocytogenes as set forth in FIG. 8 (SEQ ID NO: 26);

(xiv) from the amino acid sequence of that corresponds to $AA_{249}$–$AA_{255}$ (SEQ ID NO: 32) of the Protein P60 Precursor of *Listeria monocytogenes* as set forth in FIG. 8 (SEQ ID NO: 26);

(xv) from the amino acid sequence that corresponds to $AA_{292}$–$AA_{298}$ (SEQ ID NO: 34) of the Protein P60 Precursor of Listeria monocytogenes as set forth in FIG. 8 (SEQ ID NO: 26);

(xvi) from the amino acid sequence of a variant of the chemokine human Monocyte Chemoattractant Factor hMCP-1, that corresponds to $AA_{93}$–$AA_{99}$ (SEQ ID NO: 37) of hMCP-1 as set forth in FIG. 9 (SEQ ID NO: 35);

(xvii) from the amino acid sequence of the chemokine hMCP-3, that corresponds to $AA_{61}$–$AA_{67}$ (SEQ ID NO: 40) of hMCP-3 as set forth in FIG. 10 (SEQ ID NO: 38); and (xviii) from any amino acid sequence present within a protein that is homologous to members of the MRHAS family;

with said block maintaining the sequence in the N terminus to C terminus direction of the native amino acid sequence and analogue thereof, said analogues resulting from conservative substitutions in or modifications to the native amino acid sequence block;

a is selected from the group consisting of:
  (i) an amino terminus;
  (ii) one to eight amino acids taken as a block from and maintaining the sequence and N terminus to C terminus direction of that portion of the native amino acid sequence of the protein immediately N-terminal to said X or conservative substitutions in or modifications thereto; and
  (iii) a substituent effective to facilitate coupling of the peptide to another moiety; and b is selected from the group consisting of:
  (i) a carboxy terminus;
  (ii) one to eight amino acids taken as a block from and maintaining the sequence and N terminus to C terminus direction of that portion of the native amino acid sequence of the protein immediately C-terminal to said X or conservative substitutions in or modifications thereto; and
  (iii) a substituent effective to facilitate coupling of the peptide to another moiety, the improvement comprising the method of screening for bacterial and/or viral meningitis etiologic agents in one test.

Yet a further embodiment of the present invention is a method for analyzing a sample of a biological fluid with regard to the presence of anti-X antibodies therein, where X is selected from one or more members of the group comprising:
  (i) Rubella virus;
  (ii) HIV-1;
  (iii) *Hemophilus influenzae;*
  (iv) *Nisteria meningitidis;*
  (v) *Streptococcus pneumoniae;*
  (vi) *Listeria monocytogenes,* and comprising the steps of:

A) providing a solid support having bound thereto a peptide selected from one or more members of the MRHAS family, or said peptide is selected from one or more members of the MRHAS family comprising a peptide having the formula $$a-x-b$$

wherein:
X is a sequence of at least 7 amino acids taken as a block selected from the group comprised in Table 5, and with said block maintaining the sequence in the N terminus to C terminus direction of the native amino acid sequence and analogue thereof, said analogues resulting from conservative substitutions in or modifications to the native amino acid sequence block; a is selected from the group consisting of:
  (i) an amino terminus;
  (ii) one to eight amino acids taken as a block from and maintaining the sequence and N terminus to C terminus direction of that portion of the native amino acid sequence of the protein immediately N-terminal to said X or conservative substitutions in or modifications thereto; and
  (iii) a substituent effective to facilitate coupling of the peptide to another moiety; and b is selected from the group consisting of:
  (i) a carboxy terminus;
  (ii) one to eight amino acids taken as a block from and maintaining the sequence and N terminus to C terminus direction of that portion of the native amino acid sequence of the protein immediately C-terminal to said X or conservative substitutions in or modifications thereto; and
  (iii) a substituent effective to facilitate coupling of the peptide to another moiety, B) contacting said solid support with said human sample to provide a sample-contacted support;
C) washing said sample-contacted support to provide a washed support; and
D) determining whether human antibodies are bound to said support.

Preparation and Use of Synthetic Peptides

Novel peptides are provided in the present invention which immunologically mimic protein epitopes encoded by infectious agents that cause meningitis and by monocyte-attracting chemokines. To accommodate variations among different infectious agents, adjustments for conservative substitutions, and selection among the alternatives where non-conservative substitutions are involved, may be made. There are many uses for these peptides which include, for example, use as: immunogens for a vaccine; blockers of MRHAS recognition sites on monocytes, interfering with the ability of meningitis etiologic agents to attract and infect monocytes and thereby block access of the infectious agent to the CNS; blockers of MRHAS recognition sites on monocytes involved in plaque build-up that occurs during atherosclerosis; and as antigens in diagnostic kits to detect antibodies in biological fluid as indication of infection by meningitis etiologic agents. Depending upon the nature of the protocol, the peptides may be conjugated to a carrier or other compounds, unlabeled or labeled, bound to a solid surface, or the like.

Embodiments of the present invention include peptides of interest derived from MRHAS family members listed in Table 1 (SEQ ID NOS 3, 5, 7, 10, 13, 16, 19, 22, 25, 28, 30, 32, and 34). Further embodiments include peptides of interest derived from MRHAS family members and their parent monocyte-attracting chemokines listed in Table 2 (SEQ ID NOS 37 and 40). Other possible embodiments include MRHAS family members found on proteins listed in Table 3 (SEQ ID NOS 2, 4, 6, 9, 12, 15, 18, 21, 24, 27, 29, 31, 33, 36 and 39).

The peptides of interest will include at least five, sometimes six, sometimes seven, sometimes eight, sometimes 15, sometimes 21, usually fewer than about 50 and preferably fewer than about 25 amino acids included within a sequence homologous to a member of the MRHAS family. It is desired that a given peptide be as small as possible while still maintaining all of the immunoreactivity or monocyte attracting activity of the larger corresponding peptide. Furthermore, it may be desirable in some instances to join two or more oligopeptides which are non-overlapping to form a single peptide structure or to use them as individual peptides at the same time, which separately or together provide equivalent sensitivity to the parent.

A given peptide may be modified by introducing conservative or non-conservative substitutions in the peptide, usually fewer than 50 number percent, and more usually fewer than 30 number percent, more usually with fewer than 15 number percent of the amino acids being exchanged (Waterman, 1986, *Nucleic Acids Res.* 14:9095; Hitachi, HIBIO MacDNASIS Pro: DNA and Protein Sequence Analysis Software System Reference Manual, both incorporated in their entirety by reference). In those situations where amino acid regions are found to be polymorphic, it may be desirable to vary one or more particular amino acids to more effectively mimic the differing epitopes of the different meningitis etiologic infectious agents, or monocyte attracting chemokines.

It is important that it be understood that the polypeptide employed in the present invention need not be identical to any particular MRHAS family member, so long as the subject peptide is able to provide for immunological competition with proteins of at least one of the members of the MRHAS family and/or demonstrate monocyte recognition and/or attracting activity. Therefore, the subject peptide may be subject to various changes, such as substitutions, insertions, and deletions, either conservative or nonconservative, where such changes may provide for certain advantages in their use.

It is also important to point out that one, two, or more amino acids may be added to the termini of an oligopeptide or peptide to provide for ease of linking peptides one to another, for coupling to a support, or larger peptide and for reasons to be discussed subsequently, for modifying the physical or chemical properties of the peptide or oligopeptide, or the like.

In the present invention, the term amino acid is used to include, but not limited to, all natural occurring amino acids and all synthetic or non-natural amino acids such as homocysteine. The term 'amino acids selected as a block' (or other similar statements) means a linear sequence of a set number of amino acids that taken together form a group. The term 'antigenic determinant' means the structural component of an antigen molecule responsible for its specific interaction with antibody molecules elicited by the same or related antigen as defined by *Dorland's Pocket Medical Dictionary* 23ed. (Philadelphia: Saunders, 1982) at 198; Morris, ed. Academic Press Dictionary of Science and Technology (San Diego: Academic Press, 1992) which are both incorporated in their entirety by reference. The term 'conservative substitution' means the substitution of one or more amino acids for another in which the antigenic determinant (including its secondary structure and hydropathic nature) of a given antigen is completely or partially conserved in spite of the substitution. The term 'analogues of a peptide' means amino acid insertions, deletions, substitutions, and modifications of one or more sites in the peptide chain. The term 'immunogenic' means the property that endows a substance with the capacity to provoke an immune response (Dorland, infra). The terms 'corresponds' and 'corresponding' refers to the native amino acids of those defined region of a given peptide sequence. Finally, amino acids such as cysteine, lysine, glutamic or aspartic acid, tyrosine, or the like may be introduced at the C- or N-terminus of a given peptide or oligopeptide to provide for a useful functionality for linking purposes. It will be appreciated by those skilled in the art that cysteine is particularly preferred to facilitate covalent coupling to other peptides or to form polymers by oxidation.

Moreover, a given peptide or oligopeptide sequence may differ from the natural sequence by the sequence being modified by terminal —$NH_2$ acylation (eg. by acetylation, or thioglycolic acid amidation, terminalcarbosy amidation, e.g., with ammonia or methylamine) to provide stability, increased hydrophobicity for linking or binding to a support or other molecule, or for purposes of polymerization.

Of particular interest to the present invention is the use of the mercaptan group of cysteins or thioglycolic acids used for acylating terminal amino groups, or the like, for linking two of the peptides or oligopeptides or combinations thereof by a disulfide linkage or a longer linkage to form polymers that contain a number of MRHAS epitopes. Such polymers have the advantage of increased immunological reaction. Furthermore, where different peptides are used to make up the polymer, they possess the additional ability to induce antibodies that immunoreact with several antigenic determinants of the different meningitis etioligic agents.

In order to achieve the formation of antigenic polymers (ie. synthetic multimers), compounds may be utilized having bis-haloacetyl groups, nitroarylhalides, or the like, where the reagents being specific for thio groups. Therefore, the link between two mercapto groups of the different peptides or oligopeptides may be a single bond or may be composed of a linking group of at least two, typically at least four, and not more than about 16, but usually not more than about 14 carbon atoms.

To prepare the novel peptides of the present invention, any of the conventional peptide production techniques may be employed. These techniques include synthesis, recombinant DNA technology and combinations thereof. The peptide may be synthesized in solution or on a solid support in accordance with conventional techniques. A variety of automatic synthesizers are commercially available and can be used in accordance with known protocols. For example, see Stewart & Young, 1984, *Solid Phase Peptide Synthesis* 2nd ed., Pierce Chemical Co.; Tam et al., 1983, *J. Am Chem. Soc.* 105:6442 which are both incorporated herein by reference. Recombinant DNA technology may be utilized where a synthetic gene may be prepared by employing single strands which code for the given MRHAS polypeptide or substantially complementary strands thereof, where the single strands overlap and can be brought together in an annealing medium so as to hybridize. The hybridized strands may then be ligated to form the complete gene, and, by choice of appropriate termini, the gene may be inserted into expression vectors, which are readily available today. For example, see Maniatis et al., 1982, *Molecular Cloning, A Laboratory Manual,* Cold Spring Harbor Laboratory which is herein incorporated by reference. In the alternative, the region of the genome coding for the given MRHAS peptide may be cloned by conventional recombinant DNA techniques and expressed (See Maniatis, infra).

It is therefore, a preferred embodiment of this invention that there be a peptide having the formula a—X—b wherein, X is a sequence of at least 7 amino acids taken as a block selected from the group comprised in Table 5, with said block maintaining the sequence in the N terminus to C terminus direction of the native amino acid sequence and analogue thereof, said analogues resulting from conservative substitutions in or modifications to the native amino acid sequence block;

a is selected from the group consisting of:
- (i) an amino terminus;
- (ii) one to eight amino acids taken as a block from and maintaining the sequence and N terminus to C terminus direction of that portion of the native amino acid sequence of the protein immediately N-terminal to said X or conservative substitutions in or modifications thereto; and
- (iii) a substituent effective to facilitate coupling of the peptide to another moiety; and b is selected from the group consisting of:
- (i) a carboxy terminus;
- (ii) one to eight amino acids taken as a block from and maintaining the sequence and N terminus to C terminus direction of that portion of the native amino acid sequence of the protein immediately C-terminal to said X or conservative substitutions in or modifications thereto; and
- (iii) a substituent effective to facilitate coupling of the peptide to another moiety.

Other features and advantages of the present invention will become apparent from the following experimental descriptions, which describe the invention by way of example. The examples are offered by way of illustration and not by way of limitation.

EXAMPLE I

Generation and Characterization of Monoclonal Antibodies

Example I describes the method for the generation of hybridoma cell lines that produce monoclonal antibodies with a specificity for MRHAS. This method involves the use of purified Rubella virus as the immunogen. The protocols for the generation of the hybridima cell lines that produce the said monoclonal antibody and the characterization of the antibodies were as follows.

Rubella virus, strain M33, was obtained as the first passage after primary isolation. The RV strain was obtained from the laboratories of the National Institute of Health. Murine fibroblasts (L cells), used to generate stock virus, were maintained in monolayer cultures and were routinely propagated at 37° C. with minimal Eagle's medium (MEM) supplemented with 5% fetal calf serum (FCS, Grand Island Biological Company, GIBCO), 100 µg/ml streptomycin, and 100 IU/ml penicillin. Stock virus was routinely prepared by inoculating semiconfluent monolayers of L cells with RV at a multiplicity of infection (m.o.i.) of 0.01. After adsorption at 34° C. in a humid atmosphere containing 5% $CO_2$ for 1 hour, additional medium was added and the flask was incubated at 34° C. for 6 days, at which time the culture supernatant was collected and frozen at −80° C.

Virus purification was accomplished as follows. L cell monolayers were infected at an m.o.i. of 0.01 and incubated at 34° C. for 6 days as described. The culture supernatants were collected and centrifuged at 3000×g for 20 min. All procedures were carried out at 4° C. unless otherwise stated. The supernatant obtained was recentrifugated at 100,000×g for 3 hours and the resulting pellet was resuspended in 0.2 ml TNE buffer (0.15M NaCl, 50 Mm Tris-HCl, and 1 mM EDTA, pH 7.8). This sample was layered onto a 16 ml 25–45% discontinuous Renografin-60 (Reno M-60, Diatrisoate Meglumine, 60%, Squibb) gradient prepared with TNE buffer and centrifuged in an SW 27 Rotor at 55,000×g for 2 hours. The single, sharp band at the interface was collected, pelleted as described previously, resuspended in 0.5 ml TNM buffer (0.15 M NaCl, 50 mM Tris-HCl, 1 mM $MgCl_2$, pH 7.8), and layered on a 12 ml 30–45% continuous Renografin gradient prepared with TNM buffer. After centrifugation at 200,000×g for 3 hours, 0.5 ml fractions were collected. An aliquot was removed from each fraction for ELISA and infectivity tests (both described below). Appropriate fractions were then pooled, diluted with TNM buffer, and centrifuged at 100,000×g for 3 hours to remove the Renographin. Rubella antigen, prepared in this way, was used to immunize mice for the construction of hybridomas.

The ELISA was performed according to the procedure described by Volier in Rose & Freidman, eds., 1976, *Manual of Clinical Immunology*:506–512 which is incorporated herein by reference. Viral samples were diluted into coating buffer and duplicate 200 µl aliquots were adsorbed to microtiter plate wells (Cooke Laboratory Products, Dynatech Laboratories Inc., Alexandria, Va.). After coating, a predetermined 1/16 dilution of human anti-Rubella antiserum (H1 titer=1/128) was added to each well. Antibody binding was measured using a previously determined 1/2,000 dilution of rabbit antihuman IgG (Flow Laboratories) linked to alkaline phosphatase. The A400 nm was determined after 30 minutes incubation at room temperature.

The infectivity test is a technique used to titer RV and was based on the ability of RV-infected cells to adsorb erythrocytes. It employs, in principle, the procedure incorporated herein by reference of Hotchin et al., 1960, *Virology* 10:275–280 for measuring the infectivity of noncytopathic viruses. Serial doubling dilutions of RV suspensions were used to infect confluent monolayers of L2 cells grown in tissue culture chamber slides (Lab Tek Products, Division of Miles Laboratories, Inc., Ill.). Two-chamber slides were used. Each chamber received a 50 µl aliquot of the appropriate RV dilution. Virus was allowed to adsorb for 1 hour at 34° C. and 2.5 ml of medium and 50 µl of a 20% suspension of heparinized sheep erythrocytes in Alserver's solution were added directly to each chamber. The slides were then incubated for 24 hours at 34° C. The chambers were removed and each slide was washed gently by immersion if pH 7.4 Dulbecco phosphate-buffered saline (PBS) at room temperature and examined microscopically for hemadsorbing cells. Uninfected control monolayers were treated in an identical fashion.

Mice were immunized using the following procedure. A Balb/c mouse was inoculated intraperitoneally (IP) with 250 µg of *M. tuberculosis* and 15 µg of purified RV suspended in 45% Renografin. Approximately 4 weeks later, 4 booster doses of 10 μg of virus each were given intravenously at day minus 5, minus 4, minus 3 and minus 2, prior to fusion. The final boost was accompanied by an additional injection of the same dose IP. Serum was taken from the immunized mouse throughout to monitor antibody production against RV proteins.

A Balb/c mouse was immunized as previously described and one day after the final booster doses of purified virus, the mouse was sacrificed and a suspension of spleen cells was prepared and fused with myeloma cells (P3X63Ag8) in a ratio of 5:1 using 50% polyethylene glycol according to the procedure described by Koprowski et al., 1977, *Proc. Natl. Acad. Sci.* 74:2985–2988 incorporated herein by reference. Cultures containing 1×105 cells in 100 μl were established in 96–2311 Linbro plastic plates (Flow Laboratories, McLean, Va., USA) where each well contained a feeder layer of 4×103 murine peritoneal exudate cells (macrophages). Colonies appeared in 2 to 3 weeks and culture medium in appropriate well were screened for anti-Rubella antibody in the ELISA employing infected and uninfected L cell lysates as antigen. Cells that were producing antibody were subcloned and retested.

ELISA screening of clones was performed according to the procedure described by Voller, infra, as previously described. Infected L cell monolayers were detached by scraping, sonicated and diluted in coating buffer to give a final protein concentration of 100 μg protein/100 μl of lysate. Each microwell was coated with 200 μl of lysate. After coating overnight at 4° C., 100 μl of each test supernatant was added. After a 90 minute incubation at 37° C., and washing, 100 μl of rabbit anti-mouse IgG, linked to alkaline phosphatase (Flow Laboratories) was added, and the plate was reincubated for one hour at 37° C. After addition of 100 μl of a 10% diethanolamine solution (pH 9.8), containing 1 mg/ml p-nitrophenylphosphate (Sigma), the plate was incubated for one hour at 37° C. and the A400 nm was determined as before.

The immunoglobulin class of anti-Rubella virus antibodies produced by the positive clones was determined by testing the supernatant from such clones against affinity purified anti-mouse immunoglobulin (South Biotech), using the ELISA methods.

Polyacrylamide slab gel electrophoresis (PAGE) of Rubella virus proteins was performed according to Laemmli, 1970, *Nature* 227:680–685 incorporated herein by reference. RV polypeptides in sample buffer (0.062 M Tris-HCl, pH 6.8) containing 2% SDS, 1% (v/v) glycerol, 0.5% (w/v) bromophenol blue and 1% 2-mercaptoethanol were placed in a boiling water bath for 2 minutes prior to electrophoresis at 25 mA for 2 hours on a 10% discontinuous acrylamide slab gel system. Aliquots of 15 μl containing 5 μg of protein were applied to each gel lane. Protein standards used for gel calibration were as follows: bovine serum albumin (66200), ovalbumin (45,000), carbonic anhydrase (28,000), soybean trypsin inhibitor (20,100), and alpha-lactalbumin (14,200) (Bio-Rad). Gels were stained with silver according to the procedure described by Wray et al., 1981, *Analyt. Biochem.* 118:197–203 incorporated herein by reference.

Rubella virus proteins separated by PAGE were transferred electrophoretically from the SDS-PAGE gel to nitrocellulose paper (Bio-Rad) by the method described by Towbin et al., 1979, *Proc. Nat. Aced. Sci.* 76:4350–4354 incorporated herein by reference. A constant current of 35 mA was applied to the gel-nitrocellulose paper sandwich for 1 hour, in an electroblot buffer of 25 mM Tris-HCl, 192 mM glycine and 20% (v/v) methanol at pH 8.3. The proteins transferred onto the blot were either stained with amido black or detected by enzyme immunoassay. The latter was performed by soaking the paper in PBS containing 1% milk for 30 minutes in order to clock non-specific protein binding sites. The paper was then incubated with monoclonal antibody at 37° C. for 1 hour., washed 3 times with PBS followed by and hour incubation at 37° C. with peroxidase-conjugated goat anti-mouse immunoglobulin (Cappel, Cochranville, Pa.) diluted 1/1000 in PBS containing 3% BSA. After 3 additional washes, the blots were soaked in a solution of 0-dianisidine prepared as described by Towbin, infra.

Characterization of Mabs directed against RV 30,000 dalton protein

One fusion yielded 268 clones. After initial screening, 12 (4.5%) of the 266 clones were positive against infected cell lysates. The 12 clones were recloned and only 4 of these remained stable antibody producers. The 4 clones as listed in Table 6 were designed RV1–RV4 and further characterized according to Ig class and molecular weight of the antigen recognized.

TABLE 6

Summary of Mab characteristics of 4 stable hybridoma clones obtained

| Origined done | Cell line Designation | Immunoglobulin Class/subclass | A 410 nm | Molecular weight of antigen recognized (Kd) |
|---|---|---|---|---|
| 101 B1 | RV1 | — | 0.248 | — |
| 201 A5 | RV2 | — | 0.126 | — |
| 6C6 | RV3 | — | 0.241 | — |
| 1A1 | RV4 | — | 0.174 | — |

Figure 11:
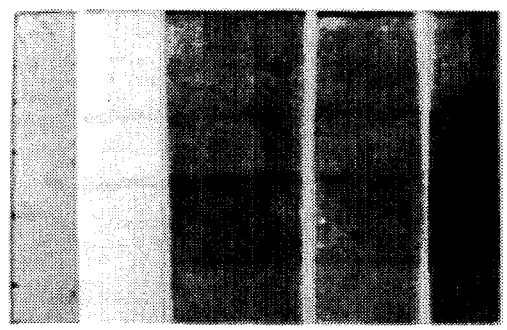
FIG. 11, Immunoblots of RV antigens reacted with Mab's RV1, RV2, RV3 and RV4. RV antigen: Strain MPV-77 (lot#50678, Catalogue #EL-05-04) cultured in Vero cells. Purchased from Microbix Biosystems Inc., Toronto, Ontario). All Mab used as tissue culture fluid diluted 1/500. Lane 1—Molecular weight markers of 97, 66, 45, 31, 21, and 14 kD. Lane 2/3—RV4; lane 4/5/6—RV3; lane 7/8—RV2; lane 9/10—RV1. Lanes 2–9 all illustrate two proteins, 31 kD (major) and 45 kD (minor), identified by reactions with Mab's 1–4.

The first band to appear on immunoblotting was consistently the p30 core protein. However, a second band was observed at approximately 40,000 Kd and was clear after 30 minutes incubation. The larger 40 Kd protein has been designated E2 and has been shown to have a molecular weight of 35–38 Kd (vaccine strain and wild type 349). The E2 membrane protein is glycosylated and is detected in mature virions as a protein with a molecular weight of approximately 40,000–43,000 daltons. These results are summarized in FIG. 11.

The four hybridomas were isolated from a single fusion, but can be seen to be independent isolates from the differences observed in the immunoglobulin class determinations. In spite of their obvious differences, the clones were all directed against the same (cross-reacting) epitopes which appears to be on the RV core protein having a molecular weight of approximately 30,000.

A comparison of nucleotide sequences for the p30 core and p35- 8 E1 sequences contained in the 24S subgenomic messenger RNA of RV (Zheng, 1989, infra) in Table 7 revealed that one core sequence (SEQ ID NO: 3) was homologous with one E2 sequence (SEQ ID NO: 7) as follows:

TABLE 7

COMPARISON OF SEQUENCE HOMOLOGIES BETWEEN p30 AND p38 IN THE RUBELLA VIRUS GENOME

| ORIGIN | AMINO ACID POSITION | SEQUENCE |
| --- | --- | --- |
| RV (p30) core | 102 | Q-P-Q-P-P-R-M (SEQ ID NO: 3) |
| RV (E2) membrane | 313 | P-P-Q-P-P-R-A (SEQ ID NO: 7) |

In view of the core/outer membrane cross-reactivity of the RV monoclonal antibodies, it was certain that these antibodies would detect the presence of both p30 core and E2 membrane proteins, thereby limiting their use in any diagnostic system which would attempt to define the status of RV infection in the CNS as permissive, or non-permissive, for growth.

However, the significance of the external placement of the internal core sequence in the membrane-associated E2 protein represents an important viral strategy as noted that amino acid changes in the E2 protein of several alphaviruses have been found in Sindbis virus (Davis et al. ,1986, *Proc. Natl. Acad. Sci.* 83; 6771–6775), Ross River virus (Faragher et al., 1988, *Virology* 163:509–526) and Venezuelan equine encephalitis virus (Johnson et al., 1986, *J. Gne. Virol.* 67: 1951–1960), to be implicated in the modulation of viral virulence.

EXAMPLE 2

The Use of RV1 Mab to Detect and Define Homologous Meningitis-Specific Antigenic sequences In the course of RV1 Mab Characterization, it was observed that the RV1 Mab cross-reacted with bacterial antigens in *N. meningitidis, S. Pneumoniae, H. Influenzae, L. monocytogenes* as well as antigens in HIV-1. Immunoblots were performed as previously described using bacterial antigens and HIV-1 antigens and RV-1 Mab.

Bacterial Strains and Culture Conditions

The bacterial strains were obtained from the American Type Culture Collection (ATCC), Washington, D.C. (*Neisseria meningitidis* and *Streptococcus pneumoniae*) and from the Caribbean Epidemiology Centre (CAREC), Port of Spain, Trinidad (*Streptococcus pneumoniae*). All strains were grown on chocolate agar overnight at 37° C. in an atmosphere containing 5% $CO_2$. Cultures were stored in brain heart infusion broth containing 20% glycerol at –70° C.

Antigen Preparation for PAGE and Immunoblotting

Antigens present in the outer membrane protein fraction of *Neisseria meningitidis* were prepared using lithium chloride as previously described by Johnston et al., 1976, *J. Exp. Med.* 143: 741–758 incorporated herein by reference. Whole cells were suspended in lithium chloride buffer (200 mM lithium chloride, 100 mM lithium acetate, 10 mM EDTA, pH 6.0), transferred to a 250 ml erlenmeyer flask containing 3–5 mm glass beads and shaken at 300 rpm in a G24 Environmental incubator shaker for 2 hours at 45° C. The suspension was centrifuged at 8,000 rpm for 20 minutes using a Sorvall SS034 fixed angle rotor with R max=10.70 cm. Collected supernatant was transferred to a rigid wall polycarbonate tube and centrifuged at 35,000 rpm for 2 hr at 10° C. using a 50.2 Beckman rotor. The supernatant was discarded and pellet resuspended in 1 ml of phosphate buffered saline (PBS). The protein content was determined by the Lowry method.

Sonicated antigen preparations of *S. pneumoniae* and *H. influenzae* were prepared using the following procedure. Approximately $10^{11}$ bacteria were suspended in 5 ml PBS and heat-killed for 20 min at 56° C. Using a Branson 350 Sonifier Cell disruper (Branson Cleaning Equipment Co.) cells were sonicated 3 times, with a 50% pulse setting, for 5 minutes each time. The sample was kept at 4° C. with ice throughout. The suspensions were then centrifuged for 20 min at 25,000 rpm, using a Beckman 70 Ti.1 rotor at 10° C. The protein concentration of the resulting supernatant was determined using the Lowrey protein assay.

HIV-1 antigen was purchased from ABI (Advanced Biotechnologies, Inc., Columbia, Md.). Antigen was contained in viral lysate with specifications given in catalog number 10-119- 000 with Lot number 54–040 containing a particle count of $1.09 \times 10^{10}$ vp/ml active virus. The preparation was treated with Triton X-100 added to a final concentration of 1%, and heated to 56° C. for one hour with mixing. The final protein concentration of lysate was 0.78 mg/ml. Each lane for PAGE contained 10 µg of antigen.

PAGE and Immunoblotting procedures.

PAGE was carried out as previously described using 15 µl samples of bacterial antigen, containing 5 µg protein per well. Immunoblots were performed on the transferred antigens using RV1 Mab in tissue culture supernatants as previously described.

Figure 12:
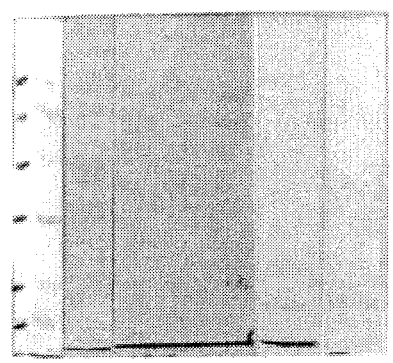
FIG. 12, Immunoblots of bacterial antigens reacted with V Mab RV1. H. Influenzae b antigen from ATCC (#10211); *L. monocytogenes* from ATCC (#7644); *S/pneumoniae* from the Caribbean Regional Epidemiology Centre, CAREC, Trinidad; *N. meningitidis* A from ATCC (#13077).

The results of immunoblots of bacterial antigen using RV1 Mab are contained in FIG. 12. The RIV Mab clearly detected cross-reacting epitopes in *N. Meningitidis, H. influenzae, S. pneumoniae* and eliminated all of these bands, indicating that the antigens detected with the RV Mab are protein in nature. Control *Streptococcus A* and *M. tuberculosis* (p60) antigen preparations were negative using the RV1Mab.

The results of immunoblots of HIV antigens using RV1 Mab are contained in FIG. 13. The RV1Mab clearly detected two membrane protein antigens indicating that HIV employs a strategy identical to that of RV which places a portion of the inner core protein on the outside of the virion.

Since the likely sequences of the corresponding RV1 Mab antigens are QPQPPRM (SEQ ID NO: 3) and PPQPPCA (SEQ ID NO: 7) in the core and E2 proteins, respectively, a search was undertaken to find similar, cross-reacting sequences in the available bacterial and HIV sequences, with results the data presented in TABLE 4.

FIG. 12 illustrates a cross-reactivity, with the RV1 Mab detecting a major band of approximately 26–28,000 daltons and 2 minor bands at approximately 45,000 daltons. An outer membrane protein with a molecular weight of about 28,000, expressed on the cell surface, and existing as a lipoprotein in association with the outer membrane-cell wall complex of *H. influenzae* has been identified and designated Protein E. It is capable of eliciting a bactericidal immune response against non-typable *H. Influenzae* and is highly conserved among *H. influenzae* strains. Protein E has been sequence (Green and Zlotnick, infra) and the sequences listed in Table 4 (SEQ ID NOS 3, 5, 7, 10, 13, 16, 19, 22, 25, 28, 30, 32, 34, 37 and 40) are closely homologous to the membrane and core sequences of RV shown in that table.

FIG. 12 also illustrates that the RV1Mab detected one band at approximately 60,000 daltons with *L. monocytogenes*. All virulent *L. monocytogenes* stains secrete as SH-activated cytolysin called listeriolysin (Kuhn & Goebel, 1988, *Infect. Immun.* 56:79–82). This protein, termed p60, is an essential virulence factor as nonhemolytic mutants have reduced rates of survival in the mouse infection model (Gaillard, et al., 1986, *Infect. Immun.* 52:50–55) and in mouse peritoneal macrophages (Kuhn & Goebel, infra). The sequence of the p60 has been determined (Kohler, et al., 1990, *Infec. Immun.* 58:1943–1950) and the sequences identified at the positions listed in Table 4 (SEQ ID NOS 3, 5, 7, 10, 13, 16, 19, 22, 25, 28, 30, 32, 34, 37 and 40) are closely homologous to the RV core and membrane sequence.

Finally, FIG. 13 illustrates that the RV Mab detected two bands at approximately 24,000 (p24) and 61,000 (p61) daltons. The p24 has been shown to be a major core protein and p61 a transmembrane protein in the HIV virion, and the complete nuceotide sequence of the HIV1 genome is available (Ratner et al., 1985, *Nature* 313:277–280). A number of septapeptide sequences were identified which are closely homologous to the RV core and membrane sequences, and these sequences are listed in Table 4 (SEQ ID NOS 3, 5, 7, 10, 13, 16, 19, 22, 25, 28, 30, 32, 34, 37 and 40).

We claim:

1. A composition comprising a carrier and a monoclonal antibody or antigen-binding fragment thereof which binds to a Meningitis Related Homologous Antigenic Sequence contained in the amino acid sequence of a protein or peptide, wherein said protein or peptide is found in a bacterium or virus that is an etiologic agent of meningitis.

2. A competition comprising a carrier and a monoclonal antibody or antigen-binding fragment thereof which binds to a Meningitis Related Homologous Antigenic Sequence contained in the amino acid sequence of a protein or peptide, wherein said protein or peptide is a chemokine involved in cell chemotaxis.

3. A composition according to claim 1, wherein said bacterium or virus is selected from the group consisting of Rubella virus, Human Immunodeficiency Virus-1, *Haemophilus influenzae, Neisseria meningitidis, Streptococcus pneumonias* and *Listeria monocytogenes.*

4. A composition according to claim 3, wherein said virus is Rubella virus.

5. A composition according to claim 4, wherein said Rubella virus is strain M33.

6. A composition according to claim 4, wherein said Rubella virus is strain Therien.

7. A composition according to claim 1, wherein said protein is the Structural Polyprotein of Rubella virus strain M22 comprising SEQ ID NO: 1.

8. A composition according to claim 1, wherein said protein is the Structural Polyprotein of Rubella virus comprising SEQ ID NO: 8.

9. A composition according to claim 1, wherein said protein is the E2 membrane-associated protein of Rubella virus comprising SEQ ID Nos: 7 or 10.

10. A composition according to claim 1, wherein said protein is the Envelope Polyprotein of the LAV-1a isolate of HIV-1 comprising SEQ ID NO: 14.

11. A composition according to claim 1, wherein said protein is the Gag Polyprotein of the LV isolate of HIV-1 comprising SEQ ID NO: 11.

12. A composition according to claim 1, wherein said protein is the Lipoprotein E Precursor of *Haemophilus influenzae* comprising SEQ ID NO: 17.

13. A composition according to claim 1, wherein said protein is the Opacity-Related Protein A of *Neisseria meningitidis* comprising SEQ ID NO: 20.

14. A composition according to claim 1, wherein said protein is the Pneumococcal Surface Protein A of *Streptococcus pneumonias* comprising SEQ ID NO: 23.

15. A composition according to claim 1, wherein said protein is the Protein P60 Precursor of *Listeria monocytogenes* comprising SEQ ID NO: 26.

16. A hybridoma cell line that produces a monoclonal antibody or antigenic-binding fragment thereof which binds to a Meningitis Related Homologous Antigenic Sequence contained in the amino acid sequence of a protein or peptide, wherein said protein or peptide is found in a bacterium or virus that is an etiologic agent of meningitis.

17. A hybridoma cell line according to claim 16, wherein said cell line is substantially free from other cellular material.

18. A monoclonal antibody or antigen-binding fragment thereof which binds to a Meningitis Related Homologous Antigenic Sequence contained in the amino acid sequence of a protein or peptide, wherein said monoclonal antibody or antigen-binding fragment is capable of blocking the binding of the monoclonal antibody produced by the cell line of claim 16.

19. A monoclonal antibody produced by said hybridoma cell line of claim 16.

20. A hybridoma cell line designated RV-1 having ATCC deposit accession number HB 11362.

21. A monoclonal antibody produced by said hybridoma cell line of claim 20.

22. A monoclonal antibody or antigen-binding fragment thereof that binds to an antigenic determinant of a Meningitis Related Homologous Antigenic Sequence contained in the amino acid sequence of protein or peptide found in a bacterium or virus that is an etiologic agent of meningitis, wherein said antigenic determinant is contained within an amino acid sequence selected from the group consisting of SEQ ID NO:1; SEQ ID NO:2; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22; SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32; SEQ ID NO:33; SEQ ID NO:34; and SEQ ID NO:35.

23. A monoclonal antibody or antigen-binding fragment thereof that binds to an antigenic determinant of a Meningitis Related Homologous Antigenic Sequence contained in the amino acid sequence of protein or peptide that is a chemokine involved in cell chemotaxis, wherein said antigenic determinant is contained within an amino acid sequence selected from the group consisting of SEQ ID NO:36; SEQ ID NO:37; SEQ ID NO:38; SEQ ID NO:39 and SEQ ID NO:40.

24. A hybridoma cell line that produces a monoclonal antibody or antigenic-binding fragment thereof which binds to a Meningitis Related Homologous Antigenic Sequence contained in the amino acid sequence of a protein or peptide, wherein said protein or peptide is a chemokine involved in cell chemotaxis.

* * * * *

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
( A ) LENGTH: 992 amino acids
( B ) TYPE: amino acid
( C ) STRANDEDNESS:
( D ) TOPOLOGY: unknown ( x i ) SEQUENCE DESCRIPTION: SEQ ID NO:1:

```
Met Ala Ser Thr Thr Pro Ile Thr Met Glu Asp Leu Gln Lys Ala Leu
 1               5                  10                  15

Glu Ala Gln Ser Arg Ala Leu Arg Ala Gly Leu Ala Ala Gly Ala Ser
            20                  25                  30

Gln Ser Arg Arg Pro Arg Pro Arg His Ala Arg Leu Gln His Leu
        35                  40                  45

Pro Glu Met Thr Pro Ala Val Thr Pro Glu Gly Pro Ala Pro Pro Arg
    50                  55                  60

Thr Gly Ala Trp Gln Arg Lys Asp Trp Ser Arg Ala Pro Pro Pro Pro
65                  70                  75                  80

Glu Glu Arg Gln Glu Ser Arg Ser Gln Thr Pro Ala Pro Lys Pro Ser
                85                  90                  95

Arg Ala Pro Pro Gln Gln Pro Gln Pro Pro Arg Met Gln Thr Gly Arg
            100                 105                 110

Gly Gly Ser Ala Pro Arg Pro Glu Leu Gly Pro Pro Thr Asn Pro Phe
        115                 120                 125

Gln Ala Ala Val Ala Arg Gly Leu Arg Pro Pro Leu His Asp Pro Asp
    130                 135                 140

Thr Glu Ala Pro Thr Glu Ala Cys Val Thr Ser Trp Leu Trp Ser Glu
145                 150                 155                 160

Gly Glu Gly Ala Val Phe Tyr Arg Val Asp Leu His Phe Ile Asn Leu
                165                 170                 175
```

```
Gly Thr Pro Pro Leu Asp Glu Asp Gly Arg Trp Asp Pro Ala Leu Met
            180                 185                 190
Tyr Asn Pro Cys Gly Pro Glu Pro Ala His Val Val Arg Ala Tyr
        195             200             205
Asn Gln Pro Ala Gly Asp Val Arg Gly Val Trp Gly Lys Gly Glu Arg
    210             215                 220
Thr Tyr Ala Glu Gln Asp Phe Arg Val Gly Gly Thr Arg Trp His Arg
225             230             235                     240
Leu Leu Arg Met Pro Val Arg Gly Leu Asp Gly Asp Thr Ala Pro Leu
            245             250                 255
Pro Pro His Thr Thr Glu Arg Ile Glu Thr Arg Ser Ala Arg His Pro
            260             265                 270
Trp Arg Ile Arg Phe Gly Ala Pro Gln Ala Phe Leu Ala Gly Leu Leu
        275             280             285
Leu Ala Ala Val Ala Val Gly Thr Ala Arg Ala Gly Leu Gln Pro Arg
    290             295             300
Ala Asp Met Ala Ala Pro Pro Met Pro Pro Gln Pro Pro Arg Ala His
305             310             315                     320
Gly Gln His Tyr Gly His His His His Gln Leu Pro Phe Leu Gly His
                325             330                 335
Asp Gly His His Gly Gly Thr Leu Arg Val Gly Gln His His Arg Asn
            340             345                 350
Ala Ser Asp Val Leu Pro Gly His Trp Leu Gln Gly Gly Trp Gly Cys
        355             360             365
Tyr Asn Leu Ser Asp Trp His Gln Gly Thr His Val Cys His Thr Lys
    370             375             380
His Met Asp Phe Trp Cys Val Glu His Asp Arg Pro Pro Pro Ala Thr
385             390             395                     400
Pro Thr Ser Leu Thr Thr Ala Ala Asn Tyr Ile Ala Ala Ala Thr Pro
            405             410             415
Ala Thr Ala Pro Pro Pro Cys His Ala Gly Leu Asn Asp Ser Cys Gly
            420             425                 430
Gly Phe Leu Ser Gly Cys Gly Pro Met Arg Leu Pro Thr Ala Leu Thr
        435             440             445
Pro Gly Ala Val Gly Asp Leu Arg Ala Val His His Arg Pro Val Pro
    450             455             460
Ala Tyr Pro Val Cys Cys Ala Met Arg Trp Gly Leu Pro Pro Trp Glu
465             470             475                     480
Leu Val Ile Leu Thr Ala Arg Pro Glu Asp Gly Trp Thr Cys Arg Gly
            485             490                 495
Val Pro Ala His Pro Gly Thr Arg Cys Pro Glu Leu Val Ser Pro Met
            500             505                 510
Gly Arg Ala Thr Cys Ser Pro Ala Ser Ala Leu Trp Leu Ala Thr Ala
        515             520             525
Asn Ala Leu Ser Leu Asp His Ala Phe Ala Ala Phe Val Leu Leu Val
    530             535             540
Pro Trp Val Leu Ile Phe Met Val Cys Arg Arg Ala Cys Arg Arg Pro
545             550             555                     560
Ala Pro Pro Pro Pro Ser Pro Gln Ser Ser Cys Arg Gly Thr Thr Pro
            565             570                 575
Pro Ala Tyr Gly Glu Glu Ala Phe Thr Tyr Leu Cys Thr Ala Pro Gly
            580             585                 590
Cys Ala Thr Gln Thr Pro Val Pro Val Arg Leu Ala Gly Val Gly Phe
```

|     |     |     |     |     | 595 |     |     |     |     | 600 |     |     |     |     | 605 |     |
| --- | --- | --- | --- | --- | --- | --- | --- | --- | --- | --- | --- | --- | --- | --- | --- | --- |
| Glu | Ser | Lys | Ile | Val | Asp | Gly | Gly | Cys | Phe | Ala | Pro | Trp | Asp | Leu | Glu |
|     |     | 610 |     |     |     |     | 615 |     |     |     | 620 |     |     |     |     |
| Ala | Thr | Gly | Ala | Cys | Ile | Cys | Glu | Ile | Pro | Thr | Asp | Val | Ser | Cys | Glu |
| 625 |     |     |     |     | 630 |     |     |     |     | 635 |     |     |     |     | 640 |
| Gly | Leu | Gly | Ala | Trp | Val | Pro | Thr | Ala | Pro | Cys | Ala | Arg | Ile | Trp | Asn |
|     |     |     |     | 645 |     |     |     |     | 650 |     |     |     |     | 655 |     |
| Gly | Thr | Gln | Arg | Ala | Cys | Thr | Phe | Trp | Ala | Val | Asn | Ala | Tyr | Ser | Ser |
|     |     |     | 660 |     |     |     |     | 665 |     |     |     |     | 670 |     |     |
| Gly | Gly | Tyr | Ala | Gln | Leu | Ala | Ser | Tyr | Phe | Asn | Pro | Gly | Gly | Ser | Tyr |
|     |     | 675 |     |     |     |     | 680 |     |     |     |     | 685 |     |     |     |
| Tyr | Lys | Gln | Tyr | His | Pro | Thr | Ala | Cys | Glu | Val | Glu | Pro | Ala | Phe | Gly |
|     | 690 |     |     |     |     | 695 |     |     |     |     | 700 |     |     |     |     |
| His | Ser | Asp | Ala | Ala | Cys | Trp | Gly | Phe | Pro | Thr | Asp | Thr | Val | Met | Ser |
| 705 |     |     |     |     | 710 |     |     |     |     | 715 |     |     |     |     | 720 |
| Val | Phe | Ala | Leu | Ala | Ser | Tyr | Val | Gln | His | Pro | His | Lys | Thr | Val | Arg |
|     |     |     |     | 725 |     |     |     |     | 730 |     |     |     |     | 735 |     |
| Val | Lys | Phe | His | Thr | Glu | Thr | Arg | Thr | Val | Trp | Gln | Leu | Ser | Val | Ala |
|     |     |     | 740 |     |     |     |     | 745 |     |     |     |     | 750 |     |     |
| Gly | Val | Ser | Cys | Asn | Val | Thr | Thr | Glu | His | Pro | Phe | Cys | Asn | Thr | Pro |
|     |     | 755 |     |     |     |     | 760 |     |     |     |     | 765 |     |     |     |
| His | Gly | Gln | Leu | Glu | Val | Gln | Val | Pro | Pro | Asp | Pro | Gly | Asp | Leu | Val |
|     | 770 |     |     |     |     | 775 |     |     |     |     | 780 |     |     |     |     |
| Glu | Tyr | Ile | Met | Asn | Tyr | Thr | Gly | Asn | Gln | Gln | Ser | Arg | Trp | Gly | Leu |
| 785 |     |     |     |     | 790 |     |     |     |     | 795 |     |     |     |     | 800 |
| Gly | Ser | Pro | Asn | Cys | His | Gly | Pro | Asp | Trp | Ala | Ser | Pro | Val | Cys | Gln |
|     |     |     |     | 805 |     |     |     |     | 810 |     |     |     |     | 815 |     |
| Arg | His | Ser | Pro | Asp | Cys | Ser | Arg | Leu | Val | Gly | Ala | Thr | Pro | Glu | Arg |
|     |     |     | 820 |     |     |     |     | 825 |     |     |     |     | 830 |     |     |
| Pro | Arg | Leu | Arg | Leu | Val | Asp | Ala | Asp | Pro | Leu | Leu | Arg | Thr | Ala |     |
|     |     | 835 |     |     |     |     | 840 |     |     |     |     | 845 |     |     |     |
| Pro | Gly | Pro | Gly | Glu | Val | Trp | Val | Thr | Pro | Val | Ile | Gly | Ser | Gln | Ala |
|     | 850 |     |     |     |     | 855 |     |     |     |     | 860 |     |     |     |     |
| Arg | Lys | Cys | Gly | Leu | His | Ile | Arg | Ala | Gly | Pro | Tyr | Gly | His | Ala | Thr |
| 865 |     |     |     |     | 870 |     |     |     |     | 875 |     |     |     |     | 880 |
| Val | Glu | Met | Pro | Glu | Trp | Ile | His | Ala | His | Thr | Thr | Ser | Asp | Pro | Trp |
|     |     |     | 885 |     |     |     |     | 890 |     |     |     |     | 895 |     |     |
| His | Pro | Pro | Gly | Pro | Leu | Gly | Leu | Lys | Phe | Lys | Thr | Val | Arg | Pro | Val |
|     |     |     | 900 |     |     |     |     | 905 |     |     |     |     | 910 |     |     |
| Ala | Leu | Pro | Arg | Ala | Leu | Ala | Pro | Pro | Arg | Asn | Val | Arg | Val | Thr | Gly |
|     |     | 915 |     |     |     |     | 920 |     |     |     |     | 925 |     |     |     |
| Cys | Tyr | Gln | Cys | Gly | Thr | Pro | Ala | Leu | Val | Glu | Gly | Leu | Ala | Pro | Gly |
|     | 930 |     |     |     |     | 935 |     |     |     |     | 940 |     |     |     |     |
| Gly | Gly | Asn | Cys | His | Leu | Thr | Val | Asn | Gly | Glu | Asp | Val | Gly | Ala | Phe |
| 945 |     |     |     |     | 950 |     |     |     |     | 955 |     |     |     |     | 960 |
| Pro | Pro | Gly | Lys | Phe | Val | Thr | Ala | Ala | Leu | Leu | Asn | Thr | Pro | Pro | Pro |
|     |     |     | 965 |     |     |     |     | 970 |     |     |     |     | 975 |     |     |
| Tyr | Gln | Val | Ser | Cys | Gly | Gly | Glu | Ser | Asp | Arg | Ala | Ser | Ala | Gly | His |
|     |     |     | 980 |     |     |     |     | 985 |     |     |     |     | 990 |     |     |

( 2 ) INFORMATION FOR SEQ ID NO:2:

( i ) SEQUENCE CHARACTERISTICS:
        ( A ) LENGTH: 21 amino acids
        ( B ) TYPE: amino acid (C) STRANDEDNESS:
(D) TOPOLOGY: unknown (xi) SEQUENCE DESCRIPTION: SEQ ID NO:2:

Pro Ser Arg Ala Pro Pro Gln Gln Pro Gln Pro Pro Arg Met Gln Thr
1               5                   10                  15

Gly Arg Gly Gly Ser
            20

(2) INFORMATION FOR SEQ ID NO:3:

(i) SEQUENCE CHARACTERISTICS:
    (A) LENGTH: 7 amino acids
    (B) TYPE: amino acid
    (C) STRANDEDNESS:
    (D) TOPOLOGY: unknown (xi) SEQUENCE DESCRIPTION: SEQ ID NO:3:

Gln Pro Gln Pro Pro Arg Met
1               5

(2) INFORMATION FOR SEQ ID NO:4:

(i) SEQUENCE CHARACTERISTICS:
    (A) LENGTH: 21 amino acids
    (B) TYPE: amino acid
    (C) STRANDEDNESS:
    (D) TOPOLOGY: unknown (xi) SEQUENCE DESCRIPTION: SEQ ID NO:4:

Glu Arg Gln Glu Ser Arg Ser Gln Thr Pro Ala Pro Lys Pro Ser Arg
1               5                   10                  15

Ala Pro Pro Gln Gln
            20

(2) INFORMATION FOR SEQ ID NO:5:

(i) SEQUENCE CHARACTERISTICS:
    (A) LENGTH: 7 amino acids
    (B) TYPE: amino acid
    (C) STRANDEDNESS:
    (D) TOPOLOGY: unknown (xi) SEQUENCE DESCRIPTION: SEQ ID NO:5:

Gln Thr Pro Ala Pro Lys Pro
1               5

(2) INFORMATION FOR SEQ ID NO:6:

(i) SEQUENCE CHARACTERISTICS:
    (A) LENGTH: 21 amino acids
    (B) TYPE: amino acid
    (C) STRANDEDNESS:
    (D) TOPOLOGY: unknown (xi) SEQUENCE DESCRIPTION: SEQ ID NO:6:

Asp Met Ala Ala Pro Pro Met Pro Pro Gln Pro Pro Arg Ala His Gly
1               5                   10                  15

Gln His Tyr Gly His
            20

(2) INFORMATION FOR SEQ ID NO:7:

(i) SEQUENCE CHARACTERISTICS:
    (A) LENGTH: 7 amino acids
    (B) TYPE: amino acid
    (C) STRANDEDNESS:

5,510,264

-continued ( D ) TOPOLOGY: unknown ( x i ) SEQUENCE DESCRIPTION: SEQ ID NO:7:

```
Pro Pro Gln Pro Pro Arg Ala
1               5
```

( 2 ) INFORMATION FOR SEQ ID NO:8:

( i ) SEQUENCE CHARACTERISTICS:
        ( A ) LENGTH: 1063 amino acids
        ( B ) TYPE: amino acid
        ( C ) STRANDEDNESS:
        ( D ) TOPOLOGY: unknown ( x i ) SEQUENCE DESCRIPTION: SEQ ID NO:8:

```
Met Ala Ser Thr Thr Pro Ile Thr Met Glu Asp Leu Gln Lys Ala Leu
1               5                   10                  15

Glu Ala Gln Ser Arg Ala Leu Arg Ala Glu Leu Ala Ala Gly Ala Ser
                20                  25                  30

Gln Ser Arg Arg Pro Arg Pro Pro Arg Gln Arg Asp Ser Ser Thr Ser
            35                  40                  45

Gly Asp Asp Ser Gly Arg Asp Ser Gly Gly Pro Arg Arg Arg Arg Gly
        50                  55                  60

Asn Arg Gly Arg Gly Gln Arg Arg Asp Trp Ser Arg Ala Pro Pro Pro
65                  70                  75                  80

Pro Glu Glu Arg Gln Glu Ser Arg Ser Gln Thr Pro Ala Pro Lys Pro
                85                  90                  95

Ser Arg Ala Pro Pro Gln Gln Pro Gln Pro Pro Arg Met Gln Thr Gly
                100                 105                 110

Arg Gly Gly Ser Ala Pro Arg Pro Glu Leu Gly Pro Pro Thr Asn Pro
            115                 120                 125

Phe Gln Ala Ala Val Ala Arg Gly Leu Arg Pro Pro Leu His Asp Pro
        130                 135                 140

Asp Thr Glu Ala Pro Thr Glu Ala Cys Val Thr Ser Trp Leu Trp Ser
145                 150                 155                 160

Glu Gly Gln Gly Ala Val Phe Tyr Arg Val Asp Leu His Phe Thr Asn
                165                 170                 175

Leu Gly Thr Pro Pro Leu Asp Glu Asp Gly Arg Trp Asp Pro Ala Leu
                180                 185                 190

Met Tyr Asn Pro Cys Gly Pro Glu Pro Pro Ala His Val Val Arg Ala
            195                 200                 205

Tyr Asn Gln Pro Ala Gly Asp Val Arg Gly Val Trp Gly Lys Gly Glu
        210                 215                 220

Arg Thr Tyr Ala Glu Gln Asp Phe Arg Val Gly Gly Thr Arg Trp His
225                 230                 235                 240

Arg Leu Leu Arg Met Pro Val Arg Gly Leu Asp Gly Asp Ser Ala Pro
                245                 250                 255

Leu Pro Pro His Thr Thr Glu Arg Ile Glu Thr Arg Ser Ala Arg His
                260                 265                 270

Pro Trp Arg Ile Arg Phe Gly Ala Pro Gln Ala Phe Leu Ala Gly Leu
            275                 280                 285

Leu Leu Ala Thr Val Ala Val Gly Thr Ala Arg Ala Gly Leu Gln Pro
        290                 295                 300

Arg Ala Asp Met Ala Ala Pro Pro Thr Leu Pro Gln Pro Pro Cys Ala
305                 310                 315                 320

His Gly Gln His Tyr Gly His His His Gln Leu Pro Phe Leu Gly
                325                 330                 335
```

```
His  Asp  Gly  His  His  Gly  Gly  Thr  Leu  Arg  Val  Gly  Gln  His  Tyr  Arg
          340                      345                      350

Asn  Ala  Ser  Asp  Val  Leu  Pro  Gly  His  Trp  Leu  Gln  Gly  Gly  Trp  Gly
          355                      360                      365

Cys  Tyr  Asn  Leu  Ser  Asp  Trp  His  Gln  Gly  Thr  His  Val  Cys  His  Thr
     370                      375                      380

Lys  His  Met  Asp  Phe  Trp  Cys  Val  Glu  His  Ala  Arg  Pro  Pro  Pro  Ala
385                      390                      395                      400

Thr  Pro  Thr  Pro  Leu  Thr  Thr  Ala  Ala  Asn  Ser  Thr  Thr  Ala  Ala  Thr
               405                      410                      415

Pro  Ala  Thr  Ala  Pro  Ala  Pro  Cys  His  Ala  Gly  Leu  Asn  Asp  Ser  Cys
               420                      425                      430

Gly  Gly  Phe  Leu  Ser  Gly  Cys  Gly  Pro  Met  Arg  Leu  Arg  His  Gly  Ala
          435                      440                      445

Asp  Thr  Arg  Cys  Gly  Arg  Leu  Ile  Cys  Gly  Leu  Ser  Thr  Thr  Ala  Gln
     450                      455                      460

Tyr  Pro  Pro  Thr  Arg  Phe  Gly  Cys  Ala  Met  Arg  Trp  Gly  Leu  Pro  Pro
465                      470                      475                      480

Trp  Glu  Leu  Val  Val  Leu  Thr  Ala  Arg  Pro  Glu  Asp  Gly  Trp  Thr  Cys
               485                      490                      495

Arg  Gly  Val  Pro  Ala  His  Pro  Gly  Ala  Arg  Cys  Pro  Glu  Leu  Val  Ser
               500                      505                      510

Pro  Met  Gly  Arg  Ala  Thr  Cys  Ser  Pro  Ala  Ser  Ala  Leu  Trp  Leu  Ala
          515                      520                      525

Thr  Ala  Asn  Ala  Leu  Ser  Leu  Asp  His  Ala  Leu  Ala  Ala  Phe  Val  Leu
     530                      535                      540

Ser  Val  Pro  Trp  Val  Leu  Ile  Phe  Met  Val  Cys  Arg  Arg  Ala  Cys  Arg
545                      550                      555                      560

Arg  Arg  Gly  Ala  Ala  Ala  Ala  Leu  Thr  Ala  Val  Val  Leu  Gln  Gly  Tyr
               565                      570                      575

Asn  Pro  Pro  Ala  Tyr  Gly  Glu  Glu  Ala  Phe  Thr  Tyr  Leu  Cys  Thr  Ala
               580                      585                      590

Pro  Gly  Cys  Ala  Thr  Gln  Ala  Pro  Val  Pro  Val  Arg  Leu  Ala  Gly  Val
          595                      600                      605

Arg  Phe  Glu  Ser  Lys  Ile  Val  Asp  Gly  Gly  Cys  Phe  Ala  Pro  Trp  Asp
     610                      615                      620

Leu  Glu  Ala  Thr  Gly  Ala  Cys  Ile  Cys  Glu  Ile  Pro  Thr  Asp  Val  Ser
625                      630                      635                      640

Cys  Glu  Gly  Leu  Gly  Ala  Trp  Val  Pro  Ala  Ala  Pro  Cys  Ala  Arg  Ile
               645                      650                      655

Trp  Asn  Gly  Thr  Gln  Arg  Ala  Cys  Thr  Phe  Trp  Ala  Val  Asn  Ala  Tyr
               660                      665                      670

Ser  Ser  Gly  Gly  Tyr  Ala  Gln  Leu  Ala  Ser  Tyr  Phe  Asn  Pro  Gly  Gly
          675                      680                      685

Ser  Tyr  Tyr  Lys  Gln  Tyr  His  Pro  Thr  Ala  Cys  Glu  Val  Glu  Pro  Ala
     690                      695                      700

Phe  Gly  His  Ser  Asp  Ala  Ala  Cys  Trp  Gly  Phe  Pro  Thr  Asp  Thr  Val
705                      710                      715                      720

Met  Ser  Val  Phe  Ala  Leu  Ala  Ser  Tyr  Val  Gln  His  Pro  His  Lys  Thr
               725                      730                      735

Val  Arg  Val  Lys  Phe  His  Thr  Glu  Thr  Arg  Thr  Val  Trp  Gln  Leu  Ser
               740                      745                      750

Val  Ala  Gly  Val  Ser  Cys  Asn  Val  Thr  Thr  Glu  His  Pro  Phe  Cys  Asn
```

|     |     |     |     | 755 |     |     |     |     | 760 |     |     |     |     | 765 |     |
| --- | --- | --- | --- | --- | --- | --- | --- | --- | --- | --- | --- | --- | --- | --- | --- |

Thr Pro His Gly Gln Leu Glu Val Gln Val Pro Pro Asp Pro Gly Asp
         770             775             780

Leu Val Glu Tyr Ile Met Asn Tyr Thr Gly Asn Gln Gln Ser Arg Trp
785             790             795                         800

Gly Leu Gly Ser Pro Asn Cys His Gly Pro Asp Trp Ala Ser Pro Val
             805             810             815

Cys Gln Arg His Ser Pro Asp Cys Ser Arg Leu Val Gly Ala Thr Pro
             820             825             830

Glu Arg Pro Arg Leu Arg Leu Val Asp Ala Asp Asp Pro Leu Leu Arg
         835             840             845

Thr Ala Pro Gly Pro Gly Glu Val Trp Val Thr Pro Val Ile Gly Ser
     850             855             860

Gln Ala Arg Lys Cys Gly Leu His Ile Arg Ala Gly Pro Tyr Gly His
865             870             875             880

Ala Thr Val Glu Met Pro Glu Trp Ile His Ala His Thr Thr Ser Asp
             885             890             895

Pro Trp His Pro Pro Gly Pro Leu Gly Leu Lys Phe Lys Thr Val Arg
         900             905             910

Pro Val Ala Leu Pro Arg Thr Leu Ala Pro Pro Arg Asn Val Arg Val
         915             920             925

Thr Gly Cys Tyr Gln Cys Gly Thr Pro Ala Leu Val Glu Gly Leu Ala
     930             935             940

Pro Gly Gly Gly Asn Cys His Leu Thr Val Asn Gly Glu Asp Val Gly
945             950             955             960

Ala Val Pro Pro Gly Lys Phe Val Thr Ala Ala Leu Leu Asn Thr Pro
             965             970             975

Pro Pro Tyr Gln Val Ser Cys Gly Gly Glu Ser Asp Arg Ala Ser Ala
         980             985             990

Arg Val Ile Asp Pro Ala Ala Gln Ser Phe Thr Gly Val Val Tyr Gly
         995             1000            1005

Thr His Thr Thr Ala Val Ser Glu Thr Arg Gln Thr Trp Ala Glu Trp
    1010            1015            1020

Ala Ala Ala His Trp Trp Gln Leu Thr Leu Gly Ala Thr Cys Ala Leu
1025            1030            1035            1040

Pro Leu Ala Gly Leu Leu Ala Cys Cys Ala Lys Cys Leu Tyr Tyr Leu
             1045            1050            1055

Arg Gly Ala Ile Ala Pro Arg
             1060

( 2 ) INFORMATION FOR SEQ ID NO:9:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: unknown ( x i ) SEQUENCE DESCRIPTION: SEQ ID NO:9:

Asp Met Ala Ala Pro Pro Thr Leu Pro Gln Pro Pro Arg Ala His Gly
1               5                       10                      15

Gln His Tyr Gly His
            20

( 2 ) INFORMATION FOR SEQ ID NO:10:

( i ) SEQUENCE CHARACTERISTICS:

(A) LENGTH: 7 amino acids
(B) TYPE: amino acid
(C) STRANDEDNESS:
(D) TOPOLOGY: unknown (xi) SEQUENCE DESCRIPTION: SEQ ID NO:10:

| Leu | Pro | Gln | Pro | Pro | Cys | Ala |
|---|---|---|---|---|---|---|
| 1 | | | | 5 | | |

(2) INFORMATION FOR SEQ ID NO:11:

(i) SEQUENCE CHARACTERISTICS:
(A) LENGTH: 478 amino acids
(B) TYPE: amino acid
(C) STRANDEDNESS:
(D) TOPOLOGY: unknown (xi) SEQUENCE DESCRIPTION: SEQ ID NO:11:

| Met | Gly | Ala | Arg | Ala | Ser | Val | Leu | Ser | Gly | Gly | Glu | Leu | Asp | Arg | Trp |
|---|---|---|---|---|---|---|---|---|---|---|---|---|---|---|---|
| 1 | | | | 5 | | | | | 10 | | | | | 15 | |
| Glu | Lys | Ile | Arg | Leu | Arg | Pro | Gly | Gly | Lys | Lys | Tyr | Lys | Leu | Lys | |
| | | | 20 | | | | | 25 | | | | 30 | | | |
| His | Ile | Val | Trp | Ala | Ser | Arg | Glu | Leu | Glu | Arg | Phe | Ala | Val | Asn | Pro |
| | | | 35 | | | | 40 | | | | | 45 | | | |
| Gly | Leu | Leu | Glu | Thr | Ser | Glu | Gly | Cys | Arg | Gln | Ile | Leu | Gly | Gln | Leu |
| | 50 | | | | | 55 | | | | | | 60 | | | |
| Gln | Pro | Ser | Leu | Gln | Thr | Gly | Ser | Glu | Glu | Leu | Arg | Ser | Leu | Tyr | Asn |
| 65 | | | | | 70 | | | | | 75 | | | | | 80 |
| Thr | Val | Ala | Thr | Leu | Tyr | Cys | Val | His | Gln | Arg | Ile | Glu | Ile | Lys | Asp |
| | | | | 85 | | | | | 90 | | | | | 95 | |
| Thr | Lys | Glu | Ala | Leu | Asp | Lys | Ile | Glu | Glu | Glu | Gln | Asn | Lys | Ser | Lys |
| | | | 100 | | | | | 105 | | | | | 110 | | |
| Lys | Lys | Ala | Gln | Gln | Ala | Ala | Ala | Asp | Thr | Gly | His | Ser | Ser | Gln | Val |
| | | | 115 | | | | 120 | | | | | 125 | | | |
| Ser | Gln | Asn | Tyr | Pro | Ile | Val | Gln | Asn | Ile | Gln | Gly | Gln | Met | Val | His |
| | 130 | | | | | 135 | | | | | 140 | | | | |
| Gln | Ala | Ile | Ser | Pro | Arg | Thr | Leu | Asn | Ala | Trp | Val | Lys | Val | Val | Glu |
| 145 | | | | | 150 | | | | | 155 | | | | | 160 |
| Glu | Lys | Ala | Phe | Ser | Pro | Glu | Val | Ile | Pro | Met | Phe | Ser | Ala | Leu | Ser |
| | | | | 165 | | | | | 170 | | | | | 175 | |
| Glu | Gly | Ala | Thr | Pro | Gln | Asp | Leu | Asn | Thr | Met | Leu | Asn | Thr | Val | Gly |
| | | | | 180 | | | | | 185 | | | | | 190 | |
| Gly | His | Gln | Ala | Ala | Met | Gln | Met | Leu | Lys | Glu | Thr | Ile | Asn | Glu | Glu |
| | | | | 195 | | | | | 200 | | | | | 205 | |
| Ala | Ala | Glu | Trp | Asp | Arg | Val | His | Pro | Val | His | Ala | Gly | Pro | Ile | Ala |
| | 210 | | | | | 215 | | | | | 220 | | | | |
| Pro | Gly | Gln | Met | Arg | Glu | Pro | Arg | Gly | Ser | Asp | Ile | Ala | Gly | Thr | Thr |
| 225 | | | | | 230 | | | | | 235 | | | | | 240 |
| Ser | Thr | Leu | Gln | Glu | Gln | Ile | Gly | Trp | Met | Thr | Asn | Asn | Pro | Pro | Ile |
| | | | | 245 | | | | | 250 | | | | | 255 | |
| Pro | Val | Gly | Glu | Ile | Tyr | Lys | Arg | Trp | Ile | Ile | Leu | Gly | Leu | Asn | Lys |
| | | | | 260 | | | | | 265 | | | | | 270 | |
| Ile | Val | Arg | Met | Tyr | Ser | Pro | Thr | Ser | Ile | Leu | Asp | Ile | Arg | Gln | Gly |
| | | | 275 | | | | | 280 | | | | | 285 | | |
| Pro | Lys | Glu | Pro | Phe | Arg | Asp | Tyr | Val | Asp | Arg | Phe | Tyr | Lys | Thr | Leu |
| | 290 | | | | | 295 | | | | | 300 | | | | |
| Arg | Ala | Glu | Gln | Ala | Ser | Gln | Glu | Val | Lys | Asn | Trp | Met | Thr | Glu | Thr |
| 305 | | | | | 310 | | | | | 315 | | | | | 320 |

```
        Leu  Leu  Val  Gln  Asn  Ala  Asn  Pro  Asp  Cys  Lys  Thr  Ile  Leu  Lys  Ala
                            325                      330                      335

Leu  Gly  Pro  Ala  Ala  Thr  Leu  Glu  Glu  Met  Met  Thr  Ala  Cys  Gln  Gly
                       340                      345                      350

Val  Gly  Gly  Pro  Gly  His  Lys  Ala  Arg  Val  Leu  Ala  Glu  Ala  Met  Ser
                  355                           360                      365

Gln  Val  Thr  Asn  Thr  Ala  Thr  Ile  Met  Met  Gln  Arg  Gly  Asn  Phe  Arg
             370                      375                      380

Asn  Gln  Arg  Lys  Met  Val  Lys  Cys  Phe  Asn  Cys  Gly  Lys  Glu  Gly  His
        385                      390                      395                      400

Thr  Ala  Arg  Asn  Cys  Arg  Ala  Pro  Arg  Lys  Lys  Gly  Cys  Trp  Lys  Cys
                            405                      410                      415

Gly  Lys  Glu  Gly  His  Gln  Met  Lys  Asp  Cys  Thr  Glu  Arg  Gln  Ala  Asn
                       420                      425                      430

Phe  Leu  Gly  Lys  Ile  Cys  Leu  Pro  Thr  Arg  Glu  Gly  Gln  Gly  Ile  Phe
                       435                      440                      445

Phe  Arg  Ala  Asp  Gln  Ser  Gln  Gln  Pro  His  His  Phe  Phe  Arg  Ala  Asp
                  450                      455                      460

Gln  Ser  Gln  Gln  Pro  His  Gln  Lys  Arg  Ala  Ser  Gly  Leu  Gly
        465                      470                      475
```

( 2 ) INFORMATION FOR SEQ ID NO:12:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: unknown ( x i ) SEQUENCE DESCRIPTION: SEQ ID NO:12:

```
        Ile  Gln  Gly  Gln  Met  Val  His  Gln  Ala  Ile  Ser  Pro  Arg  Thr  Leu  Asn
        1                 5                      10                      15

Ala  Trp  Val  Lys  Val
                       20
```

( 2 ) INFORMATION FOR SEQ ID NO:13:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: unknown ( x i ) SEQUENCE DESCRIPTION: SEQ ID NO:13:

```
        Gln  Ala  Ile  Ser  Pro  Arg  Thr
        1                 5
```

( 2 ) INFORMATION FOR SEQ ID NO:14:

( i ) SEQUENCE CHARACTERISTICS:
        ( A ) LENGTH: 861 amino acids
        ( B ) TYPE: amino acid
        ( C ) STRANDEDNESS:
        ( D ) TOPOLOGY: unknown ( x i ) SEQUENCE DESCRIPTION: SEQ ID NO:14:

```
        Met  Arg  Val  Lys  Glu  Lys  Tyr  Gln  His  Leu  Trp  Arg  Trp  Gly  Trp  Lys
        1                 5                      10                      15

Trp  Gly  Thr  Met  Leu  Leu  Gly  Ile  Leu  Met  Ile  Cys  Ser  Ala  Thr  Glu
                       20                      25                      30

Lys  Leu  Trp  Val  Thr  Val  Tyr  Tyr  Gly  Val  Pro  Val  Trp  Lys  Glu  Ala
```

```
             35                          40                          45

Thr  Thr  Thr  Leu  Phe  Cys  Ala  Ser  Asp  Ala  Lys  Ala  Tyr  Asp  Thr  Glu
          50                    55                    60

Val  His  Asn  Val  Trp  Ala  Thr  His  Ala  Cys  Val  Pro  Thr  Asp  Pro  Asn
65                       70                    75                          80

Pro  Gln  Glu  Val  Val  Leu  Val  Asn  Val  Thr  Glu  Asn  Phe  Asn  Met  Trp
                    85                      90                          95

Lys  Asn  Asp  Met  Val  Glu  Gln  Met  His  Glu  Asp  Ile  Ile  Ser  Leu  Trp
               100                    105                         110

Asp  Gln  Ser  Leu  Lys  Pro  Cys  Val  Lys  Leu  Thr  Pro  Leu  Cys  Val  Ser
               115                    120                    125

Leu  Lys  Cys  Thr  Asp  Leu  Gly  Asn  Ala  Thr  Asn  Thr  Asn  Ser  Ser  Asn
     130                         135                    140

Thr  Asn  Ser  Ser  Ser  Gly  Glu  Met  Met  Met  Glu  Lys  Gly  Glu  Ile  Lys
145                         150                    155                         160

Asn  Cys  Ser  Phe  Asn  Ile  Ser  Thr  Ser  Ile  Arg  Gly  Lys  Val  Gln  Lys
                    165                    170                         175

Glu  Tyr  Ala  Phe  Phe  Tyr  Lys  Leu  Asp  Ile  Ile  Pro  Ile  Asp  Asn  Asp
               180                    185                    190

Thr  Thr  Ser  Tyr  Thr  Leu  Thr  Ser  Cys  Asn  Thr  Ser  Val  Ile  Thr  Gln
          195                    200                    205

Ala  Cys  Pro  Lys  Val  Ser  Phe  Glu  Pro  Ile  Pro  Ile  His  Tyr  Cys  Ala
     210                    215                    220

Pro  Ala  Gly  Phe  Ala  Ile  Leu  Lys  Cys  Asn  Asn  Lys  Thr  Phe  Asn  Gly
225                         230                    235                         240

Thr  Gly  Pro  Cys  Thr  Asn  Val  Ser  Thr  Val  Gln  Cys  Thr  His  Gly  Ile
               245                    250                         255

Arg  Pro  Val  Val  Ser  Thr  Gln  Leu  Leu  Leu  Asn  Gly  Ser  Leu  Ala  Glu
               260                    265                    270

Glu  Glu  Val  Val  Ile  Arg  Ser  Ala  Asn  Phe  Thr  Asp  Asn  Ala  Lys  Thr
          275                    280                    285

Ile  Ile  Val  Gln  Leu  Asn  Gln  Ser  Val  Glu  Ile  Asn  Cys  Thr  Arg  Pro
     290                    295                    300

Asn  Asn  Asn  Thr  Arg  Lys  Ser  Ile  Arg  Ile  Gln  Arg  Gly  Pro  Gly  Arg
305                         310                    315                         320

Ala  Phe  Val  Thr  Ile  Gly  Lys  Ile  Gly  Asn  Met  Arg  Gln  Ala  His  Cys
                    325                    330                         335

Asn  Ile  Ser  Arg  Ala  Lys  Trp  Asn  Ala  Thr  Leu  Lys  Gln  Ile  Ala  Ser
               340                    345                         350

Lys  Leu  Arg  Glu  Gln  Phe  Gly  Asn  Asn  Lys  Thr  Ile  Ile  Phe  Lys  Gln
          355                    360                    365

Ser  Ser  Gly  Gly  Asp  Pro  Glu  Ile  Val  Thr  His  Ser  Phe  Asn  Cys  Gly
     370                    375                    380

Gly  Glu  Phe  Phe  Tyr  Cys  Asn  Ser  Thr  Gln  Leu  Phe  Asn  Ser  Thr  Trp
385                         390                    395                         400

Phe  Asn  Ser  Thr  Trp  Ser  Thr  Glu  Gly  Ser  Asn  Asn  Thr  Glu  Gly  Ser
               405                    410                         415

Asp  Thr  Ile  Thr  Leu  Pro  Cys  Arg  Ile  Lys  Gln  Phe  Ile  Asn  Met  Trp
               420                    425                    430

Gln  Glu  Val  Gly  Lys  Ala  Met  Tyr  Ala  Pro  Pro  Ile  Ser  Gly  Gln  Ile
          435                    440                    445

Arg  Cys  Ser  Ser  Asn  Ile  Thr  Gly  Leu  Leu  Leu  Thr  Arg  Asp  Gly  Gly
     450                    455                    460
```

```
Asn Asn Asn Asn Gly Ser Glu Ile Phe Arg Pro Gly Gly Gly Asp Met
465             470                 475                 480

Arg Asp Asn Trp Arg Ser Glu Leu Tyr Lys Tyr Lys Val Val Lys Ile
            485             490                 495

Glu Pro Leu Gly Val Ala Pro Thr Lys Ala Lys Arg Val Val Gln
            500             505                 510

Arg Glu Lys Arg Ala Val Gly Ile Gly Ala Leu Phe Leu Gly Phe Leu
        515             520                 525

Gly Ala Ala Gly Ser Thr Met Gly Ala Arg Ser Met Thr Leu Thr Val
    530             535                 540

Gln Ala Arg Gln Leu Leu Ser Gly Ile Val Gln Gln Asn Asn Leu
545             550             555                 560

Leu Arg Ala Ile Glu Ala Gln Gln His Leu Leu Gln Leu Thr Val Trp
                565             570                 575

Gly Ile Lys Gln Leu Gln Ala Arg Ile Leu Ala Val Glu Arg Tyr Leu
            580             585                 590

Lys Asp Gln Gln Leu Leu Gly Ile Trp Gly Cys Ser Gly Lys Leu Ile
        595             600                 605

Cys Thr Thr Ala Val Pro Trp Asn Ala Ser Trp Ser Asn Lys Ser Leu
    610             615                 620

Glu Gln Ile Trp Asn Asn Met Thr Trp Met Glu Trp Asp Arg Glu Ile
625             630             635                 640

Asn Asn Tyr Thr Ser Leu Ile His Ser Leu Ile Glu Glu Ser Gln Asn
            645             650                 655

Gln Gln Glu Lys Asn Glu Gln Glu Leu Leu Glu Leu Asp Lys Trp Ala
        660             665                 670

Ser Leu Trp Asn Trp Phe Asn Ile Thr Asn Trp Leu Trp Tyr Ile Lys
        675             680                 685

Ile Phe Ile Met Ile Val Gly Gly Leu Val Gly Leu Arg Ile Val Phe
    690             695             700

Ala Val Leu Ser Ile Val Asn Arg Val Arg Gln Gly Tyr Ser Pro Leu
705             710             715                 720

Ser Phe Gln Thr His Leu Pro Thr Pro Arg Gly Pro Asp Arg Pro Glu
            725             730                 735

Gly Ile Glu Glu Glu Gly Gly Glu Arg Asp Arg Asp Arg Ser Ile Arg
        740             745                 750

Leu Val Asn Gly Ser Leu Ala Leu Ile Trp Asp Asp Leu Arg Ser Leu
        755             760                 765

Cys Leu Phe Ser Tyr His Arg Leu Arg Asp Leu Leu Leu Ile Val Thr
    770             775                 780

Arg Ile Val Glu Leu Leu Gly Arg Arg Gly Trp Glu Ala Leu Lys Tyr
785             790             795                 800

Trp Trp Asn Leu Leu Gln Tyr Trp Ser Gln Glu Leu Lys Asn Ser Ala
            805             810                 815

Val Ser Leu Leu Asn Ala Thr Ala Ile Ala Val Ala Glu Gly Thr Asp
            820             825                 830

Arg Val Ile Glu Val Val Gln Gly Ala Cys Arg Ala Ile Arg His Ile
        835             840                 845

Pro Arg Arg Ile Arg Gln Gly Leu Glu Arg Ile Leu Leu
850             855                 860
```

( 2 ) INFORMATION FOR SEQ ID NO:15:

( i ) SEQUENCE CHARACTERISTICS:
        ( A ) LENGTH: 21 amino acids (B) TYPE: amino acid
(C) STRANDEDNESS:
(D) TOPOLOGY: unknown (xi) SEQUENCE DESCRIPTION: SEQ ID NO:15:

| His | Ser | Leu | Ile | Glu | Glu | Ser | Gln | Asn | Gln | Gln | Glu | Lys | Asn | Glu | Gln |
|---|---|---|---|---|---|---|---|---|---|---|---|---|---|---|---|
| 1 | | | | 5 | | | | | 10 | | | | | 15 | |

| Glu | Leu | Leu | Glu | Leu |
|---|---|---|---|---|
| | | | 20 | |

(2) INFORMATION FOR SEQ ID NO:16:

(i) SEQUENCE CHARACTERISTICS:
(A) LENGTH: 7 amino acids
(B) TYPE: amino acid
(C) STRANDEDNESS:
(D) TOPOLOGY: unknown (xi) SEQUENCE DESCRIPTION: SEQ ID NO:16:

| Gln | Asn | Gln | Gln | Glu | Lys | Asn |
|---|---|---|---|---|---|---|
| 1 | | | | 5 | | |

(2) INFORMATION FOR SEQ ID NO:17:

(i) SEQUENCE CHARACTERISTICS:
(A) LENGTH: 274 amino acids
(B) TYPE: amino acid
(C) STRANDEDNESS:
(D) TOPOLOGY: unknown (xi) SEQUENCE DESCRIPTION: SEQ ID NO:17:

| Met | Lys | Thr | Thr | Leu | Lys | Met | Thr | Ala | Leu | Ala | Ala | Leu | Ser | Ala | Phe |
|---|---|---|---|---|---|---|---|---|---|---|---|---|---|---|---|
| 1 | | | | 5 | | | | | 10 | | | | | 15 | |

| Val | Leu | Ala | Gly | Cys | Gly | Ser | His | Gln | Met | Lys | Ser | Glu | Glu | His | Ala |
|---|---|---|---|---|---|---|---|---|---|---|---|---|---|---|---|
| | | | 20 | | | | | 25 | | | | | 30 | | |

| Asn | Met | Gln | Leu | Gln | Gln | Gln | Ala | Val | Leu | Gly | Leu | Asn | Trp | Met | Gln |
|---|---|---|---|---|---|---|---|---|---|---|---|---|---|---|---|
| | | 35 | | | | | 40 | | | | | 45 | | | |

| Asp | Ser | Gly | Glu | Tyr | Lys | Ala | Leu | Ala | Tyr | Gln | Ala | Tyr | Asn | Ala | Ala |
|---|---|---|---|---|---|---|---|---|---|---|---|---|---|---|---|
| | 50 | | | | | 55 | | | | | 60 | | | | |

| Lys | Val | Ala | Phe | Asp | His | Ala | Lys | Val | Ala | Lys | Gly | Lys | Lys | Lys | Ala |
|---|---|---|---|---|---|---|---|---|---|---|---|---|---|---|---|
| 65 | | | | | 70 | | | | | 75 | | | | | 80 |

| Val | Val | Ala | Asp | Leu | Asp | Glu | Thr | Met | Leu | Asp | Asn | Ser | Pro | Tyr | Ala |
|---|---|---|---|---|---|---|---|---|---|---|---|---|---|---|---|
| | | | | 85 | | | | | 90 | | | | | 95 | |

| Gly | Trp | Gln | Val | Gln | Asn | Asn | Lys | Pro | Phe | Asp | Gly | Lys | Asp | Trp | Thr |
|---|---|---|---|---|---|---|---|---|---|---|---|---|---|---|---|
| | | | 100 | | | | | 105 | | | | | 110 | | |

| Arg | Trp | Val | Asp | Ala | Arg | Gln | Ser | Arg | Ala | Val | Pro | Gly | Ala | Val | Glu |
|---|---|---|---|---|---|---|---|---|---|---|---|---|---|---|---|
| | | 115 | | | | | 120 | | | | | 125 | | | |

| Phe | Asn | Asn | Tyr | Val | Asn | Ser | His | Asn | Gly | Lys | Val | Phe | Tyr | Val | Thr |
|---|---|---|---|---|---|---|---|---|---|---|---|---|---|---|---|
| | 130 | | | | | 135 | | | | | 140 | | | | |

| Asn | Arg | Lys | Asp | Ser | Thr | Glu | Lys | Ser | Gly | Thr | Ile | Asp | Asp | Met | Lys |
|---|---|---|---|---|---|---|---|---|---|---|---|---|---|---|---|
| 145 | | | | | 150 | | | | | 155 | | | | | 160 |

| Arg | Leu | Gly | Phe | Asn | Gly | Val | Glu | Glu | Ser | Ala | Phe | Tyr | Leu | Lys | Lys |
|---|---|---|---|---|---|---|---|---|---|---|---|---|---|---|---|
| | | | | 165 | | | | | 170 | | | | | 175 | |

| Asp | Lys | Ser | Ala | Lys | Ala | Ala | Arg | Phe | Ala | Glu | Ile | Glu | Lys | Gln | Gly |
|---|---|---|---|---|---|---|---|---|---|---|---|---|---|---|---|
| | | | 180 | | | | | 185 | | | | | 190 | | |

| Tyr | Glu | Ile | Val | Leu | Tyr | Val | Gly | Asp | Asn | Leu | Asp | Asp | Phe | Gly | Asn |
|---|---|---|---|---|---|---|---|---|---|---|---|---|---|---|---|
| | | 195 | | | | | 200 | | | | | 205 | | | |

| Thr | Val | Tyr | Gly | Lys | Leu | Asn | Ala | Asp | Arg | Arg | Ala | Phe | Val | Asp | Gln |
|---|---|---|---|---|---|---|---|---|---|---|---|---|---|---|---|
| | 210 | | | | | 215 | | | | | 220 | | | | |

| Asn | Gln | Gly | Lys | Phe | Gly | Lys | Thr | Phe | Ile | Met | Leu | Pro | Asn | Ala | Asn |
|---|---|---|---|---|---|---|---|---|---|---|---|---|---|---|---|

5,510,264

-continued

```
          225                     230                     235                     240
     Tyr  Gly  Gly  Trp  Glu  Gly  Gly  Leu  Ala  Glu  Gly  Tyr  Phe  Lys  Lys  Asp
                         245                     250                     255
     Thr  Gln  Gly  Gln  Ile  Lys  Ala  Arg  Leu  Asp  Ala  Val  Gln  Ala  Trp  Asp
                         260                     265                     270
     Gly  Lys
```

(2) INFORMATION FOR SEQ ID NO:18:

(i) SEQUENCE CHARACTERISTICS:
        (A) LENGTH: 21 amino acids
        (B) TYPE: amino acid
        (C) STRANDEDNESS:
        (D) TOPOLOGY: unknown (xi) SEQUENCE DESCRIPTION: SEQ ID NO:18:

```
     Asn  Ser  Pro  Tyr  Ala  Gly  Trp  Gln  Val  Gln  Asn  Asn  Lys  Pro  Phe  Asp
     1                   5                        10                      15
     Gly  Lys  Asp  Trp  Thr
                    20
```

(2) INFORMATION FOR SEQ ID NO:19:

(i) SEQUENCE CHARACTERISTICS:
        (A) LENGTH: 7 amino acids
        (B) TYPE: amino acid
        (C) STRANDEDNESS:
        (D) TOPOLOGY: unknown (xi) SEQUENCE DESCRIPTION: SEQ ID NO:19:

```
     Gln  Val  Gln  Asn  Asn  Lys  Pro
     1                   5
```

(2) INFORMATION FOR SEQ ID NO:20:

(i) SEQUENCE CHARACTERISTICS:
        (A) LENGTH: 170 amino acids
        (B) TYPE: amino acid
        (C) STRANDEDNESS:
        (D) TOPOLOGY: unknown (xi) SEQUENCE DESCRIPTION: SEQ ID NO:20:

```
     Ile  Gln  Pro  Pro  Lys  Asn  Leu  Leu  Phe  Ser  Ser  Leu  Leu  Phe  Ser  Ser
     1                   5                        10                      15
     Leu  Leu  Phe  Ser  Ser  Ala  Ala  Gln  Ala  Ala  Ser  Glu  Asp  Arg  Arg  Ser
                    20                       25                      30
     Pro  Tyr  Tyr  Val  Gln  Ala  Asp  Leu  Ala  Tyr  Ala  Ala  Glu  Arg  Ile  Thr
                    35                       40                      45
     His  Asp  Tyr  Pro  Gln  Ala  Thr  Gly  Ala  Asn  Asn  Thr  Ser  Thr  Val  Ser
          50                            55                 60
     Asp  Tyr  Phe  Arg  Asn  Ile  Arg  Ala  His  Ser  Ile  His  Pro  Arg  Val  Ser
     65                       70                      75                      80
     Val  Gly  Tyr  Asp  Phe  Gly  Gly  Trp  Arg  Ile  Ala  Ala  Asp  Tyr  Ala  Ser
                              85                      90                      95
     Tyr  Arg  Lys  Trp  Asn  Asn  Asn  Lys  Tyr  Ser  Val  Asn  Thr  Lys  Glu  Leu
                         100                     105                     110
     Glu  Asn  Lys  His  Asn  Asn  Lys  Lys  Asp  Leu  Lys  Thr  Glu  Asn  Gln  Glu
                    115                     120                     125
     Asn  Gly  Thr  Phe  His  Ala  Ala  Ser  Ser  Leu  Gly  Leu  Ser  Ala  Ile  Tyr
               130                      135                     140
     Asp  Phe  Lys  Leu  Lys  Gly  Lys  Phe  Lys  Pro  Tyr  Ile  Gly  Ala  Arg  Val
```

```
                    145                 150                 155                 160
              Ala Tyr Gly His Val Arg His Ser Ile Asp
                              165                 170
```

( 2 ) INFORMATION FOR SEQ ID NO:21:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: unknown ( x i ) SEQUENCE DESCRIPTION: SEQ ID NO:21:

```
              Ile Gln Pro Pro Lys Asn Leu Leu Phe Ser Ser Leu Leu
              1               5                   10
```

( 2 ) INFORMATION FOR SEQ ID NO:22:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: unknown ( x i ) SEQUENCE DESCRIPTION: SEQ ID NO:22:

```
              Ile Gln Pro Pro Lys Asn
              1               5
```

( 2 ) INFORMATION FOR SEQ ID NO:23:

( i ) SEQUENCE CHARACTERISTICS:
        ( A ) LENGTH: 695 amino acids
        ( B ) TYPE: amino acid
        ( C ) STRANDEDNESS:
        ( D ) TOPOLOGY: unknown ( x i ) SEQUENCE DESCRIPTION: SEQ ID NO:23:

```
       Lys Leu Met Ile Xaa Lys Phe Val Thr Lys Met Xaa Tyr Lys Thr Leu
       1               5                   10                  15

Asp Lys Tyr Leu Arg Arg Arg Leu Ile Leu Asn Ile Ser Ile Val Xaa
                       20                  25                  30

Lys Xaa Leu Ser Glu Lys Arg Xaa Ile Xaa Met Asn Lys Lys Lys Met
                   35              40                  45

Ile Leu Thr Ser Leu Ala Ser Val Ala Ile Leu Gly Ala Gly Phe Val
                   50                  55                  60

Ala Ser Gln Pro Thr Val Val Arg Ala Glu Glu Ser Pro Val Ala Ser
       65                  70                  75                  80

Gln Ser Lys Ala Glu Lys Asp Tyr Asp Ala Ala Lys Lys Asp Ala Lys
                           85                  90                  95

Asn Ala Lys Lys Ala Val Glu Asp Ala Gln Lys Ala Leu Asp Asp Ala
                       100                 105                 110

Lys Ala Ala Gln Lys Lys Tyr Asp Glu Asp Gln Lys Lys Thr Glu Glu
                       115                 120                 125

Lys Ala Ala Leu Glu Lys Ala Ala Ser Glu Glu Met Asp Lys Ala Val
                   130                 135                 140

Ala Ala Val Gln Gln Ala Tyr Leu Ala Tyr Gln Gln Ala Thr Asp Lys
       145                 150                 155                 160

Ala Ala Lys Asp Ala Ala Asp Lys Met Ile Asp Glu Ala Lys Lys Arg
                           165                 170                 175

Glu Glu Glu Ala Lys Thr Lys Phe Asn Thr Val Arg Ala Met Val Val
                       180                 185                 190
```

-continued

```
Pro  Glu  Pro  Glu  Gln  Leu  Ala  Glu  Thr  Lys  Lys  Lys  Ser  Glu  Glu  Ala
     195                      200                      205
Lys  Gln  Lys  Ala  Pro  Glu  Leu  Thr  Lys  Lys  Leu  Glu  Glu  Ala  Lys  Ala
     210                      215                      220
Lys  Leu  Glu  Glu  Ala  Glu  Lys  Ala  Thr  Glu  Ala  Lys  Gln  Lys  Val
225                      230                      235                      240
Asp  Ala  Glu  Glu  Val  Ala  Pro  Gln  Ala  Lys  Ile  Ala  Glu  Leu  Glu  Asn
                    245                      250                      255
Gln  Val  His  Arg  Leu  Glu  Gln  Glu  Leu  Lys  Glu  Ile  Asp  Glu  Ser  Glu
               260                      265                      270
Ser  Glu  Asp  Tyr  Ala  Lys  Glu  Gly  Phe  Arg  Ala  Pro  Leu  Gln  Ser  Lys
          275                      280                      285
Leu  Asp  Ala  Lys  Lys  Ala  Lys  Leu  Ser  Lys  Leu  Glu  Glu  Leu  Ser  Asp
     290                      295                      300
Lys  Ile  Asp  Glu  Leu  Asp  Ala  Glu  Ile  Ala  Lys  Leu  Glu  Asp  Gln  Leu
305                      310                      315                      320
Lys  Ala  Ala  Glu  Glu  Asn  Asn  Asn  Val  Glu  Asp  Tyr  Phe  Lys  Glu  Gly
                    325                      330                      335
Leu  Glu  Lys  Thr  Ile  Ala  Ala  Lys  Lys  Ala  Glu  Leu  Glu  Lys  Thr  Glu
               340                      345                      350
Ala  Asp  Leu  Lys  Lys  Ala  Val  Asn  Glu  Pro  Glu  Lys  Pro  Ala  Pro  Ala
          355                      360                      365
Pro  Glu  Thr  Pro  Ala  Pro  Glu  Ala  Pro  Ala  Glu  Gln  Pro  Lys  Pro  Ala
     370                      375                      380
Pro  Ala  Pro  Gln  Pro  Ala  Pro  Ala  Pro  Lys  Pro  Glu  Lys  Pro  Ala  Glu
385                      390                      395                      400
Gln  Pro  Lys  Pro  Glu  Lys  Thr  Asp  Asp  Gln  Gln  Ala  Glu  Glu  Asp  Tyr
                    405                      410                      415
Ala  Arg  Arg  Ser  Glu  Glu  Glu  Tyr  Asn  Arg  Leu  Thr  Gln  Gln  Gln  Pro
               420                      425                      430
Pro  Lys  Ala  Glu  Lys  Pro  Ala  Pro  Ala  Pro  Lys  Thr  Gly  Trp  Lys  Gln
          435                      440                      445
Glu  Asn  Gly  Met  Trp  Tyr  Phe  Tyr  Asn  Thr  Asp  Gly  Ser  Met  Ala  Thr
     450                      455                      460
Gly  Trp  Leu  Gln  Asn  Asn  Gly  Ser  Trp  Tyr  Tyr  Leu  Asn  Ser  Asn  Gly
465                      470                      475                      480
Ala  Met  Ala  Thr  Gly  Trp  Leu  Gln  Tyr  Asn  Gly  Ser  Trp  Tyr  Tyr  Leu
                    485                      490                      495
Asn  Ala  Asn  Gly  Ala  Met  Ala  Thr  Gly  Trp  Ala  Lys  Val  Asn  Gly  Ser
               500                      505                      510
Trp  Tyr  Tyr  Leu  Asn  Ala  Asn  Gly  Ala  Met  Ala  Thr  Gly  Trp  Leu  Gln
          515                      520                      525
Tyr  Asn  Gly  Ser  Trp  Tyr  Tyr  Leu  Asn  Ala  Asn  Gly  Ala  Met  Ala  Thr
     530                      535                      540
Gly  Trp  Ala  Lys  Val  Asn  Gly  Ser  Trp  Tyr  Tyr  Leu  Asn  Ala  Asn  Gly
545                      550                      555                      560
Ala  Met  Ala  Thr  Gly  Trp  Leu  Gln  Tyr  Asn  Gly  Ser  Trp  Tyr  Tyr  Leu
                    565                      570                      575
Asn  Ala  Asn  Gly  Ala  Met  Ala  Thr  Gly  Trp  Ala  Lys  Val  Asn  Gly  Ser
               580                      585                      590
Trp  Tyr  Tyr  Leu  Asn  Ala  Asn  Gly  Ala  Met  Ala  Thr  Gly  Trp  Val  Lys
          595                      600                      605
Asp  Gly  Asp  Thr  Trp  Tyr  Tyr  Leu  Glu  Ala  Ser  Gly  Ala  Met  Lys  Ala
     610                      615                      620
```

```
              Ser  Gln  Trp  Phe  Lys  Val  Ser  Asp  Lys  Trp  Tyr  Tyr  Val  Asn  Gly  Leu
              625                      630                      635                     640

Gly  Ala  Leu  Ala  Val  Asn  Thr  Thr  Val  Asp  Gly  Tyr  Lys  Val  Asn  Ala
                                  645                      650                     655

Asn  Gly  Glu  Trp  Val  Xaa  Ala  Asp  Xaa  Ile  Lys  Ala  Cys  Xaa  Glu  His
                             660                      665                     670

Leu  Thr  Phe  Xaa  Phe  Xaa  Asn  Lys  Asp  Lys  Val  Arg  Leu  Asn  Arg  Phe
                             675                      680                     685

Met  Phe  Val  Phe  Phe  Arg  Tyr
              690                      695
```

( 2 ) INFORMATION FOR SEQ ID NO:24:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: unknown ( x i ) SEQUENCE DESCRIPTION: SEQ ID NO:24:

```
              Glu  Glu  Tyr  Asn  Arg  Leu  Thr  Gln  Gln  Gln  Pro  Pro  Lys  Ala  Glu  Lys
              1                   5                        10                      15

Pro  Ala  Pro  Ala  Pro
                                  20
```

( 2 ) INFORMATION FOR SEQ ID NO:25:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: unknown ( x i ) SEQUENCE DESCRIPTION: SEQ ID NO:25:

```
              Gln  Gln  Gln  Pro  Pro  Lys  Ala
              1                   5
```

( 2 ) INFORMATION FOR SEQ ID NO:26:

( i ) SEQUENCE CHARACTERISTICS:
        ( A ) LENGTH: 484 amino acids
        ( B ) TYPE: amino acid
        ( C ) STRANDEDNESS:
        ( D ) TOPOLOGY: unknown ( x i ) SEQUENCE DESCRIPTION: SEQ ID NO:26:

```
              Met  Asn  Met  Lys  Lys  Ala  Thr  Ile  Ala  Ala  Thr  Ala  Gly  Ile  Ala  Val
              1                   5                        10                      15

Thr  Ala  Phe  Arg  Ala  Pro  Thr  Ile  Arg  Ser  Ala  Ser  Thr  Val  Val  Val
                             20                       25                      30

Glu  Ala  Gly  Asp  Thr  Leu  Trp  Gly  Ile  Ala  Gln  Ser  Lys  Gly  Thr  Thr
                             35                       40                      45

Val  Asp  Ala  Ile  Lys  Lys  Ala  Asn  Asn  Leu  Thr  Thr  Asp  Lys  Ile  Val
                        50                       55                      60

Pro  Gly  Gln  Lys  Leu  Gln  Val  Asn  Asn  Glu  Val  Ala  Ala  Ala  Glu  Lys
              65                       70                       75                      80

Thr  Glu  Lys  Ser  Val  Ser  Ala  Thr  Trp  Leu  Asn  Val  Arg  Ser  Gly  Ala
                                  85                       90                      95

Gly  Val  Asp  Asn  Ser  Ile  Ile  Thr  Ser  Ile  Lys  Gly  Gly  Thr  Lys  Val
                                  100                      105                     110

Thr  Val  Glu  Thr  Thr  Glu  Ser  Asn  Gly  Trp  His  Lys  Ile  Thr  Tyr  Asn
```

|     |     |     |     |     | 115 |     |     |     |     | 120 |     |     |     |     | 125 |     |     |     |     |
| --- | --- | --- | --- | --- | --- | --- | --- | --- | --- | --- | --- | --- | --- | --- | --- | --- | --- | --- | --- |
| Asp | Gly<br>130 | Lys | Thr | Gly | Phe | Val<br>135 | Asn | Gly | Lys | Tyr | Leu<br>140 | Thr | Asp | Lys | Ala |
| Val<br>145 | Ser | Thr | Pro | Val | Ala<br>150 | Pro | Thr | Gln | Glu | Val<br>155 | Lys | Lys | Glu | Thr | Thr<br>160 |
| Thr | Gln | Gln | Ala | Ala<br>165 | Pro | Ala | Ala | Glu | Thr<br>170 | Lys | Thr | Glu | Val | Lys<br>175 | Gln |
| Thr | Thr | Gln | Ala<br>180 | Thr | Thr | Pro | Ala | Pro<br>185 | Lys | Val | Ala | Glu | Thr<br>190 | Lys | Glu |
| Thr | Pro | Val<br>195 | Val | Asp | Gln | Asn | Ala<br>200 | Thr | Thr | His | Ala | Val<br>205 | Lys | Ser | Gly |
| Asp | Thr<br>210 | Ile | Trp | Ala | Leu | Ser<br>215 | Val | Lys | Tyr | Gly | Val<br>220 | Ser | Val | Gln | Asp |
| Ile<br>225 | Met | Ser | Trp | Asn | Asn<br>230 | Leu | Ser | Ser | Ser | Ser<br>235 | Ile | Tyr | Val | Gly | Gln<br>240 |
| Lys | Leu | Ala | Ile | Lys<br>245 | Gln | Thr | Ala | Asn | Thr<br>250 | Ala | Thr | Pro | Lys | Ala<br>255 | Glu |
| Val | Lys | Thr | Glu<br>260 | Ala | Pro | Ala | Ala | Glu<br>265 | Lys | Gln | Ala | Ala | Pro<br>270 | Val | Val |
| Lys | Glu | Asn<br>275 | Thr | Asn | Thr | Asn | Thr<br>280 | Ala | Thr | Thr | Glu | Lys<br>285 | Lys | Glu | Thr |
| Ala | Thr<br>290 | Gln | Gln | Gln | Thr | Ala<br>295 | Pro | Lys | Ala | Pro | Thr<br>300 | Glu | Ala | Ala | Lys |
| Pro<br>305 | Ala | Pro | Ala | Pro | Ser<br>310 | Thr | Asn | Thr | Asn | Ala<br>315 | Asn | Lys | Thr | Asn | Thr<br>320 |
| Asn | Thr | Asn | Thr | Asn<br>325 | Thr | Asn | Thr | Asn | Asn<br>330 | Thr | Asn | Thr | Asn | Thr<br>335 | Pro |
| Ser | Lys | Asn | Thr<br>340 | Asn | Thr | Asn | Ser | Asn<br>345 | Thr | Asn | Thr | Asn | Thr<br>350 | Asn | Ser |
| Asn | Thr | Asn<br>355 | Ala | Asn | Gln | Gly | Ser<br>360 | Ser | Asn | Asn | Asn | Ser<br>365 | Asn | Ser | Ser |
| Ala | Ser<br>370 | Ala | Ile | Ile | Ala | Glu<br>375 | Ala | Gln | Lys | His | Leu<br>380 | Gly | Lys | Ala | Tyr |
| Ser<br>385 | Trp | Gly | Gly | Asn | Gly<br>390 | Pro | Thr | Thr | Phe | Asp<br>395 | Cys | Ser | Gly | Tyr | Thr<br>400 |
| Lys | Tyr | Val | Phe | Ala<br>405 | Lys | Ala | Gly | Ile | Ser<br>410 | Leu | Pro | Arg | Thr | Ser<br>415 | Gly |
| Ala | Gln | Tyr | Ala<br>420 | Ser | Thr | Thr | Arg | Ile<br>425 | Ser | Glu | Ser | Gln | Ala<br>430 | Lys | Pro |
| Gly | Asp | Leu<br>435 | Val | Phe | Phe | Asp | Tyr<br>440 | Gly | Ser | Gly | Ile | Ser<br>445 | His | Val | Gly |
| Ile | Tyr<br>450 | Val | Gly | Asn | Gly | Gln<br>455 | Met | Ile | Asn | Ala | Gln<br>460 | Asp | Asn | Gly | Val |
| Lys<br>465 | Tyr | Asp | Asn | Ile | His<br>470 | Gly | Ser | Gly | Trp | Gly<br>475 | Lys | Tyr | Leu | Val | Gly<br>480 |
| Phe | Gly | Arg | Val |     |     |     |     |     |     |     |     |     |     |     |     |

(2) INFORMATION FOR SEQ ID NO:27:

(i) SEQUENCE CHARACTERISTICS:
        (A) LENGTH: 21 amino acids
        (B) TYPE: amino acid
        (C) STRANDEDNESS:
        (D) TOPOLOGY: unknown (xi) SEQUENCE DESCRIPTION: SEQ ID NO:27:

```
Ala Val Ser Thr Pro Val Ala Pro Thr Gln Glu Val Lys Lys Glu Thr
 1               5                   10                  15

Thr Thr Gln Gln Ala
                20
```

( 2 ) INFORMATION FOR SEQ ID NO:28:

( i ) SEQUENCE CHARACTERISTICS:
       ( A ) LENGTH: 7 amino acids
       ( B ) TYPE: amino acid
       ( C ) STRANDEDNESS:
       ( D ) TOPOLOGY: unknown ( x i ) SEQUENCE DESCRIPTION: SEQ ID NO:28:

```
Pro Thr Gln Glu Val Lys Lys
 1               5
```

( 2 ) INFORMATION FOR SEQ ID NO:29:

( i ) SEQUENCE CHARACTERISTICS:
       ( A ) LENGTH: 21 amino acids
       ( B ) TYPE: amino acid
       ( C ) STRANDEDNESS:
       ( D ) TOPOLOGY: unknown ( x i ) SEQUENCE DESCRIPTION: SEQ ID NO:29:

```
Val Lys Gln Thr Thr Gln Ala Thr Thr Pro Ala Pro Lys Val Ala Glu
 1               5                   10                  15

Thr Lys Glu Thr Pro
                20
```

( 2 ) INFORMATION FOR SEQ ID NO:30:

( i ) SEQUENCE CHARACTERISTICS:
       ( A ) LENGTH: 7 amino acids
       ( B ) TYPE: amino acid
       ( C ) STRANDEDNESS:
       ( D ) TOPOLOGY: unknown ( x i ) SEQUENCE DESCRIPTION: SEQ ID NO:30:

```
Thr Thr Pro Ala Pro Lys Val
 1               5
```

( 2 ) INFORMATION FOR SEQ ID NO:31:

( i ) SEQUENCE CHARACTERISTICS:
       ( A ) LENGTH: 21 amino acids
       ( B ) TYPE: amino acid
       ( C ) STRANDEDNESS:
       ( D ) TOPOLOGY: unknown ( x i ) SEQUENCE DESCRIPTION: SEQ ID NO:31:

```
Leu Ala Ile Lys Gln Thr Ala Asn Thr Ala Thr Pro Lys Ala Glu Val
 1               5                   10                  15

Lys Thr Glu Ala Pro
                20
```

( 2 ) INFORMATION FOR SEQ ID NO:32:

( i ) SEQUENCE CHARACTERISTICS:
       ( A ) LENGTH: 7 amino acids
       ( B ) TYPE: amino acid
       ( C ) STRANDEDNESS:
       ( D ) TOPOLOGY: unknown ( x i ) SEQUENCE DESCRIPTION: SEQ ID NO:32:

```
    Asn Thr Ala Thr Pro Lys Ala
    1               5
```

( 2 ) INFORMATION FOR SEQ ID NO:33:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: unknown ( x i ) SEQUENCE DESCRIPTION: SEQ ID NO:33:

```
    Lys Lys Glu Thr Ala Thr Gln Gln Gln Thr Ala Pro Lys Ala Pro Thr
    1               5                   10                  15

Glu Ala Ala Lys Pro
                20
```

( 2 ) INFORMATION FOR SEQ ID NO:34:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: unknown ( x i ) SEQUENCE DESCRIPTION: SEQ ID NO:34:

```
    Gln Gln Thr Ala Pro Lys Ala
    1               5
```

( 2 ) INFORMATION FOR SEQ ID NO:35:

( i ) SEQUENCE CHARACTERISTICS:
        ( A ) LENGTH: 99 amino acids
        ( B ) TYPE: amino acid
        ( C ) STRANDEDNESS:
        ( D ) TOPOLOGY: unknown ( x i ) SEQUENCE DESCRIPTION: SEQ ID NO:35:

```
    Met Lys Val Ser Ala Ala Leu Leu Cys Leu Leu Leu Ile Ala Ala Thr
    1               5                   10                  15

Phe Ile Pro Gln Gly Leu Ala Gln Pro Asp Ala Ile Asn Ala Pro Val
                20                  25                  30

Thr Cys Cys Tyr Asn Phe Thr Asn Arg Lys Ile Ser Val Gln Arg Leu
                35                  40                  45

Ala Ser Tyr Arg Arg Ile Thr Ser Ser Lys Cys Pro Lys Glu Ala Val
            50                  55                  60

Ile Phe Lys Thr Ile Val Ala Lys Glu Ile Cys Ala Asp Pro Lys Gln
    65                  70                  75                  80

Lys Trp Val Gln Asp Ser Met Asp His Leu Asp Lys Gln Thr Gln Thr
                        85                  90                  95

Pro Lys Thr
```

( 2 ) INFORMATION FOR SEQ ID NO:36:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: unknown ( x i ) SEQUENCE DESCRIPTION: SEQ ID NO:36:

```
    Ser Met Asp His Leu Asp Lys Gln Thr Gln Thr Pro Lys Thr
    1               5                   10
```

( 2 ) INFORMATION FOR SEQ ID NO:37:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: unknown ( x i ) SEQUENCE DESCRIPTION: SEQ ID NO:37:

```
Gln  Thr  Gln  Thr  Pro  Lys  Thr
1                    5
```

( 2 ) INFORMATION FOR SEQ ID NO:38:

( i ) SEQUENCE CHARACTERISTICS:
        ( A ) LENGTH: 67 amino acids
        ( B ) TYPE: amino acid
        ( C ) STRANDEDNESS:
        ( D ) TOPOLOGY: unknown ( x i ) SEQUENCE DESCRIPTION: SEQ ID NO:38:

```
Lys  Ser  Thr  Thr  Cys  Cys  Tyr  Arg  Phe  Ile  Asn  Lys  Lys  Ile  Pro  Lys
1                    5                        10                       15

Gln  Arg  Leu  Glu  Ser  Tyr  Arg  Arg  Thr  Thr  Ser  Ser  His  Cys  Pro  Arg
               20                       25                       30

Glu  Ala  Val  Ile  Phe  Lys  Asp  Lys  Glu  Ile  Cys  Ala  Asp  Pro  Thr  Gln
               35                  40                       45

Lys  Trp  Val  Gln  Asp  Phe  Met  Lys  His  Leu  Asp  Lys  Lys  Thr  Gln  Thr
     50                       55                       60

Pro  Lys  Leu
65
```

( 2 ) INFORMATION FOR SEQ ID NO:39:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: unknown ( x i ) SEQUENCE DESCRIPTION: SEQ ID NO:39:

```
Phe  Met  Lys  His  Leu  Asp  Lys  Lys  Thr  Gln  Thr  Pro  Lys  Leu
1                    5                        10
```

( 2 ) INFORMATION FOR SEQ ID NO:40:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: unknown ( x i ) SEQUENCE DESCRIPTION: SEQ ID NO:40:

```
Lys  Thr  Gln  Thr  Pro  Lys  Leu
1                    5
```